(12) United States Patent
Linder et al.

(10) Patent No.: US 6,951,570 B2
(45) Date of Patent: Oct. 4, 2005

(54) METHODS, SYSTEMS, AND DEVICES FOR DEPLOYING A FILTER FROM A FILTER DEVICE

(75) Inventors: Richard J. Linder, Sandy, UT (US); Daryl R. Edmiston, Sandy, UT (US); Steven W. Johnson, West Jordan, UT (US)

(73) Assignee: Rubicon Medical, Inc., Salt Lake City, UT (US)

(*) Notice: Subject to any disclaimer, the term of this patent is extended or adjusted under 35 U.S.C. 154(b) by 96 days.

(21) Appl. No.: 10/186,255

(22) Filed: Jun. 28, 2002

(65) Prior Publication Data

US 2003/0009188 A1 Jan. 9, 2003

Related U.S. Application Data

(60) Provisional application No. 60/302,417, filed on Jul. 2, 2001, provisional application No. 60/345,333, filed on Nov. 9, 2001, provisional application No. 60/341,092, filed on Dec. 12, 2001, and provisional application No. 60/347,500, filed on Jan. 11, 2002.

(51) Int. Cl.[7] ............................................. A61M 29/00
(52) U.S. Cl. ...................... 606/200; 606/159; 606/194
(58) Field of Search ............................. 606/191, 192, 606/194, 195, 198, 200, 159

(56) References Cited

U.S. PATENT DOCUMENTS

| | | | |
|---|---|---|---|
| 3,472,230 A | 10/1969 | Fogarty | |
| 3,592,186 A | 7/1971 | Oster | |
| 3,683,904 A | 8/1972 | Forster | |
| 3,889,657 A | 6/1975 | Baumgarten | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,279,593 A | 7/1981 | Rohlcke | |
| 4,413,989 A | 11/1983 | Schjeldahl et al. | ............ 604/96 |
| 4,425,908 A | 1/1984 | Simon | ............ 128/1 R |
| 4,447,227 A | 5/1984 | Kotsanis | |
| 4,580,568 A | 4/1986 | Gianturco | |
| 4,590,938 A | 5/1986 | Segura et al. | |
| 4,619,246 A | 10/1986 | Molgaard-Nielsen et al. | |
| 4,631,052 A | 12/1986 | Kensey | |

(Continued)

FOREIGN PATENT DOCUMENTS

| | | | |
|---|---|---|---|
| DE | 28 21 048 | 7/1980 | .......... A61M/17/22 |
| DE | 3107392 A1 | 9/1982 | .......... A61B/17/22 |

(Continued)

OTHER PUBLICATIONS

"Atherosclerotic Disease of the Aortic Arch as a Risk Factor of Recurrent Ischemic Stroke," *The New England Journal of Medicine*, pp. 1216–1221 (May 1996).

(Continued)

*Primary Examiner*—Anhtua T. Nguyen
*Assistant Examiner*—Jessica R Baxter
(74) *Attorney, Agent, or Firm*—Crompton, Seager & Tufte LLC

(57) ABSTRACT

A filter device is adapted to function as a guidewire, an exchange guidewire, and provide embolic protection during a procedure. The filter device includes a filter assembly that is either integral with or coupled to a guide member. The filter assembly includes a plurality of struts that expand outwardly to deploy a filter that collects or captures material flowing along the blood vessel within which the filter device is deployed. The plurality of struts are constrained by a restraining member or mechanism that prevents the plurality of struts from expanding or extending outwardly to deploy the filter. Cooperating with the restraining member or mechanism is an actuating assembly that is adapted to release the restraining member or mechanism and enable the filter to be deployed from the guide member. A capture catheter that cooperates with the filter device and substantially surrounds the filter during removal of the filter device.

26 Claims, 37 Drawing Sheets

U.S. PATENT DOCUMENTS

| | | |
|---|---|---|
| 4,643,184 A | 2/1987 | Mobin-Uddin |
| 4,650,466 A | 3/1987 | Luther |
| 4,662,885 A | 5/1987 | DiPisa, Jr. |
| 4,705,517 A | 11/1987 | DiPisa, Jr. |
| 4,706,671 A | 11/1987 | Weinrib ................. 128/348 |
| 4,723,549 A | 2/1988 | Wholey et al. ............ 128/344 |
| 4,728,319 A | 3/1988 | Masch |
| 4,733,665 A | 3/1988 | Palmaz |
| 4,790,812 A | 12/1988 | Hawkins, Jr. et al. ........ 604/22 |
| 4,790,813 A | 12/1988 | Kensey |
| 4,793,348 A | 12/1988 | Palmaz ................... 128/325 |
| 4,794,928 A | 1/1989 | Kletschka ................ 128/344 |
| 4,794,931 A | 1/1989 | Yock |
| 4,800,882 A | 1/1989 | Gianturco |
| 4,807,626 A | 2/1989 | McGirr |
| 4,842,579 A | 6/1989 | Shiber |
| 4,857,045 A | 8/1989 | Rydell |
| 4,857,046 A | 8/1989 | Stevens et al. |
| 4,867,157 A | 9/1989 | McGurk-Burleson et al. |
| 4,873,978 A | 10/1989 | Ginsburg ................. 128/345 |
| 4,886,061 A | 12/1989 | Fischell et al. |
| 4,898,575 A | 2/1990 | Fischell et al. |
| 4,907,336 A | 3/1990 | Gianturco |
| 4,921,478 A | 5/1990 | Solano et al. |
| 4,921,484 A | 5/1990 | Hillstead |
| 4,926,858 A | 5/1990 | Gifford, III et al. ........ 606/159 |
| 4,946,466 A | 8/1990 | Pinchuk et al. ............ 606/194 |
| 4,950,277 A | 8/1990 | Farr |
| 4,955,895 A | 9/1990 | Sugiyama et al. |
| 4,957,482 A | 9/1990 | Shiber |
| 4,964,409 A | 10/1990 | Tremulis .................. 128/657 |
| 4,969,891 A | 11/1990 | Gewertz |
| 4,979,951 A | 12/1990 | Simpson |
| 4,986,807 A | 1/1991 | Farr |
| 4,998,539 A | 3/1991 | Delsanti |
| 5,002,560 A | 3/1991 | Machold et al. |
| RE33,569 E | 4/1991 | Gifford, III et al. |
| 5,007,896 A | 4/1991 | Shiber |
| 5,007,917 A | 4/1991 | Evans |
| 5,011,488 A | 4/1991 | Ginsburg ................. 606/159 |
| 5,019,088 A | 5/1991 | Farr |
| 5,026,377 A | 6/1991 | Burton et al. |
| 5,041,126 A | 8/1991 | Gianturco |
| 5,053,008 A | 10/1991 | Bajaj |
| 5,053,044 A | 10/1991 | Mueller et al. |
| 5,071,407 A | 12/1991 | Termin et al. ............. 604/104 |
| 5,071,425 A | 12/1991 | Gifford, III et al. |
| 5,085,662 A | 2/1992 | Willard |
| 5,087,265 A | 2/1992 | Summers |
| 5,100,423 A | 3/1992 | Fearnot ................... 606/159 |
| 5,100,424 A | 3/1992 | Jang et al. |
| 5,100,425 A | 3/1992 | Fischell et al. |
| 5,102,415 A | 4/1992 | Guenther et al. |
| 5,104,399 A | 4/1992 | Lazarus |
| 5,108,419 A | 4/1992 | Reger et al. ............... 606/200 |
| 5,133,733 A | 7/1992 | Rasmussen et al. |
| 5,135,531 A | 8/1992 | Shiber |
| 5,152,771 A | 10/1992 | Sabbaghian et al. |
| 5,152,777 A | 10/1992 | Goldberg et al. ........... 606/200 |
| 5,160,342 A | 11/1992 | Reger et al. ............... 606/200 |
| 5,171,233 A | 12/1992 | Amplatz et al. |
| 5,190,546 A | 3/1993 | Jervis |
| 5,195,955 A | 3/1993 | Don Michael |
| 5,224,953 A | 7/1993 | Morgentaler |
| 5,226,909 A | 7/1993 | Evans et al. .............. 606/159 |
| 5,306,286 A | 4/1994 | Stack et al. |
| 5,314,444 A | 5/1994 | Gianturco |
| 5,314,472 A | 5/1994 | Fontaine |
| 5,315,996 A | 5/1994 | Lundquist ................. 128/642 |
| 5,318,576 A | 6/1994 | Plassche, Jr. et al. |
| 5,329,942 A | 7/1994 | Gunther et al. ............ 128/898 |
| 5,330,484 A | 7/1994 | Gunther et al. |
| 5,330,500 A | 7/1994 | Song |
| 5,350,398 A | 9/1994 | Pavcnik et al. |
| 5,354,310 A | 10/1994 | Garnic et al. |
| 5,356,423 A | 10/1994 | Tihon et al. |
| 5,366,464 A | 11/1994 | Belknap |
| 5,366,473 A | 11/1994 | Winston et al. |
| 5,370,657 A | 12/1994 | Irie |
| 5,370,683 A | 12/1994 | Fontaine |
| 5,376,100 A | 12/1994 | Lefebvre .................. 606/180 |
| 5,383,887 A | 1/1995 | Nadal |
| 5,383,892 A | 1/1995 | Cardon et al. |
| 5,383,926 A | 1/1995 | Lock et al. |
| 5,387,235 A | 2/1995 | Chuter |
| 5,395,349 A | 3/1995 | Quiachon et al. |
| 5,397,345 A | 3/1995 | Lazarus |
| 5,399,165 A | 3/1995 | Paul, Jr. ................... 604/95 |
| 5,405,377 A | 4/1995 | Cragg |
| 5,405,378 A | 4/1995 | Strecker .................. 623/1 |
| 5,409,454 A | 4/1995 | Fischell et al. |
| 5,415,630 A | 5/1995 | Gory et al. |
| 5,419,774 A | 5/1995 | Willard et al. |
| 5,421,832 A | 6/1995 | Lefebvre .................. 604/53 |
| 5,423,742 A | 6/1995 | Theron |
| 5,423,885 A | 6/1995 | Williams |
| 5,425,765 A | 6/1995 | Tiefenbrun et al. |
| 5,437,288 A | 8/1995 | Schwartz et al. ........... 128/772 |
| 5,441,483 A | 8/1995 | Avitall ................... 604/95 |
| 5,443,498 A | 8/1995 | Fontaine |
| 5,449,372 A | 9/1995 | Schmaltz et al. |
| 5,456,667 A | 10/1995 | Ham et al. |
| 5,462,529 A | 10/1995 | Simpson et al. |
| 5,476,104 A | 12/1995 | Sheahon |
| 5,484,418 A | 1/1996 | Quiachon et al. |
| 5,490,859 A * | 2/1996 | Mische et al. ............. 606/159 |
| 5,497,785 A | 3/1996 | Viera ..................... 128/772 |
| 5,507,767 A | 4/1996 | Maeda et al. |
| 5,512,044 A | 4/1996 | Duer |
| 5,527,354 A | 6/1996 | Fontaine et al. |
| 5,536,242 A | 7/1996 | Willard et al. |
| 5,540,707 A | 7/1996 | Ressemann et al. |
| 5,549,626 A | 8/1996 | Miller et al. ............... 606/200 |
| 5,562,724 A | 10/1996 | Vorwerk et al. |
| 5,569,274 A | 10/1996 | Rapacki et al. |
| 5,569,275 A | 10/1996 | Kotula et al. |
| 5,599,492 A | 2/1997 | Engelson .................. 264/167 |
| 5,601,568 A | 2/1997 | Chevillon et al. |
| 5,605,543 A | 2/1997 | Swanson .................. 604/96 |
| 5,634,897 A | 6/1997 | Dance et al. |
| 5,634,942 A | 6/1997 | Chevillon et al. ........... 623/1 |
| 5,658,296 A | 8/1997 | Bates et al. |
| 5,662,671 A | 9/1997 | Barbut et al. |
| 5,669,933 A | 9/1997 | Simon et al. |
| 5,695,519 A | 12/1997 | Summers et al. ........... 606/200 |
| 5,707,359 A | 1/1998 | Bufalini .................. 604/104 |
| 5,709,704 A | 1/1998 | Nott et al. ................ 606/200 |
| 5,720,764 A | 2/1998 | Naderlinger ............... 606/200 |
| 5,728,066 A | 3/1998 | Daneshvar |
| 5,746,758 A | 5/1998 | Nordgren et al. |
| 5,749,848 A | 5/1998 | Jang et al. |
| 5,769,816 A | 6/1998 | Barbut et al. ............... 604/96 |
| 5,779,716 A | 7/1998 | Cano et al. |
| 5,782,809 A | 7/1998 | Umeno et al. ............. 604/280 |
| 5,792,157 A | 8/1998 | Mische et al. |
| 5,792,300 A | 8/1998 | Inderbitzen et al. |
| 5,795,322 A | 8/1998 | Boudewijn ................ 604/22 |
| 5,797,952 A | 8/1998 | Klein |
| 5,800,457 A | 9/1998 | Gelbfish .................. 606/200 |
| 5,800,525 A | 9/1998 | Bachinski et al. |
| 5,807,330 A | 9/1998 | Teitelbaum ................ 604/96 |

| | | |
|---|---|---|
| 5,807,398 A | 9/1998 | Shaknovich |
| 5,810,874 A | 9/1998 | Lefebvre ............... 606/200 |
| 5,814,064 A | 9/1998 | Daniel et al. ............ 606/200 |
| 5,817,102 A | 10/1998 | Johnson et al. |
| 5,827,324 A | 10/1998 | Cassell et al. ............ 606/200 |
| 5,833,632 A | 11/1998 | Jacobsen et al. ........... 600/585 |
| 5,833,644 A | 11/1998 | Zadno-Azizi et al. |
| 5,833,650 A | 11/1998 | Imran |
| 5,836,969 A | 11/1998 | Kim et al. ............... 606/200 |
| 5,843,050 A | 12/1998 | Jones et al. ............. 604/280 |
| 5,846,260 A | 12/1998 | Maahs |
| 5,846,261 A | 12/1998 | Kotula et al. |
| 5,848,964 A | 12/1998 | Samuels |
| 5,873,906 A | 2/1999 | Lau et al. ................ 623/1 |
| 5,876,367 A | 3/1999 | Kaganov et al. ............ 604/8 |
| 5,893,867 A | 4/1999 | Bagaoisan et al. |
| 5,895,399 A | 4/1999 | Barbut et al. ............ 606/159 |
| 5,895,407 A | 4/1999 | Jayaraman |
| 5,902,263 A | 5/1999 | Patterson et al. |
| 5,906,618 A | 5/1999 | Larson, III |
| 5,908,435 A | 6/1999 | Samuels |
| 5,910,154 A | 6/1999 | Tsugita et al. ............ 606/200 |
| 5,911,734 A | 6/1999 | Tsugita et al. ............ 606/200 |
| 5,916,193 A | 6/1999 | Stevens et al. |
| 5,919,225 A | 7/1999 | Lau et al. ................ 623/1 |
| 5,921,924 A | 7/1999 | Avitall ................. 600/374 |
| 5,925,016 A | 7/1999 | Chornenky et al. |
| 5,925,060 A | 7/1999 | Forber |
| 5,925,062 A | 7/1999 | Purdy |
| 5,925,063 A | 7/1999 | Khosravi |
| 5,928,203 A | 7/1999 | Davey et al. |
| 5,928,218 A | 7/1999 | Gelbfish |
| 5,934,284 A | 8/1999 | Plaia et al. |
| 5,935,139 A | 8/1999 | Bates |
| 5,938,645 A | 8/1999 | Gordon |
| 5,941,869 A | 8/1999 | Patterson et al. |
| 5,941,896 A | 8/1999 | Kerr |
| 5,947,995 A | 9/1999 | Samuels |
| 5,951,585 A | 9/1999 | Cathcart et al. |
| 5,954,745 A * | 9/1999 | Gertler et al. ............ 606/200 |
| 5,976,172 A | 11/1999 | Homsma et al. |
| 5,980,555 A | 11/1999 | Barbut et al. |
| 5,989,210 A | 11/1999 | Morris et al. |
| 5,989,271 A | 11/1999 | Bonnette et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A * | 12/1999 | Daniel et al. ............ 606/200 |
| 6,004,279 A | 12/1999 | Crowley et al. ........... 600/585 |
| 6,007,557 A | 12/1999 | Ambrisco et al. |
| 6,007,558 A | 12/1999 | Ravenscroft et al. ....... 606/200 |
| 6,010,522 A | 1/2000 | Barbut et al. |
| 6,013,085 A | 1/2000 | Howard |
| 6,022,336 A | 2/2000 | Zadno-Azizi et al. ........ 604/96 |
| 6,027,520 A | 2/2000 | Tsugita et al. |
| 6,039,744 A | 3/2000 | Forber |
| 6,042,598 A | 3/2000 | Tsugita et al. ............ 606/200 |
| 6,048,338 A | 4/2000 | Larson et al. ............ 604/523 |
| 6,051,014 A | 4/2000 | Jang |
| 6,051,015 A | 4/2000 | Maahs |
| 6,053,932 A | 4/2000 | Daniel et al. ............ 606/200 |
| 6,059,814 A * | 5/2000 | Ladd .................. 606/200 |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,099,549 A | 8/2000 | Bosma et al. ............ 606/200 |
| 6,117,154 A | 9/2000 | Barbut et al. |
| 6,126,685 A | 10/2000 | Lenker et al. ............. 623/1 |
| 6,129,739 A | 10/2000 | Khosravi |
| 6,136,016 A | 10/2000 | Barbut et al. |
| 6,142,987 A | 11/2000 | Tsugita |
| 6,146,396 A | 11/2000 | Kónya et al. ............ 606/159 |
| 6,152,946 A | 11/2000 | Broome et al. ........... 606/200 |
| 6,165,200 A | 12/2000 | Tsugita et al. ............ 606/200 |
| 6,168,579 B1 | 1/2001 | Tsugita |
| 6,168,603 B1 | 1/2001 | Leslie et al. ............. 606/114 |
| 6,168,604 B1 | 1/2001 | Cano ................... 606/114 |
| 6,171,327 B1 * | 1/2001 | Daniel et al. ............ 606/200 |
| 6,171,328 B1 | 1/2001 | Addis .................. 606/200 |
| 6,174,318 B1 * | 1/2001 | Bates et al. ............. 606/127 |
| 6,179,851 B1 | 1/2001 | Barbut et al. |
| 6,179,859 B1 | 1/2001 | Bates et al. |
| 6,179,860 B1 | 1/2001 | Fulton, III et al. ........ 606/200 |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,217,567 B1 | 4/2001 | Zadno-Azizi et al. ....... 604/530 |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 * | 6/2001 | Addis .................. 606/200 |
| 6,245,088 B1 | 6/2001 | Lowery |
| 6,245,089 B1 | 6/2001 | Daniel et al. ............ 606/200 |
| 6,254,628 B1 | 7/2001 | Wallace et al. ........... 623/1.12 |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 * | 8/2001 | Levinson et al. .......... 606/200 |
| 6,280,413 B1 | 8/2001 | Clark et al. |
| 6,287,321 B1 | 9/2001 | Jang |
| 6,290,710 B1 | 9/2001 | Cryer et al. ............ 606/200 |
| 6,309,399 B1 | 10/2001 | Barbut et al. |
| 6,319,268 B1 | 11/2001 | Ambrisco et al. |
| 6,344,049 B1 | 2/2002 | Levinson et al. |
| 6,352,561 B1 | 3/2002 | Leopold et al. ........... 623/123 |
| 6,355,051 B1 | 3/2002 | Sisskind et al. |
| 6,361,545 B1 | 3/2002 | Macoviak et al. .......... 606/200 |
| 6,383,206 B1 | 5/2002 | Gillick et al. |
| 6,394,017 B2 | 5/2002 | Pavon et al. |
| 6,423,086 B1 | 7/2002 | Barbut et al. |
| 6,447,540 B1 | 9/2002 | Fontaine et al. |
| 6,468,298 B1 | 10/2002 | Pelton |
| 6,485,501 B1 | 11/2002 | Green |
| 6,537,295 B2 * | 3/2003 | Petersen ............... 606/200 |
| 6,558,396 B1 | 5/2003 | Lnoue .................. 606/108 |
| 6,562,058 B2 | 5/2003 | Seguin et al. ............ 606/200 |
| 2001/0031981 A1 | 10/2001 | Evans et al. ............ 606/200 |
| 2002/0016564 A1 | 2/2002 | Courtney et al. ........... 604/96 |
| 2002/0029077 A1 | 3/2002 | Leopold et al. ........... 623/1.11 |
| 2003/0236565 A1 | 12/2003 | DiMatteo et al. |
| 2004/0087965 A1 | 5/2004 | Levine et al. |

FOREIGN PATENT DOCUMENTS

| | | | |
|---|---|---|---|
| DE | 34 17 738 | 11/1985 | ........... A61M/1/34 |
| DE | 40 30 998 A1 | 10/1990 | ........... A61F/2/01 |
| DE | 4 030 998 A | 4/1991 | |
| EP | 0 200 688 | 11/1986 | ........... A61B/17/22 |
| EP | 0 293 605 A1 | 12/1988 | ........... A61F/2/02 |
| EP | 0 411 118 A1 | 2/1991 | ........... A61M/25/00 |
| EP | 0 427 429 A2 | 5/1991 | ........... A61M/25/10 |
| EP | 0 437 121 B1 | 7/1991 | ........... A61F/2/02 |
| EP | 0 472 334 A1 | 2/1992 | ........... A61F/2/02 |
| EP | 0 472 368 A2 | 2/1992 | ........... A61B/17/22 |
| EP | 0 533 511 A1 | 3/1993 | ........... A61M/29/02 |
| EP | 0564894 A1 | 10/1993 | ........... A61M/25/01 |

| | | | | |
|---|---|---|---|---|
| EP | 0 655 228 A1 | 11/1994 | ............ | A61F/2/02 |
| EP | 0 686 379 A2 | 6/1995 | ............ | A61F/2/06 |
| EP | 0 696 447 A2 | 2/1996 | ............ | A61F/2/06 |
| EP | 0 737 450 A1 | 10/1996 | | |
| EP | 0 743 046 A1 | 11/1996 | ............ | A61F/2/01 |
| EP | 0 759 287 A1 | 2/1997 | ............ | A61F/2/01 |
| EP | 0 711 549 A2 | 5/1997 | ............ | A61F/2/01 |
| EP | 0 784 988 A1 | 7/1997 | .......... | A61M/5/165 |
| EP | 0 852 132 A1 | 7/1998 | ............ | A61F/2/01 |
| EP | 0737450 B1 | 11/2003 | ............ | A61F/2/01 |
| FR | 2 580 504 | 10/1986 | ............ | A61M/1/00 |
| FR | 2606642 A1 | 11/1986 | ............ | A61F/1/34 |
| FR | 2 643 250 A1 | 8/1990 | ........... | A61B/17/00 |
| FR | 2 666 980 | 3/1992 | ............ | A61F/2/02 |
| FR | 2761592 A1 | 4/1997 | ............ | A61F/2/01 |
| FR | 2768326 A1 | 9/1997 | ............ | A61F/2/01 |
| FR | 2 768 326 A1 | 9/1999 | .......... | A61F/02/01 |
| GB | 2 020 557 A | 5/1979 | | |
| GB | 2 020 557 B | 1/1983 | .......... | A61B/17/50 |
| JP | 8-187294 A | 7/1996 | .......... | A61M/29/00 |
| RU | 764684 | 9/1980 | .......... | A61M/25/00 |
| WO | WO 88/09683 | 12/1988 | .......... | A61M/29/02 |
| WO | WO 92/03097 | 3/1992 | .......... | A61B/17/00 |
| WO | WO 94/14389 | 7/1994 | ............ | A61F/2/02 |
| WO | WO 94/19039 | 9/1994 | ............ | A61M/5/32 |
| WO | WO 94/24946 | 11/1994 | .......... | A61B/17/22 |
| WO | WO 96/01591 | 1/1996 | | |
| WO | WO 96/04875 A1 | 2/1996 | .......... | A61F/13/20 |
| WO | WO 96/10375 | 4/1996 | ............ | A61F/2/06 |
| WO | WO 96/19941 | 7/1996 | .......... | A61B/17/00 |
| WO | WO 96/23441 | 8/1996 | ............ | A61B/5/00 |
| WO | WO 96/33677 | 10/1996 | ............ | A61F/11/00 |
| WO | WO 97/17100 | 5/1997 | .......... | A61M/29/00 |
| WO | WO 97/27808 | 8/1997 | .......... | A61B/17/22 |
| WO | WO 97/42879 | 11/1997 | .......... | A61B/17/00 |
| WO | WO 98/02084 | 1/1998 | | |
| WO | WO 98/02112 | 1/1998 | | |
| WO | WO 98/23322 | 6/1998 | .......... | A61M/29/00 |
| WO | WO 98/33443 | 8/1998 | | |
| WO | WO 98/34673 | 8/1998 | .......... | A61M/31/00 |
| WO | WO 98/36786 | 8/1998 | ............ | A61M/5/32 |
| WO | WO 98/38920 | 9/1998 | .......... | A61M/17/00 |
| WO | WO 98/38929 | 9/1998 | .......... | A61M/17/22 |
| WO | WO 98/39046 | 9/1998 | .......... | A61M/25/00 |
| WO | WO 98/39053 | 9/1998 | .......... | A61M/29/00 |
| WO | WO 98/46297 | 10/1998 | .......... | A61M/29/00 |
| WO | WO 98/47447 | 10/1998 | ............ | A61F/2/06 |
| WO | WO 98/49952 | 11/1998 | .......... | A61B/17/32 |
| WO | WO 98/50103 | 11/1998 | .......... | A61M/29/00 |
| WO | WO 98/51237 | 11/1998 | ............ | A61F/2/01 |
| WO | WO 98/55175 | 12/1998 | .......... | A61M/29/00 |
| WO | WO 99/09895 | 3/1999 | .......... | A61B/17/12 |
| WO | WO 99/22673 | 5/1999 | ............ | A61F/2/01 |
| WO | WO 99/23976 | 5/1999 | ............ | A61F/2/01 |
| WO | WO 99/25252 | 5/1999 | .......... | A61B/17/00 |
| WO | WO 99/30766 | 6/1999 | .......... | A61M/29/00 |
| WO | 0 934 729 | 8/1999 | .......... | A61B/17/22 |
| WO | WO 99/40964 | 8/1999 | .......... | A61B/29/02 |
| WO | WO 99/42059 | 8/1999 | ............ | A61F/2/06 |
| WO | WO 99/44510 | 9/1999 | .......... | A61B/17/00 |
| WO | WO 99/44542 | 9/1999 | ............ | A61F/2/06 |
| WO | WO 99/55236 | 11/1999 | .......... | A61B/17/00 |
| WO | WO 99/58068 | 11/1999 | .......... | A61B/17/22 |
| WO | WO 99/65417 | 12/1999 | ............ | A61F/2/06 |
| WO | WO 00/07655 | 2/2000 | .......... | A61M/29/00 |
| WO | WO 00/09054 | 2/2000 | ............ | A61F/7/12 |
| WO | WO 00/16705 | 3/2000 | ............ | A61F/17/22 |
| WO | WO 00/20064 | 4/2000 | .......... | A61M/25/01 |
| WO | WO 200020064 A1 | 4/2000 | .......... | A61M/25/00 |
| WO | WO 00/49970 | 8/2000 | ............ | A61F/2/01 |
| WO | WO 00/64356 | 11/2000 | .......... | A61B/17/22 |
| WO | WO 00/67671 | 11/2000 | ............ | A61F/2/01 |
| WO | WO 01/91844 | 12/2001 | .......... | A61M/29/00 |

OTHER PUBLICATIONS

"Endovascular Grafts, Stents Drive Interventional Radiology Growth, " *Cardiovascular Device Update,* 2(3):1–12 (Mar. 1996).

"Protruding Atheromas in the Thoracic Aortic and Systemic Embolization, " pp. 423–427 American College of Physicians (1991).

"Recognition and Embolic Potential of Intraaortic Atherosclerotic Debris, " American College of Cardiology (Jan. 1991).

Cragg, Andrew et al., "A New Percutaneous Vena Cava Filger, " *AJR, 141*:601–604 (Sep. 1983).

Cragg, Andrew et al., "Nonsurgical Placement of Arterial Endoprosthesis: A New Technique Using Nitinol Wire," *AJR,* pp. 261–263 (Apr. 1983).

Diethrich et al., "Precutaneous Techniques for Endoluminal Carotid Interventions," *J. Endovasc. Surg.,* 3:182–202 (1996).

Fadali, A. Moneim, "A filtering device for the prevention of particulate embolization during the course of cardiac surgery, " *Surgery,* 64(3):634–639 (Sep. 1968).

Haissaguerre et al., "Spontaneous Initiation of Atrial Fibrillation by Ectopic Beats Originating in the Pulmonary Veins," *The New England Journal of Medicine,* 339(10):659–666 (Sep. 1988).

Jordan, Jr. et al., "Microemboli Detected by Transcranial Doppler Monitoring . . . ," *Cardiovascular Surgery,* 7(1)33–38 (Jan. 1999).

Lesh, "Can Catheter Ablation Cure Atrial Fibrillation?" *ACC Current Journal Review,* pp. 38–40 (Sep./Oct. 1997).

Lund et al., "Long–Term Patentcy of Ductus Arteriosus After Balloon Dilation: an Experimental Study," *Laboratory Investigation,* 69(4):772–774 (Apr. 1984).

Marache et al., "Percutaneous Transluminal Venous Angioplasty . . . ," *American Heart Journal,* 125(2 Pt 1):362–366 (Feb. 1993).

Mazur et al., "Directional Atherectomy with the Omnicath™: A Unique New Catheter System," *Catheterization and Cardiovascular Diagnosis,* 31:17–84 (1994).

Moussa, MD, Issaam "Stents Don't Require Systemic Anticoagulation . . . But the Technique (and Results) Must be Optimal," *Journal of Invasive Cardiol.,* 8(E):3E–7E, (1996).

Nakanishi et al., "Catheter Intervention to Venous System Using Expandable Metallic Stents," *Rinsho Kyobu Geka,* 14(2) :English Abstract Only (Apr. 1994).

Onal et al., "Primary Stenting for Complex Atherosclerotic Plaques in Aortic and Iliac Stenoses," *Cardiovascular & Interventional Radiology,* 21(5):386–392 (1998).

Theron et al., "New Triple Coaxial Catheter System for Carotid Angioplasty with Cerebral Protection, " *American Journal of Neuroradiology,* 11:869–874 (1990).

Tunick et al., "Protruding atherosclerotic plaque in the aortic archo f patients with systemic embolization: A new finding seen by transesohageal echocardiography," *American Heart Journal* 120(3):658–660 (Sep. 1990).

Waksman et al., "Distal Embolization is Common After Directional Atherectomy. . . ," *American Heart Journal,* 129(3):430–435 (1995).

Wholey, Mark H. et al., PTA and Stents in the Treatment of Extracranial Circulation, *The Journal of Invasive Cardiology,* 8(E):25E–30E (1996).

* cited by examiner

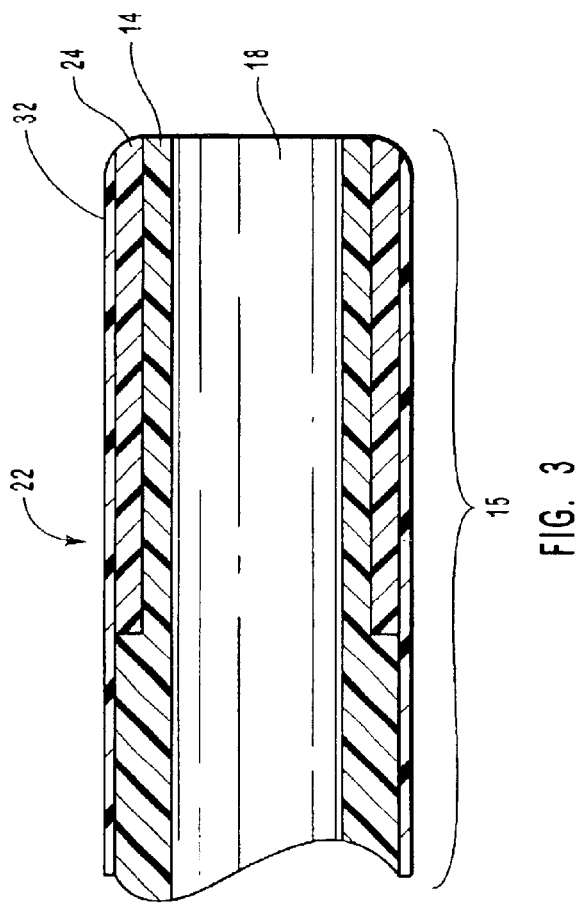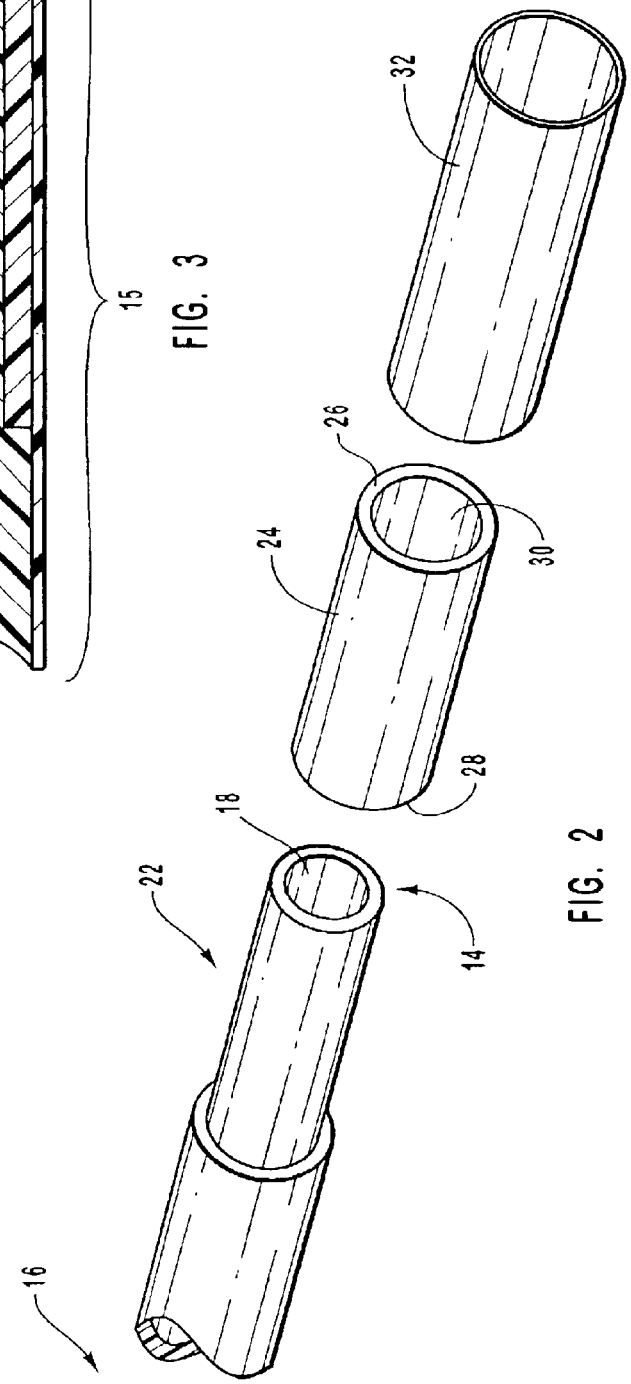

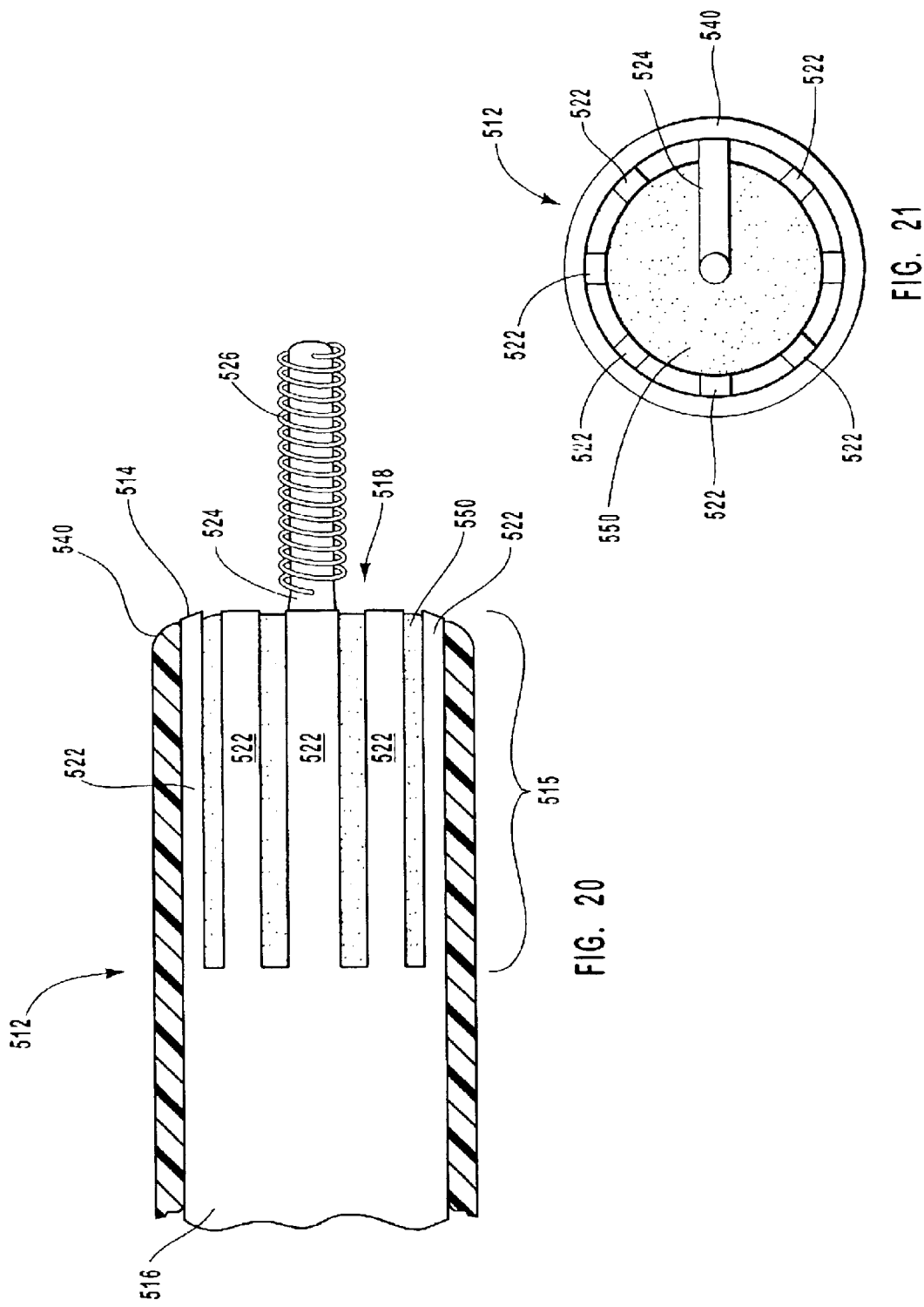

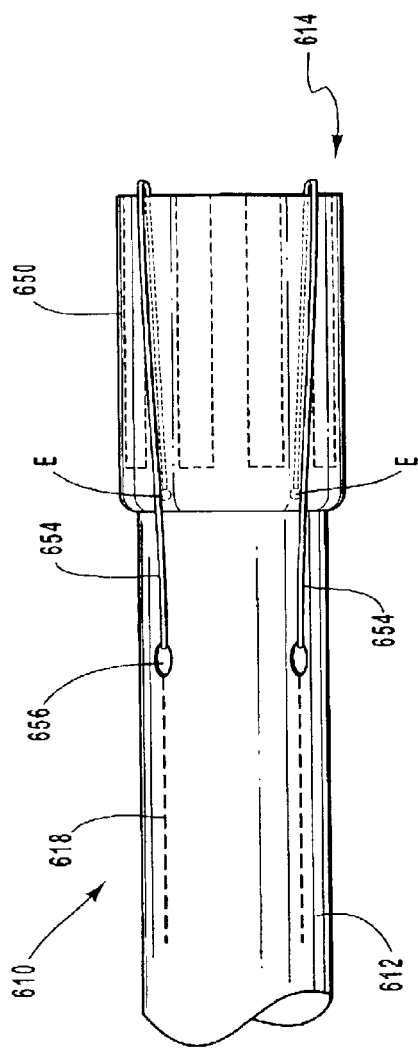
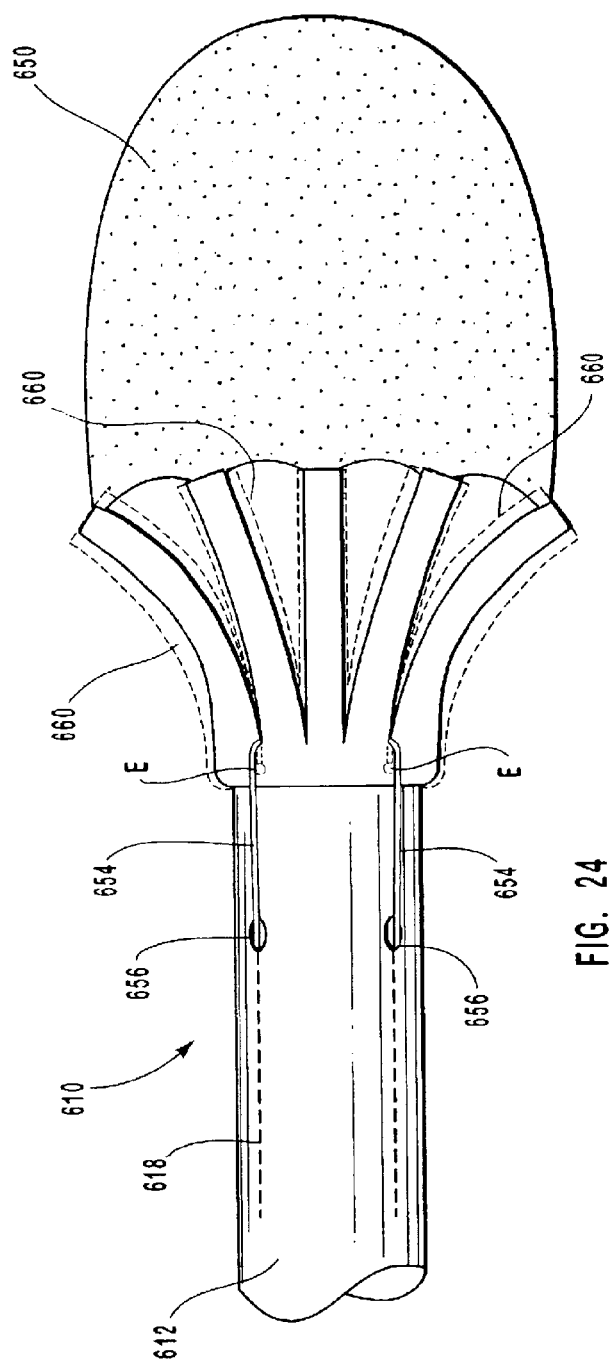
FIG. 23
FIG. 24

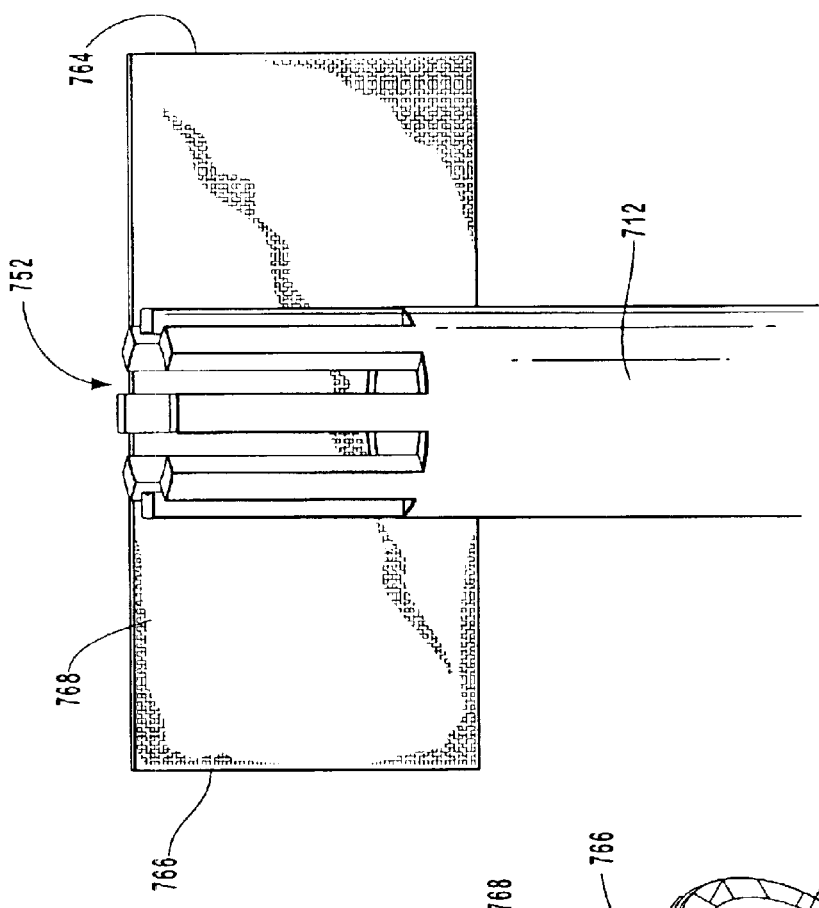
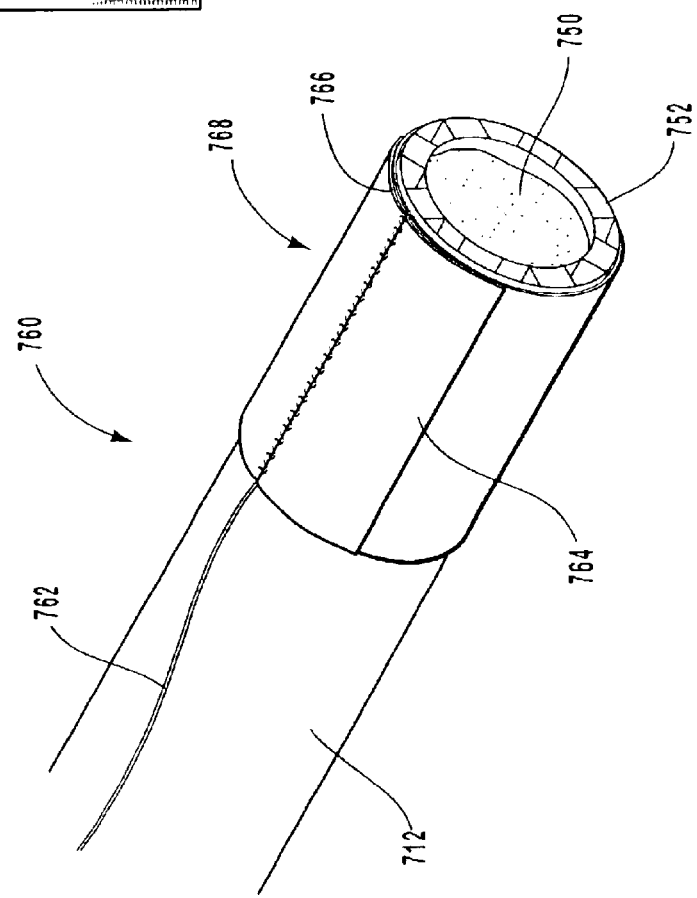
FIG. 27
FIG. 26

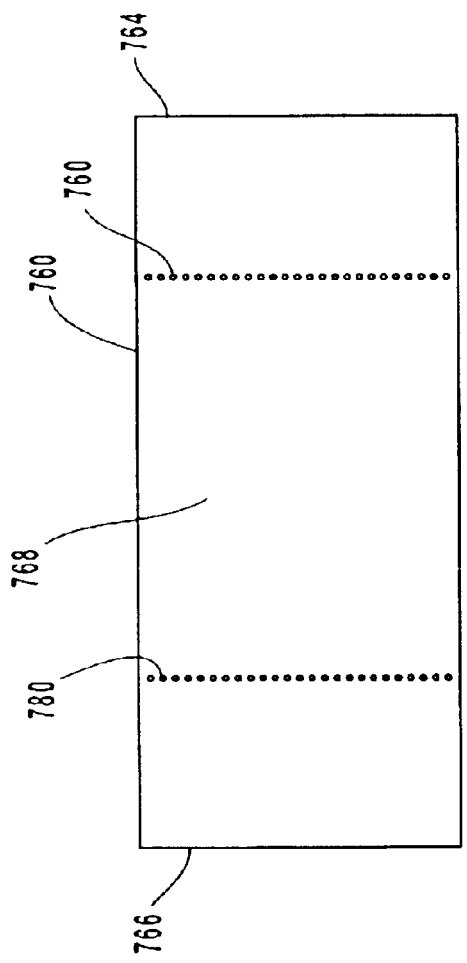
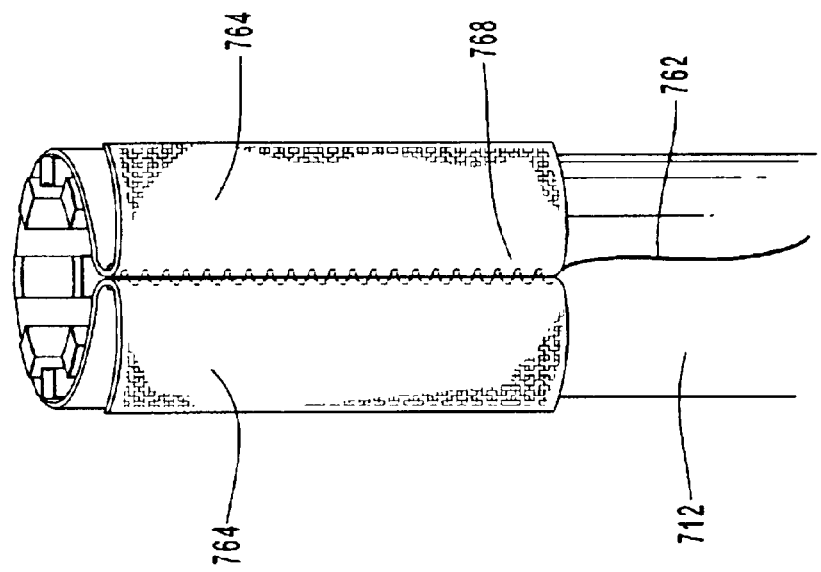

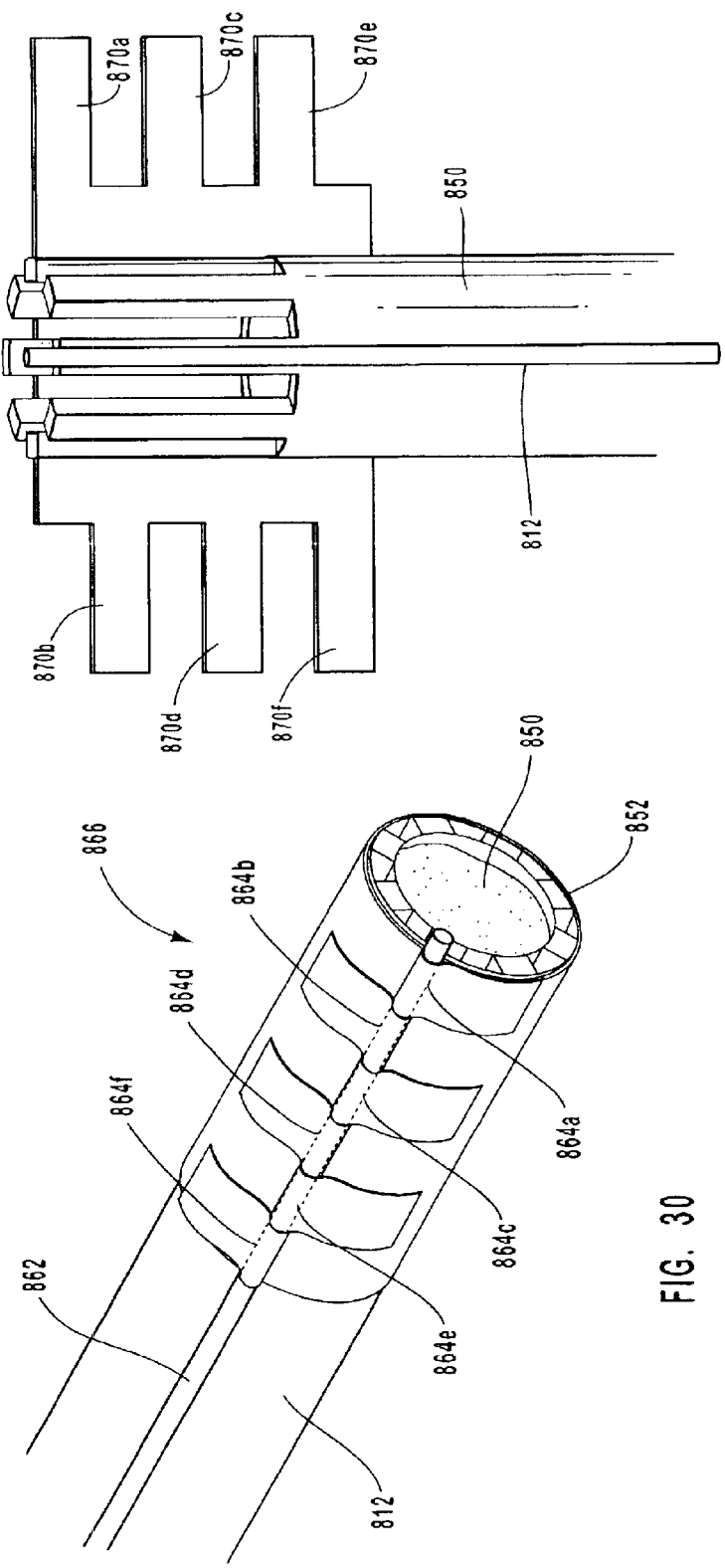
FIG. 31
FIG. 30
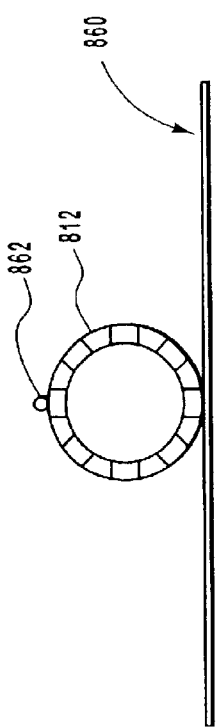
FIG. 32

METHODS, SYSTEMS, AND DEVICES FOR DEPLOYING A FILTER FROM A FILTER DEVICE

CROSS-REFERENCE TO RELATED APPLICATIONS

This patent application claims priority to U.S. Provisional Patent Application Ser. No. 60/302,417, filed Jul. 2, 2001, U.S. Provisional Patent Application Ser. No. 60/345,333, filed Nov. 9, 2001, U.S. Provisional Patent Application Ser. No. 60/347,500, filed Jan. 11, 2002 and U.S. Provisional Patent Application Ser. No. 60/341,092, filed Dec. 12, 2001, the disclosures of which are herein incorporated by this reference.

Additionally, this patent application incorporates by reference the disclosure of patent applications entitled "Methods, Systems, and Devices for providing Embolic Protection and Removing Embolic Material," U.S. patent application Ser. No. 10/186,275, "Methods, Systems, and Devices for Deploying an Embolic Protection Filter," U.S. patent application Ser. No. 10/186,292, and "Methods, Systems, and Devices for Providing Embolic Protection," U.S. patent application Ser. No. 10/186,304.

BACKGROUND OF THE INVENTION

1. The Field of the Invention

The present invention relates generally to the field of percutaneous medical filters, and more specifically, to vascular filter devices that are configured for percutaneous insertion into a blood vessel of a patient.

2. The Relevant Technology

Human blood vessels often become occluded or blocked by plaque, thrombi, other deposits, or material that reduce the blood carrying capacity of the vessel. Should the blockage occur at a critical place in the circulatory system, serious and permanent injury, and even death, can occur. To prevent this, some form of medical intervention is usually performed when significant occlusion is detected.

Several procedures are now used to open these stenosed or occluded blood vessels in a patient caused by the deposit of plaque or other material on the walls of the blood vessels. Angioplasty, for example, is a widely known procedure wherein an inflatable balloon is introduced into the occluded region. The balloon is inflated, dilating the occlusion, and thereby increasing the intraluminal diameter.

Another procedure is atherectomy. During atherectomy, a catheter is inserted into a narrowed artery to remove the matter occluding or narrowing the artery, i.e., fatty material. The catheter includes a rotating blade or cutter disposed in the tip thereof. Also located at the tip are an aperture and a balloon disposed on the opposite side of the catheter tip from the aperture. As the tip is placed in close proximity to the fatty material, the balloon is inflated to force the aperture into contact with the fatty material. When the blade is rotated, portions of the fatty material are shaved off and retained within the interior lumen of the catheter. This process is repeated until a sufficient amount of fatty material is removed and substantially normal blood flow is resumed.

In another procedure, stenosis within arteries and other blood vessels is treated by permanently or temporarily introducing a stent into the stenosed region to open the lumen of the vessel. The stent typically comprises a substantially cylindrical tube or mesh sleeve made from such materials as stainless steel or nitinol. The design of the material permits the diameter of the stent to be radially expanded, while still providing sufficient rigidity such that the stent maintains its shape once it has been enlarged to a desired size.

Unfortunately, such percutaneous interventional procedures, i.e., angioplasty, atherectomy, and stenting, often dislodge material from the vessel walls. This dislodged material can enter the bloodstream, and may be large enough to occlude smaller downstream vessels, potentially blocking blood flow to tissue. The resulting ischemia poses a serious threat to the health or life of a patient if the blockage occurs in critical tissue, such as the heart, lungs, kidneys, or brain, resulting in a stroke or infarction.

In general, existing devices and technology have a number of disadvantages including high profile, difficulty using multiple parts and components that result in an involved procedure, manufacturing complexity, and complex operation of the device or system.

BRIEF SUMMARY OF THE INVENTION

Embodiments of the present invention provide systems, methods, and devices for overcoming the above-referenced problems. More specifically, embodiments of the present invention include filter devices that have small, low, or no profiles, few parts and components, and are simple to manufacture and use. Consequently, embodiments of the present invention are able to be easily inserted into a patient, be steerable through the tortuous anatomy of a patient, provide filtering capabilities, have a sufficiently low profile to provide exchange capability so other medical devices can be advanced along the filter device, and be capable of removing the captured material without allowing such material to escape during filter retrieval.

According to one aspect of one embodiment of present invention, an illustrative embodiment of the present invention includes a vascular filter device. This device includes a guide member, such as a guidewire or hypo-tube having a lumen that extends from a distal end toward a proximal end thereof. Disposed within the lumen are one or more actuating members and a filter assembly. The one or more actuating members are coupled to an actuating mechanism at the proximal end of the guide member and are configured to deploy the filter assembly during a procedure, such as through movement of one or more actuating members.

The filter assembly includes a filter and a plurality of radially spaced-apart struts connected to a peripheral edge of a proximal end of the filter. The struts expand outwardly upon being deployed from the lumen of the guide member to place the peripheral edge of the proximal end of the filter adjacent to the wall of the vessel.

The filter includes a plurality of pores or holes that are so sized to capture material that may become detached during the procedure. The proximal end of the filter is configured to be constrained against the blood vessel within which the filter is disposed, while the distal end, in one embodiment, is configured to "float" within the blood flowing through the blood vessel and change shape to collect material and maintain the flow of blood through the vessel.

In one embodiment of the present invention, the filter device includes a number of radiopaque bands and/or markers affixed to a variety of positions on the device. These radiopaque bands and/or markers are one example of means for radiopacity, with various other means for radiopacity being known to those skilled in the art.

During use of the filter device of the present invention, blood flow will cause the filter to assume a parachute-like configuration such that material is collected within the interior of the filter. To remove the filter and the material, in one embodiment, the actuating member is moved in the proximal direction so that the proximal end of the filter cooperates with the distal end of the lumen through the guide member. Upon positioning the proximal end of the filter, a capture catheter is moved or advanced along the guide member until the catheter substantially encloses the filter. Following positioning of the capture catheter, the catheter and guide member are removed from the patient.

According to another embodiment of the present invention, a guide member includes a plurality of struts disposed at the distal end of the guide member. In one configuration, the distal end of the guide member is divided into a plurality of struts, at least two of which are biased to move outwardly. In another configuration, a strut assembly is coupled to the distal end of the guide member, with the strut assembly including one or more struts attached to the filter, while formed at a distal end of a third strut is a coil tip. This third strut is optionally biased toward the center of the lumen of the guide member. Before the filter is deployed, the filter is folded about the distal end of the guide member, folded about one or more of the plurality of struts, and/or is positioned within the lumen of the guide member.

To maintain the struts in the closed position, i.e., not extending outwardly from the remaining body of the guide member, a retaining member or mechanism cooperates with the guide member and/or struts and applies a restraining force to one or more of the struts. By moving the guide member relative to the restraining member, or vice versa, the distal ends of two or more of the biased struts are allowed to move outwardly to deploy the filter, i.e., the restraining force is released.

In another configuration, the restraining member or mechanism surrounds a tip of the guide member, including the struts and a part of the guide member. This restraining member or mechanism can be attached to the struts and is configured to apply a restraining force to the one or more struts. In one configuration, the restraining member or mechanism is configured to separate into a number of different sections to allow the distal ends of two or more of the biased struts to move outwardly to deploy the filter. In another embodiment, the restraining member or mechanism includes two or more actuating members that are attached to a location just proximal to the proximal end of each strut. The two or more actuating members extend to the distal end of the guide member, pass through apertures in the distal end of the restraining member or mechanism, and terminate within the lumen of the guide member after passing through holes formed in the guide member proximal to the proximal end of each strut.

To actuate the filter device, an actuating assembly at the proximal end of the guide member draws the actuating members in the proximal direction. Since one end of the actuating member is located at the proximal end of the restraining member or mechanism, whether forming part of the restraining member or mechanism, attached to the restraining member or mechanism, or attached to the guide member, pulling the actuating member in the proximal direction causes the actuating member to preferentially separate the restraining member or mechanism, thereby releasing the strut.

In another configuration, the restraining member or mechanism includes a plurality of apertures formed therein. The restraining member or mechanism has a first portion and a second portion with one or more of the plurality of apertures formed therein. The restraining member or mechanism further includes a securing member that passes through one or more of the plurality apertures to cause the first portion to be releasably connected to the second portion. The securing member passes through an aperture in the guide member and/or a strut assembly to pass into the end of the guide member and extend toward the proximal end. Upon moving the securing member in a proximal direction using one of a variety of different actuating mechanisms, a distal end of the securing member is removed from the apertures and the first and second both portions of the restraining member or mechanism. In this manner, the force applied to the struts to maintain a closed configuration, where the struts are retained or prevented from extending outwardly, is released from the struts, enabling them to deploy the filter.

In still another configuration, the restraining member or mechanism includes a securing member that is "sewn" through portions of the restraining member. In a similar manner to the configuration discussed above, the securing member can be removed from cooperating with the restraining member or mechanism to allow the struts to extend outwardly and deploy the filter.

In still another configuration, the restraining member or mechanism includes a plurality of channels. These channels are formed on both first and second ends of the filter in an offset configuration. The securing member can pass through one or more of the channels formed in the first side and the second side to maintain the first side in cooperative engagement with the second side. In this manner, the restraining member or mechanism applies a restraining force to the one or more struts and prevents them from extending outwardly. Upon moving the securing member in a proximal direction, a distal end of the securing member is removed from within the channels formed in the first side and second side, thereby releasing the restraining force applied by the restraining member or mechanism against the one or more struts.

In still another configuration, the restraining member or mechanism has the form of a sleeve that is adapted with one or more hoops formed therein. The wire forms a channel by maintaining a first set of hoops and second set of hoops in engagement using a securing member. By removing the securing member from engaging within one or more of the hoops, the first side and second side of the restraining member or mechanism can disengage with one another and release the restraining force that was applied to the one or more struts. In this manner, the struts are able to deploy the filter.

In yet another configuration, the restraining member or mechanism is combined with the one or more struts of the filter device. In such a configuration, two or more of the struts include tubular members adapted to receive a securing member. As the struts are brought towards each other, the lumens of the tubular members become aligned so that the securing member can pass therethrough to prevent the struts from extending outwardly or otherwise maintain the struts together or in close proximity one to another.

In still another configuration, the restraining member or mechanism is combined with the filter of the filter device. In this configuration, the filter includes at least one flap that is adapted to extend through the gap disposed between two struts. The flap(s) can be wrapped around the struts and secured to prevent the struts from extending outwardly.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 1 illustrates an exemplary filter device according to one embodiment of the present invention.

FIG. 2 illustrates an exploded perspective view of an exemplary tip of the filter device of FIG. 1.

FIG. 3 illustrates a cross-sectional side view of the exemplary tip of the filter device of FIG. 2.

FIG. 20 illustrates a partial cross-sectional view of yet another embodiment of the filter device of the present invention.

FIG. 21 illustrates a side view of a tip of the filter device of FIG. 20.

FIG. 23 illustrates a side view of yet another embodiment of a filter device with a restraining member coupled to the filter device according to another aspect of the present invention.

FIG. 24 illustrates a side view of the embodiment of FIG. 23 with the filter deployed.

FIG. 26 illustrates a perspective view of another embodiment of a filter device with a restraining member coupled to the filter device according to another aspect of the present invention.

FIG. 27 illustrates a perspective view of the restraining member of FIG. 26 before becoming coupled to the filter device according to another aspect of the present invention.

FIG. 28 illustrates a perspective view of the restraining member of FIG. 26 before becoming coupled to the filter device according to another aspect of the present invention.

FIG. 29 illustrates a perspective view of another restraining member of the filter device according to another aspect of the present invention.

FIG. 30 illustrates a perspective view of another embodiment of a filter device with a restraining member coupled to the filter device according to another aspect of the present invention.

FIG. 31 illustrates a perspective view of the restraining member of FIG. 30 before becoming coupled to the filter device according to another aspect of the present invention.

FIG. 32 illustrates a side view of the restraining member of FIG. 30 before becoming coupled to the filter device according to another aspect of the present invention.

DETAILED DESCRIPTION OF THE PREFERRED EMBODIMENTS

Figure 4A:
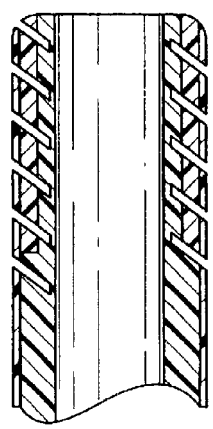
FIGS. 4A–4I illustrates various cross-sectional side views of different exemplary configurations or embodiments of the tip of the filter device of FIG. 2.

The present invention generally relates to percutaneous filter devices, systems, and methods of using the same. Embodiments of the present invention can be utilized in association with devices, systems, and methods for inserting a filter device, such as but not limited to a vascular filter device, within any blood vessel of a patient.

One or more of the embodiments of the filter devices of the present invention meet criteria for both guidewires and filter devices. For instance, it is preferable that a guidewire is steerable. Consequently, embodiments of the filter device of the present invention can be insertable within any blood vessel of a patient, such as but not limited to, coronary artery, carotid arteries, renal arteries, bypass grafts, superficial femoral artery, the arteries of the upper and lower extremities, or cerebral vasculature, and manipulated and steered by a physician to traverse the tortuous anatomy of the patient to a lesion or occlusion.

To assist the physician with the above-recited endeavor, one or more embodiments of the filter device include a shapeable, soft, distal tip. In addition, the filter device is capable of translating rotational movement or force applied to the proximal end thereof substantially equally to the distal end. In other words, with the filter device positioned within a vessel of the patient, as a physician rotates the proximal end of the filter device, the distal end of the filter device rotates substantially simultaneously with the movement of the proximal end. This is typicallydefined as having a one-to-one torqueability.

Further, the filter device of the present invention is kink resistant and is capable of receiving a variety of different coatings to improve lubricity, have anti-thrombogenic properties, and/or reduce platelet aggregation. These coatings can include, but are not limited to, a hydrophilic coating, a heparinized coating, Teflon, silicone, or other coating known to those skilled in the art in light of the teaching contained herein.

With respect to the filter of the filter device of the present invention, in one embodiment, the filter is configured to capture material of a variety of sizes and enable removal of the captured material. Therefore, filter pore sizes and shapes can be selected based upon the size of material to be captured. The material can include but is not limited to, particulates, thrombi, any atherosclerosis or plaque material dislodged during a procedure, or other foreign material that may be introduced in to the vasculature of the patient.

Referring now to FIG. 1, depicted is one embodiment of a vascular filter device, designated by reference number 10, of the present invention. As illustrated, filter device 10 includes a guide member 12 having a distal end 14 and a proximal end 16. Extending between distal end 14 and proximal end 16 of guide member 12 is a lumen 18 within which is disposed an actuating member 40 and a filter assembly 42. Distal end 14 of guide member 12 includes a tip 15 that is configured for percutaneous insertion into a blood vessel of a patient, while proximal end 16 is configured with or couples to an actuating assembly 20.

In this configuration, filter device 10 is capable of being insertable into any blood vessel of a patient or body and function as a guidewire or exchange wire for other medical components or devices, such as but not limited to catheters, stents, balloons, atherectomy devices, or other components or devices that can be exchanged using a guidewire. Further, filter device 10 can be used to filter particulates, as will be described in more detail hereinafter, thereby acting or providing embolic protection during a procedure.

Illustratively, the term "guide member" can refer to a member that is completely solid, such as a guidewire, a member that partially includes a lumen therein, or a member that includes a lumen extending from a proximal end to a distal end thereof, such as a hypo-tube. Consequently, the term "guide member" can include or encompass a guidewire or a hypo-tube that is configured to perform the functions described herein.

Guide member 12 can be fabricated from a variety of materials. For example, guide member 12 can be fabricated from Nitinol, steel, metals, metal alloys, composites, plastic, polymer, synthetic materials, or combinations thereof. Further, guide member 12 can be covered with a variety of different coatings, such as but not limited to, coatings to improve lubricity or having anti-thrombogenic properties, reduce platelet aggregation, hydrophilic coatings, a heparinized coating, Teflon, silicone, or combinations thereof.

Illustratively, guide member 12 can have an outside diameter of between about 0.010 inches to about 0.035 inches, between about 0.014 inches to about 0.018 inches, or between about 0.010 inches to about 0.018 inches. In one configuration, the outside diameter of guide member 12 is about 0.014 inches. Similarly, the diameter of lumen 18 can range from about 0.004 inches to about 0.029 inches or between about 0.008 inches to about 0.014 inches. In one configuration, the diameter of lumen 18 is about 0.008 inches.

As illustrated in FIGS. 2 and 3, the exemplary distal end 14 of guide member 12 has a step configuration, with a step portion 22 of guide member 12 having a smaller diameter than other portions of guide member 12. For ease of explanation, actuating member 40 and filter assembly 42 have been excluded from FIGS. 2 and 3.

The step portion 22 can have a variety of different configurations so long as it is adapted to couple with other portions of filter device 10. For instance, step portion 22 can include multiple steps instead of a single step as illustrated in FIG. 2. Consequently, distal end 14 of guide member 12 could include a first step portion having a first outer diameter smaller than the outer diameter of the remaining portion of guide member 12 toward proximal end 16 thereof. Further, distal end 14 of guide member 12 could include a second step portion having a smaller outer diameter than the first outer diameter of the first portion.

Attached to step portion 22 of guide member 12 is a sheath 24. Sheath 24 has a lumen 30 that extends between a distal end 26 and a proximal end 28 thereof. A portion of distal end 26 is substantially co-planar with distal end 14 of guide member 12 when sheath 24 is connected to guide member 12. Stated another way, a portion of distal end 14 of guide member 12 and distal end 26 of sheath 24 are contained within a plane that is substantially perpendicular to the longitudinal axis of lumen 18 of guide member 12 when sheath 24 is coupled, connected, or attached to guide member 12. Although this is the case in one embodiment of the present invention, one skilled in the art can identify various other configurations where this need not be the case. For instance, in an alternate configuration, distal ends 14 and 26 are not co-planar. In another configuration, portions of distal ends 14 and 26 are co-planar. In still another configuration, at least one of distal ends 14 and 26 is angularly orientated relative to the longitudinal axis of lumen 18 or lumen 30.

As illustrated in FIG. 3, distal end 26 of sheath 24, either alone or in combination with distal end 14 of guide member 12 is atraumatic. In this manner, as filter device 10 is inserted within a blood vessel filter device 10 is able to slide along the interior surface of the blood vessel and is prevented from catching upon protrusions, i.e., lesions, occlusions, stenosis, or the like, during a procedure. One skilled in the art can identify a variety of different configurations of distal ends 14 and/or 26 to perform such a desired function. For instance, the curvature of distal end 14 of guide member 12 can be varied as long as the curvature allows filter device 10 to slide along the interior surface of the blood vessel without catching upon protrusions; the curvature can be based upon distal end 14 of guide member 12 and/or the distal end of sheath 24.

Proximal end 28 of sheath 24 is configured to cooperate with a proximal end of step portion 22. Proximal end 28 of sheath 24 and the proximal end of step portion 22 are substantially parallel one to another upon coupling, connecting, or attaching sheath 24 to step portion 22. In another configuration, the proximal end of step portion 22 can include one or more raised portions within which one or more complementary recesses formed in proximal end 28 mate, or vice versa. In still another configuration, sheath 24 has a stepped configuration that allows matting with a complementary configured stepped proximal end of step portion 22, such as when step portion includes multiple steps. Various other configurations are applicable to allow sheath 24 and the remainder of guide member 12 to couple, connect, or be attached one to another.

According to another aspect of one embodiment of the present invention, sheath 24 has an outside diameter substantially the same as the outer diameter of guide member 12, while the diameter of lumen 30 is substantially the same as the outer diameter of step portion 22. Consequently, when sheath 24 is coupled to guide member 12 at step portion 22, guide member 12 has substantially the same outer diameter along its length. In other configurations, sheath 24 has a smaller or larger diameter than guide member 12.

As illustrated, sheath 24 is configured to friction fit to step portion 22. Consequently, the inner diameter of sheath 24 is configured to securely mount to step portion 22 upon slidable engagement of sheath 24 and step portion 22. In other configurations, sheath 24 can be affixed to step portion 22 with an adhesive, such as but not limited to, any medical grade adhesive, UV curable adhesive, or other adhesive that cause sheath 24 to securely connect to step portion 22. In still another configuration, sheath 24 can be press fit, soldered, mechanical attached, or coupled to guide member 12 using any other mechanism that causes sheath 24 to be securely connected to step portion 22. In still other configurations, sheath 24 and step portion 22 have a key configuration where sheath 24 includes at least one key and step portion 22 includes at least one key way to receive the at least one key, or vice versa.

In general, sheath 24 can be fabricated from a variety of different materials and have a variety of different configurations. For example, sheath 24 can be fabricated from steel, titanium, platinum, metals, metal alloys, composites, plastics, polymers, synthetic materials, or combinations thereof. Further, sheath 24 can include means for radiopacity. Additionally, sheath 24 can be fabricated from (i) a radiopaque substance, (ii) a non-radiopaque substance and coated with a radiopaque substance, or (iii) a non-radiopaque substance doped with a radiopaque substance. The radiopaque substances can include, but not limited to, barium sulphate, bismuth subcarbonate, titanium dioxide, combinations thereof, or other radiopaque substances. In still another configuration, sheath 24 can include one or more markers that have radiopaque characteristics. These markers can be fabricated from a radiopaque material, whether the material is radiopaque, a non-radiopaque material coated with a radiopaque material, or a non-radiopaque materials doped with a radiopaque material. Consequently, sheath 24 can include means for radiopacity, whether such means results from the materials forming sheath 24 or from attaching, coupling, or connecting markers, bands, or other indicators having radiopaque properties or characteristics.

Disposed over sheath 24 and optionally a portion of guide member 12 is cover 32. Cover 32 is configured to seal and secure sheath 24 to guide member 12. Consequently, cover 32 acts as a means for securing sheath 24 to guide member 12. In one embodiment, cover 32 is a thin walled plastic heat shrink tubing or silicon tubing. In other configurations, interference fit or compression fit plastics, polymers, synthetic materials, or silicon can be used that need not be heat shrunk. In general, cover 32 can be a medical grade synthetic material.

According to another aspect of the present invention, distal end 14 of guide member 12, distal end 26 of sheath 24, and/or the distal end of cover 32 can be configured, collectively, to form a bullet nose or have a curved profile. This can be in addition to or alternatively from only distal end 14 of guide member 12 and/or distal end 26 of sheath 24 being curved or being atraumatic.

Collectively, distal end 14 of guide member 12, sheath 24, and cover 32 form tip 15 of filter device 10. Although this is one configuration, one skilled in the art can appreciate that tip 15 can be formed solely from or any combination of guide member 12, sheath 24, and cover 32.

To provide flexibility to tip 15 of filter device 10, embodiments of the present invention may include one or more grooves 34 that extend entirely or partially through one or more of distal end 14 of guide member 12, sheath 24, and cover 32, as illustrated in FIGS. 4A-4I. The flexibility of tip 15 allows a physician or clinician to shape the tip and enable the guide member to be steered during a procedure.

Consequently, the tip may maintain a level of resiliency so that a curvature defined by the physician or clinician is maintained during movement of the guide member through the tortuous anatomy of a patient.

The term "groove" includes one or more cuts or slits that partially or completely extend through a portion of filter device 10, optionally including the sleeve and the securing member. Further, the term "groove" includes one or more cuts or slits that partially or completely surrounds a portion of filter device 10, whether or not such one or more cuts or slits extend completely or partially through one or more of the guide member, the sleeve, or the securing member.

Each groove 34 can have a variety of different configurations, such as but not limited to straight, helical, geometric, or combinations thereof. For instance, a single groove 34 can extend around all or a portion of tip 15 and optionally extend into the remainder of filter device 10. Further, any number of grooves 34 can be included in tip 15 of filter device 10 depending upon the degree of flexibility needed for a procedure. For example, the more grooves 34 included in tip 15 of filter device 10, the greater the flexibility. Similarly, the depth of each groove 34 can vary depending upon the flexibility desired. For instance, the deeper grooves 34 the greater the flexibility of tip 15 of filter device 10. Similarly, difference in the configuration of each groove 34 can affect the flexibility of tip 15 of filter device 10. For instance, the steeper the sides of grooves 34, the less flexibility of tip 15.

Figure 4B:
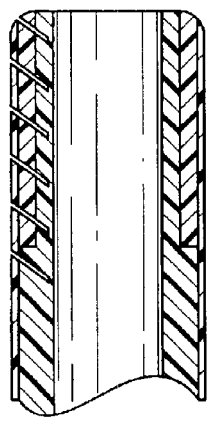

As illustrated in FIGS. 4A–4I, grooves 34 can be disposed along the longitudinal length of tip 15 of filter device 10 equally, gradually, continuously, periodically, or combinations thereof. For instance, as shown in FIG. 4A, tip 15 includes a single helical groove 34 that has an equal pitch along the length of tip 15, while FIG. 4B depicts a single helical groove 34 that has a gradually increasing pitch along the length of tip 15. Although not shown, it can be understood that tip 15 can include a single helical groove 34 that has a gradually decreasing pitch along the length of tip 15 from the proximal end to the distal end thereof.

Figure 4C:
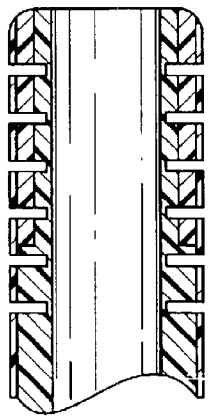
Figure 4D:
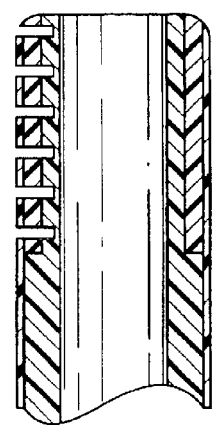

As shown in FIG. 4C, tip 15 can have a plurality of individual grooves 34 disposed along the length of tip 15. It can be understood that each groove 34 need not encircle tip 15 of guide member 12; rather, each groove 34 can partially encircle tip 15 of guide member 12, as depicted illustratively in FIG. 4D.

Figure 4E:
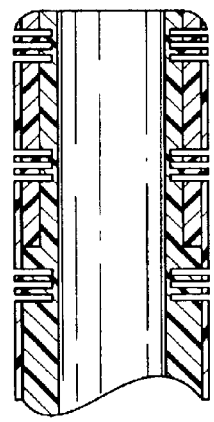

FIG. 4E depicts a configuration of tip 15 where groupings of grooves 34, whether straight, helical, or geometric, are disposed at different portions of tip 15.

Figure 4F:
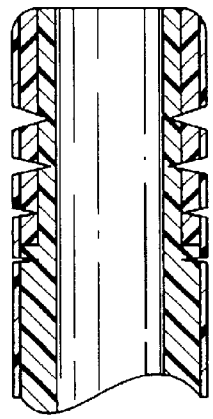

FIG. 4F depicts a configuration where grooves 34 are large and have shallow sides, i.e., the angle between the axis of the groove that passes through the apex of the groove and the side of the groove is large. In the alternative, each groove 34 can be small and have steep sides, i.e., the angle between the axis of the groove that passes through the apex of the groove and the side of the groove is small.

Figure 4G:
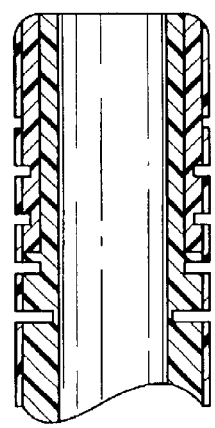

FIG. 4G illustrates a configuration of tip 15 of filter device 10 where the pitch between adjacent grooves is increasing from the proximal end to the distal end of tip 15 and the depth of each groove 34 varies, i.e., each groove 34 need not extend the entire depth of tip 15 of filter device 10.

Figure 4H:
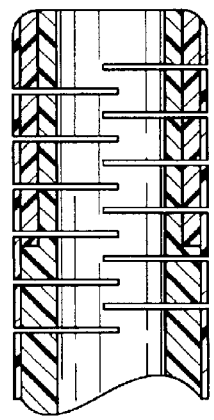
Figure 4I:
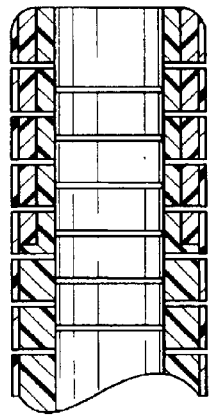

FIG. 4H illustrates a configuration of tip 15 of filter device 10 wherein grooves 34 are straight and extend into lumen 18, while FIG. 4I illustrates a configuration where grooves 34 are helical and extend from the exterior of tip 15 to lumen 18.

The above described configurations of the grooves with tip 15 of filter device 10 are only illustrative and should not be considered as limiting the applicability of other configurations as known by one skilled in the art in light of the teaching contained herein. For instance, grooves 34 can pass through securing member 32, sleeve 24, and terminate in guide member 12, can pass through sleeve 24 and terminate in guide member 12, be contained solely in guide member 12, combinations thereof, or the like.

Generally, grooves 34 can be formed in tip 15 of filter device 10 using a variety of different techniques, such as but not limited to, micro-machining, grinding, etching, laser cutting, abrasive water jet, electrical discharge machine, or the like. Further, grooves 34 can have a pitch of between about 0.015 inches to about 0.100 inches, from about 0.020 inches to about 0.060 inches, or from about 0.025 inches to about 0.050 inches.

Figure 5:
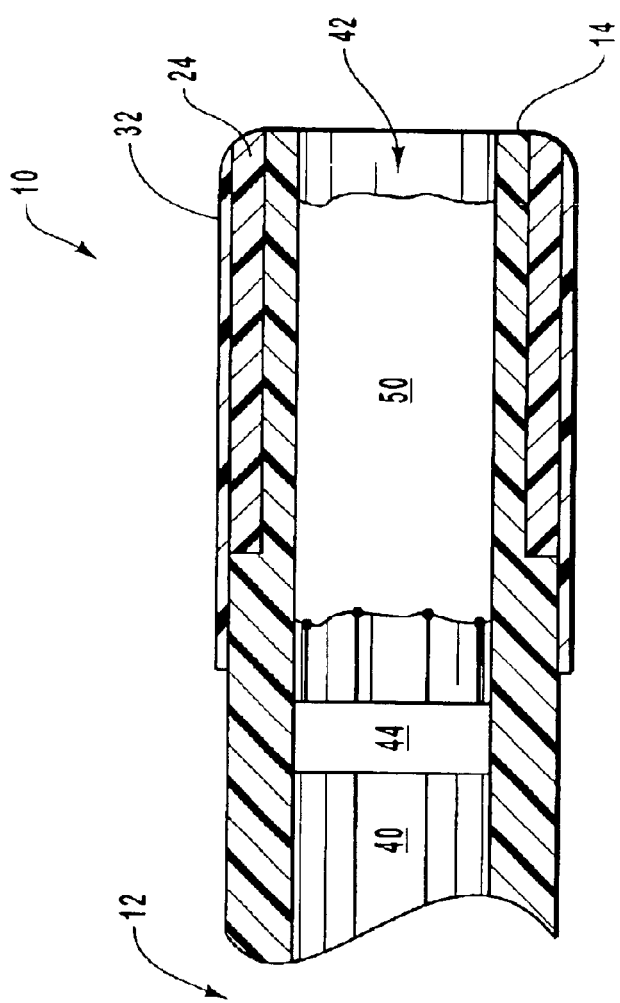
FIG. 5 illustrates a cross-sectional side view of the tip of the filter device of FIG. 2 with exemplary actuating member and filter assembly in a closed position.

Referring now to FIG. 5, depicted is a partial cross-sectional view of a lumen 18 of guide member 12. Disposed within lumen 18 of guide member 12 are an actuating member 40 and a filter assembly 42. Actuating member 40 forms part of actuating assembly 20 and is adapted to deploy and partially or completely retract filter assembly 42. Additionally, actuating member 40 provides structural support to filter device 10 and assists with preventing kinking of filter device 10.

The actuating member 40 extends toward a proximal end 16 of filter device 10. As illustrated, the distal end of actuating member 40 includes a head 44. Head 44 has a generally cylindrical form and is configured to create a seal between actuating member 40 and the interior walls of lumen 18. In other embodiments of the present invention, the remainder of actuating member 40 is configured to create a seal between actuating member 40 and the interior walls of lumen 18. Alternatively, actuating member 40 and head 44 are not configured to create a seal with the interior walls of lumen 18, rather a separate seal, such as but not limited to, one or more O-rings, quad-rings, V-rings, gaskets, combinations thereof or other structure capable of creating a seals is mounted to head 44 to create a seal between the interior wall of lumen 18 and head 44.

The head 44 of actuating member 40 cooperates or engages with filter assembly 42 and forces filter assembly 42 from the distal end of lumen 18 as actuating member 40 is moved during a procedure. By so doing, a filter 50 of filter assembly 42 is deployed to collect material. Further, head 44 can be moved within lumen 18 by actuating member 40 to retrieve filter assembly 42, thereby aiding with removal of the collected material subsequent to a procedure or to allow for repositioning of filter 50 of filter assembly 42. The head 44 and actuating member 40 can have various other configurations so long as actuating member 40 is capable of deploying and retrieving filter assembly 42. For instance, in another configuration, actuating member 40 can be devoid of head 44 and be formed from a plurality of wires, strands, or members that are braided together, connected to, or formed as part of filter assembly 42.

Actuating member 40 and head 44 can be fabricated from a variety of different materials, such as but not limited to, stainless steel, tungsten, titanium, platinum, Nitinol, other metals, alloys thereof, composites, plastics, polymers, synthetic materials, D or combinations thereof.

Figure 6A:
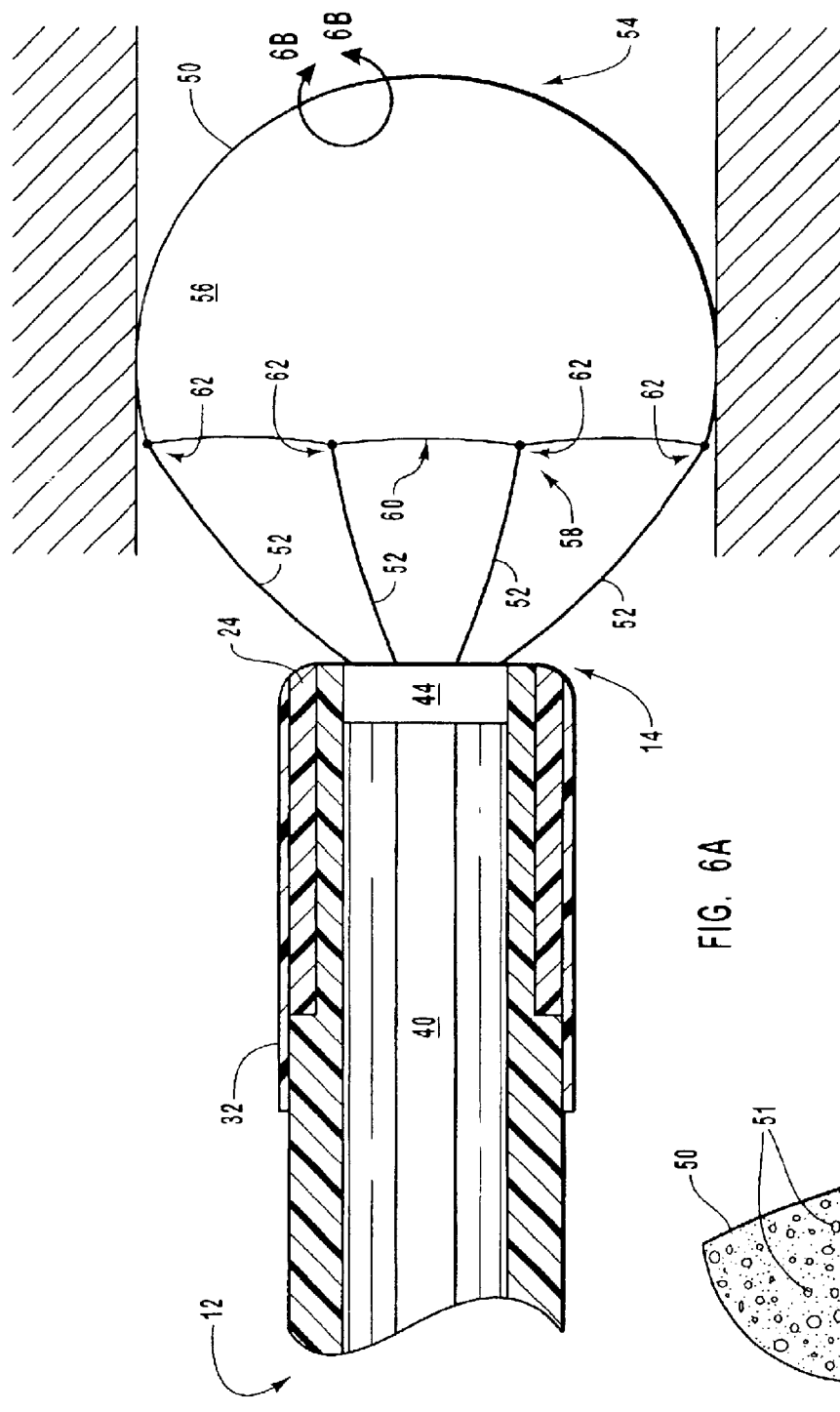
FIG. 6a illustrates a cross-sectional side view of the tip of the filter device of FIG. 2 with exemplary actuating member and filter assembly in an actuated position.
Figure 6B:
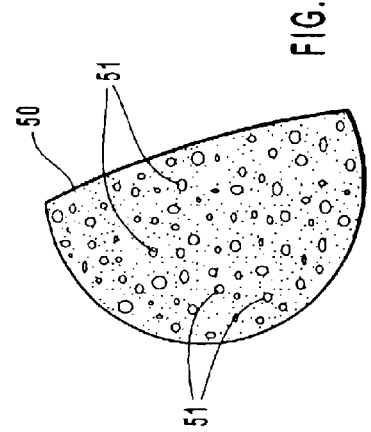
FIG. 6b illustrates one or more pores of the filter of the filter device of the present invention.

Referring now to FIG. 6a and 6b, depicted is filter assembly 42 in a deployed position following movement of actuating member 40 in the distal direction. As illustrated, filter assembly 42 includes filter 50 and a plurality of radially spaced-apart struts 52 extending from filter 50 to head 44 of actuating member 40. Filter 50 has a distal end 54 separated from a proximal end 58 by an intermediate portion 56. A peripheral edge of proximal end 58 is secured to struts 52 to form an opening 60 that allows material to flow into filter 50, while distal end 54 is closed to prevent material from escaping or exiting from filter 50.

Although in one configuration filter is hemispherical, it can be understood that filter 50 can be a variety of configurations, such as but not limited to, hemispherical, conical, cylindrical, combinations thereof, or any other configuration that allows for material to be collected therein, while the opening of the filter substantially extends to the peripheral surface of the blood vessel within which the filter is disposed. More generally, filter 50 can have any configuration so long as proximal end 58 has an opening that allows material to flow into filter 50 and distal end 54 is closed to prevent material from escaping or exiting from filter 50.

Figure 7:
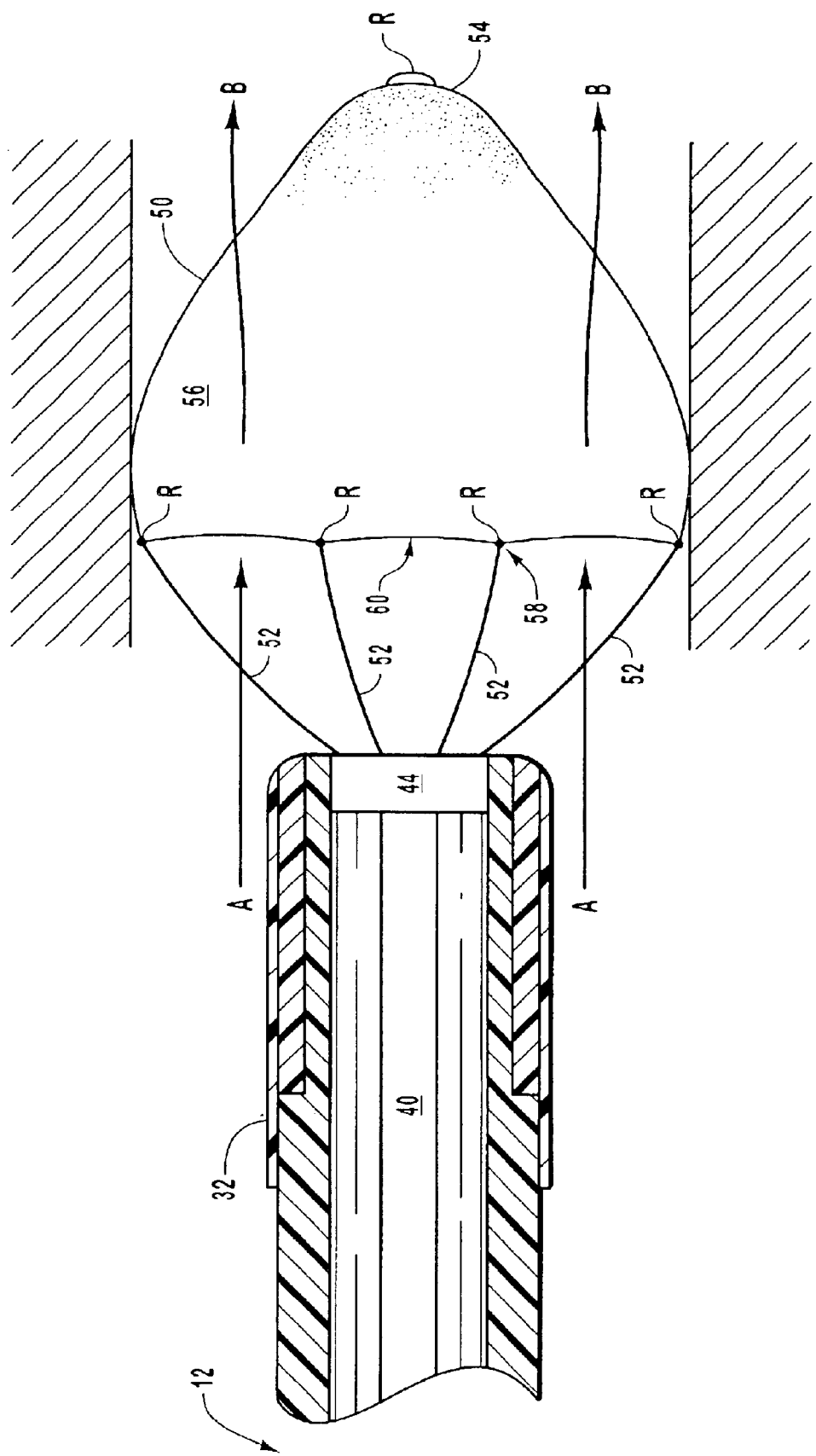
FIG. 7 illustrates a cross-sectional side view of the tip of the filter device of FIG. 2 with exemplary actuating member and filter assembly in an actuated position and a portion of the filter filled with material.

Intermediate portion 56 and distal end 54 are free to float in the blood flow or stream within the blood vessel, while proximal end 58 is in a fixed relationship with actuating member 40 through struts 52. By allowing intermediate portion 56 and distal end 54 of filter 50 to float, as filter collects material, such as illustrated in FIG. 7, the material creates drag on filter 50 so that the shape of filter 50 changes, while maintaining substantially the same volume as when deployed. Consequently, blood can continue to flow through portions of intermediate portion 56 as distal end 54 continues to fill with material, as indicated by arrows A and B in FIG. 7. In this manner, material can be collected as blood flow is maintained through filter 50.

Filter 50 can be fabricated from a variety of different materials, such as but not limited to, a woven or braided plastic or metallic mesh, a perforated polymer film, a Nitinol mesh, combinations thereof, or other material that is capable of capturing material within flowing blood, while allowing the blood to flow through the pores or apertures thereof. Generally, filter 50 can be fabricated from a variety of materials so long as filter 50 is capable of being packed within lumen 18, floating in the blood flow or stream passing through the blood vessel within which it is inserted, and is bio-compatible.

Filter 50 can have a variety of differently sized pores 51 ranging from about 50 microns to about 200 microns, from about 60 microns to about 180 microns, or from about 75 microns to about 150 microns. For instance, as illustrated in FIG. 6b, pores 51 can have a variety of different configurations, such as but not limited to circular, oval, polygonal, combinations thereof or other configurations known to one skilled in the art in light of the teaching contained herein. In one configuration, therefore, filter 50 can includes pores that are differently sized and configured. Consequently, a major or minor axis of each pore can have a variety of different sizes ranging from about 50 microns to about 200 microns, from about 60 microns to about 180 microns, or from about 75 microns to about 150 microns. Generally, the pore size can vary as needed, so long as the pores are sized so that the pores do not compromise blood flow through the filter, i.e., prevent blood flowing through the filter, and collect material that could potentially occlude smaller downstream vessels, potentially blocking blood flow to tissue or result in stroke or infarction.

In addition to the above, filter 50 can be coated with a hydrophilic coating, a heparinized coating, Teflon, silicone, combinations thereof, or various other coatings as know or desired by one skilled in the art in light of the teaching contained herein.

Referring again to FIG. 6a, connecting filter 50 to head 44, and optionally directly to actuating member 40, are struts 52. As illustrated, the distal ends of struts 52 are connected at radially spaced-apart locations about the peripheral edge of proximal end 58 of filter 50. The struts 52 attach to filter 50 on the exterior of filter 50, on the interior of filter 50, along the edge of filter 50, through filter 50, or combinations of one or more of the above. The struts 52 can be attached to filter 50 and/or actuating member 40 by medical grade adhesives, such as but not limited to, ultra violet curable adhesives, acrylics, cyanoacrylates, solvent bonding, radio frequency or ultrasonic bonding, or some other manner to securely connect the distal end of one or more struts 52 to filter 50. Alternatively, struts 52 can be thermally bonded to filter 50 and/or actuating member 40, such as when struts 52 are fabricated from a material allowing such thermal bonding. In another configuration, struts 52 are woven into filter 50 or are distally formed with hooks or loops that are can be used to attach struts 52 to filter 50. In still another configuration, struts 52 can be lengthened strands of filter 50 that extend from filter 50 to actuating member 40. In still another configuration, struts 52 are extensions or strands of actuating member 40, such as when actuating member 40 is a braided wire, a slit tube, or other member that is capable of performing the functions described herein with respect to actuating member 40. In still another configuration, struts 52 are extensions of filter 50 that extend to head 44 and connect thereto.

As illustrated, each strut 52 is formed from Nitinol, stainless steel, metals, alloys, composites, plastics, polymers, synthetic materials, combinations thereof, or other materials that allow struts to perform one or more of the functions described herein. Each strut 52 can have a generally curved distal portion 62 and may be biased to extend radially outward when filter 52 is to be deployed. In this manner, distal portion 62 is in close proximity to the wall of the blood vessel within which filter device 10 is inserted when deployed. The struts 52 extend the edge of proximal end 58 of filter 50 into contact with the wall of the blood vessel. By so doing, the proximal end 58 of filter 50 can contact a substantial portion of the wall of the blood vessel and accommodate for variations in the profile of the wall.

Although, reference is made to the edge of proximal end 58 contacting the blood vessel, other configurations of the present invention locate the edge of proximal end 58 adjacent to, in close proximity to, juxtaposed, or contiguous with the wall of the blood vessel. This can be the case, so long as material can be captured through opening 60 and material is not captured between the outer surface of filter 50 and the wall of the blood vessel within which filter device 10 is inserted.

Figure 8:
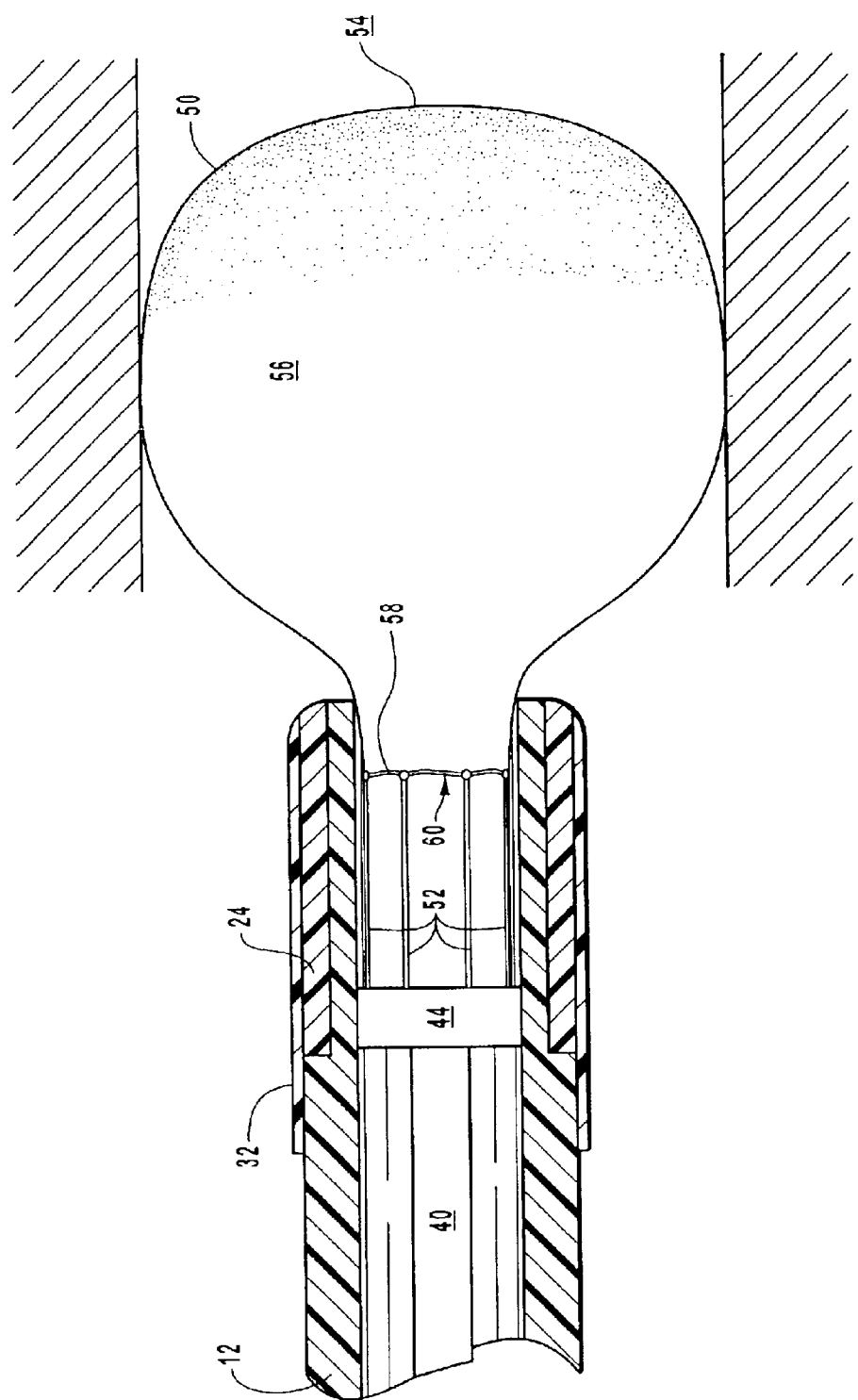
FIG. 8 illustrates a cross-sectional side view of the tip of the filter device of FIG. 2 with exemplary actuating member and filter assembly in a retracted position.

Referring now to FIG. 8, depicted is filter 50 in the captured or retrieved position. When actuating member 40 is moved in the proximal direction, opening 60 of filter 50 is drawn toward distal end 14 of guide member 12. As actuating member 40 is moved in the proximal direction, the interior wall of lumen 18 forces struts 52 inwardly. Simultaneously, distal end 62 of each strut 52 moves inwardly to close opening 60. This simultaneous motion prevents material trapped within the interior of filter 50 from escaping. Opening 60 can alternatively be substantially completely closed following the initial movement of actuator member 40 in the proximal direction. In still another configuration, opening 60 can be partially closed as actuator member 40 is moved in the proximal direction and gradually becomes substantially completely closed upon a substantial portion of struts 52 being retracted into lumen 18 of filter device 10. In still another configuration, opening 60 can be substantially completely closed upon a portion of struts 52 being retracted into lumen 18 of filter device 10.

Figure 9:
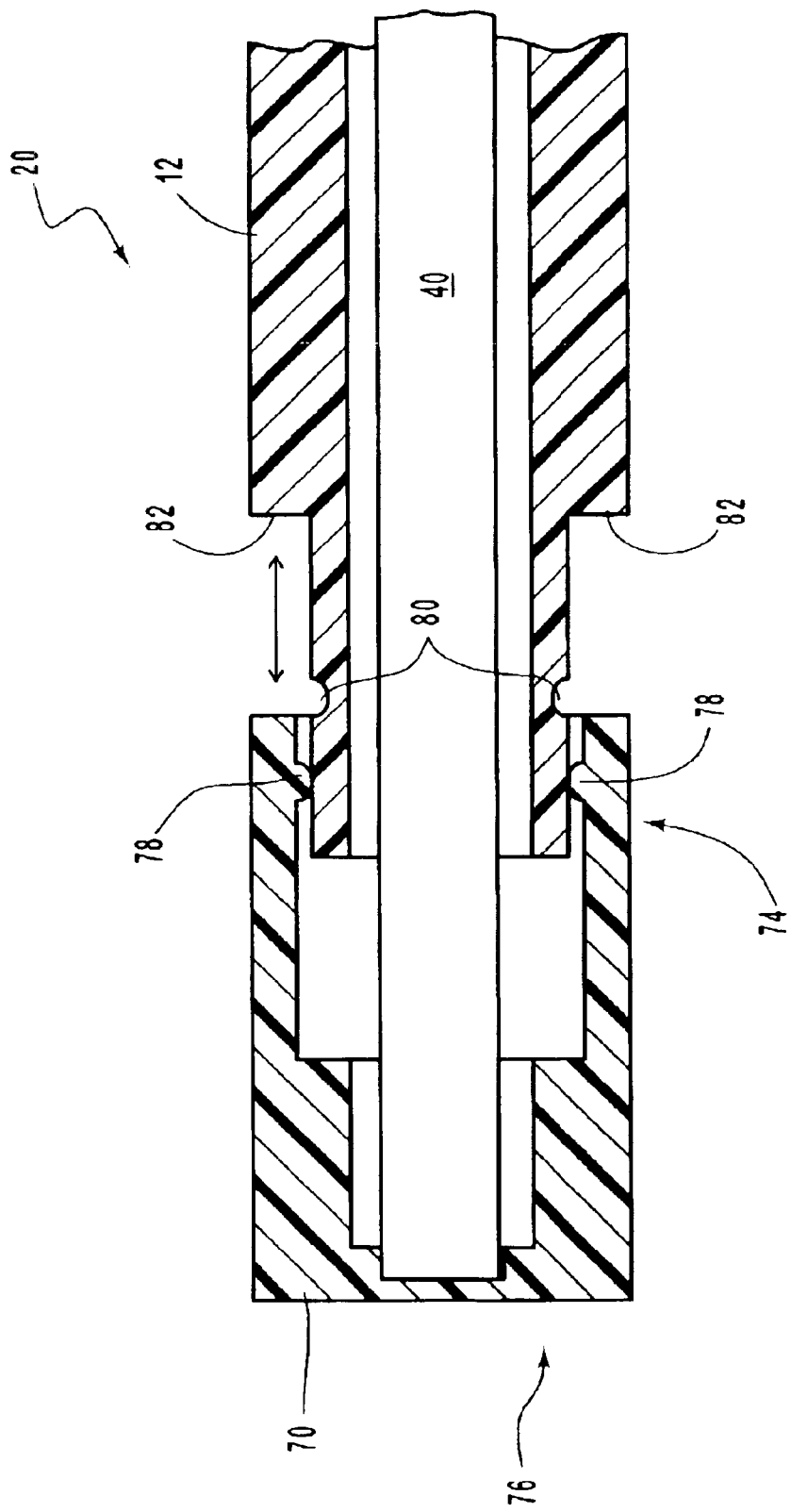
FIG. 9 illustrates a cross-sectional side view of an exemplary actuating assembly of the filter device of FIG. 2.

To move actuating member 40 in the proximal direction and/or distal direction filter device 10 includes an actuating assembly 20. The actuating assembly 20 can be integrated with guide member 12 and/or separate therefrom. With reference to FIG. 9, depicted in an illustrative configuration of actuating assembly 20.

Referring now to FIG. 9, depicted is an exemplary embodiment of an actuating assembly 20 that can be used to manipulate actuating member 40. Through operating actuating assembly 20, filter assembly 42 (FIG. 5) can be deployed and retrieved.

As illustrated, actuating assembly 20 includes an actuating element 70 and actuator member 40. Actuating element 70 includes a distal end 74 that is configured to cooperate with guide member 12, while a proximal end 76 of actuating element 70 is attached to proximal end 16 of guide member 12. The distal end 74 has a step configuration and includes indentations 78 that are configured to cooperate with complementary protrusions 80 formed in guide member 12. As actuating element 70 is moved in the distal direction, indentations 78 and protrusions 80 mate to position actuating element 70 in a desired location relative to proximal end 16 of guide member 12, thereby positioning filter assembly 42 in a selected position, such as in the retracted position illustrated in FIG. 9.

As actuating element 70 is continually moved in the distal direction, distal end 74 meets a wall 82 formed in guide member 12 that prevents further movement in the distal direction. Through this configuration, actuating element 70 is prevented from excessive longitudinal displacement in the distal direction. This stopping of the longitudinal displacement of actuating element 70 indicates that filter assembly 42 is deployed.

Although reference is made to one manner to indicate the particular location filter assembly 42, one skilled in the art can identify a variety of different manners. For instance, a plurality of indentations and/or protrusions can be included within actuating element 70 and guide member 12 to control the distance which actuating element 70 and consequently filter assembly 42 is moved. In another configuration, a wall formed in actuating element 70 mates with the distal end of guide member 12 to prevent excessive longitudinal displacement in the distal direction. In still another configuration, a combination of walls in actuating element 70 and guide member 12 can be used. In still another configuration, distal end 76 of actuating element 70 is tapered and cooperates with a taper formed in proximal end 16 of guide member 12. The complementary tapers control the longitudinal displacement of actuating element 70 relative to proximal end 16 of guide member 12. In still other configurations, a combination of indentations, protrusions, walls, or tapers can be used. Various other manners are known to control the distance traveled by actuator element 70 while indicating the position of filter assembly 42.

Figure 10:
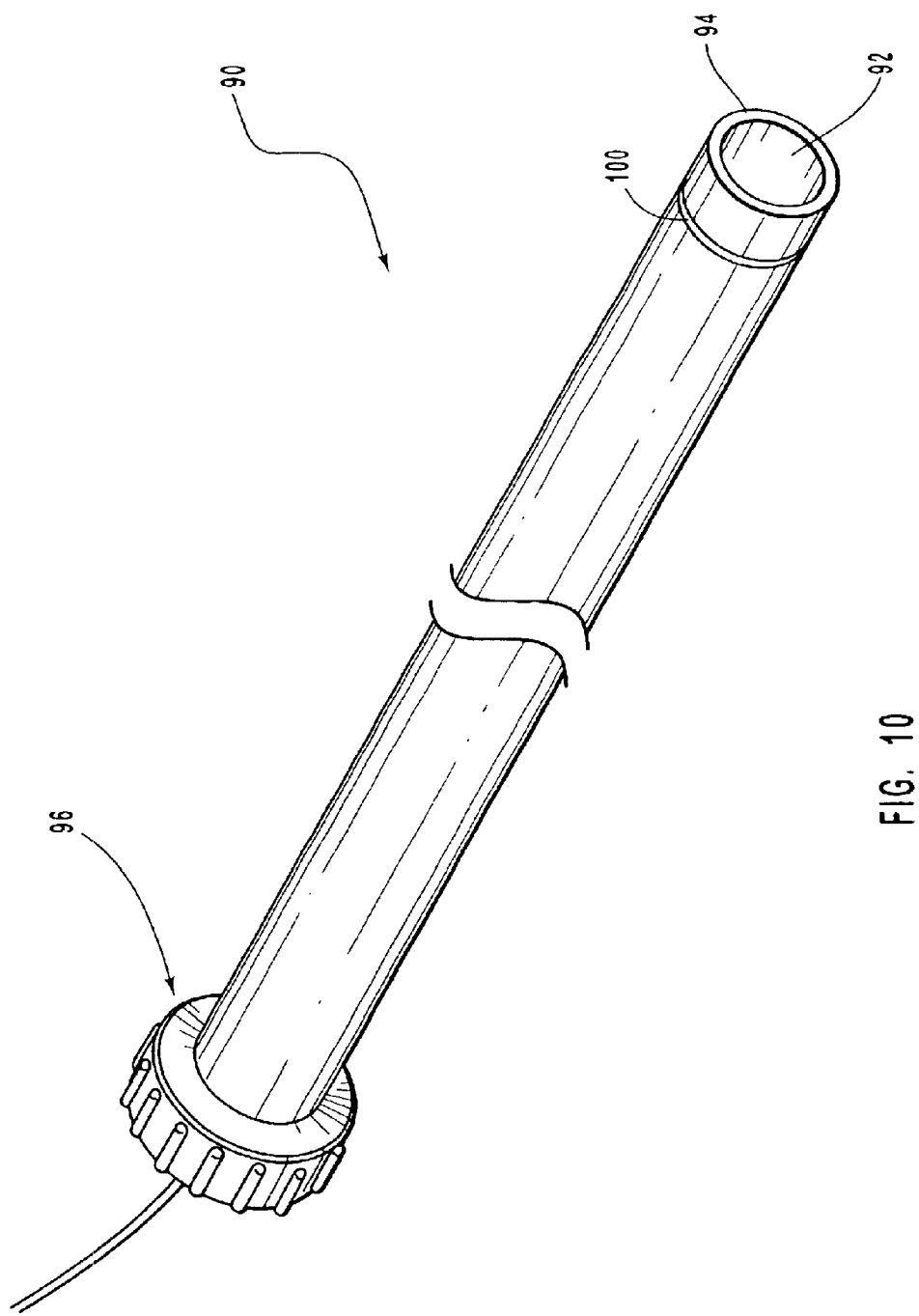
FIG. 10 illustrates a perspective view of one exemplary capture catheter adapted for use with the filter device of the present invention.

To remove filter device 10 from within the patient, embodiments of the present invention provide a capture catheter 90, as shown in FIG. 10. Capture catheter 90 is adapted to enclose filter 50 to prevent filter from tearing or catching on stents, grafts, other implants, guide members, catheters, sheaths, or other protrusions that may be encountered as filter 50 is removed from the patient.

Figure 11:
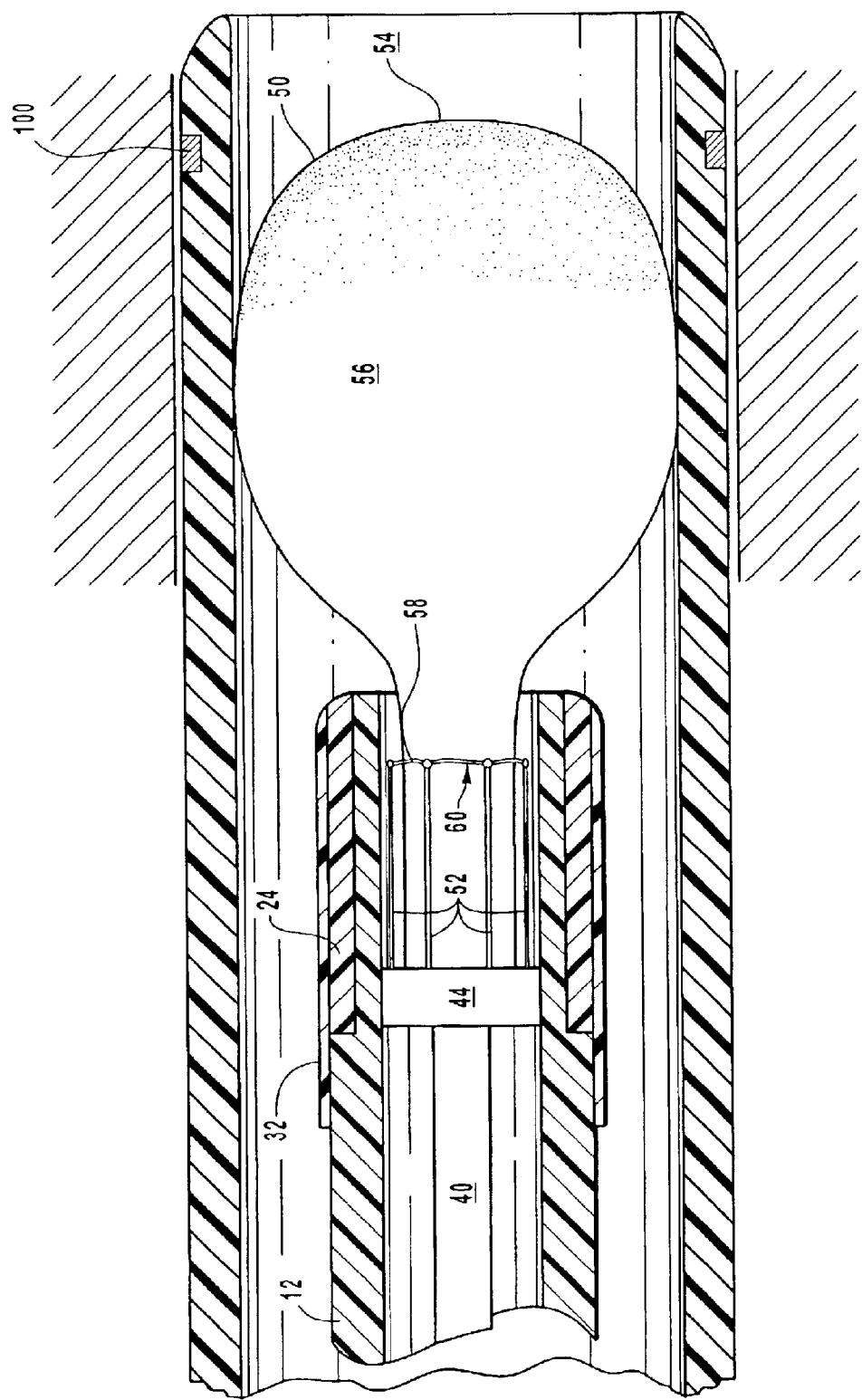
FIG. 11 illustrates a cross-sectional side view of the actuating member and filter assembly in a retracted position with the capture catheter in position surrounding the filter of the filter device of FIG. 2.

As illustrated in FIG. 10, capture catheter 90 has a generally elongate form having a lumen 92 extending from a distal end 94 to a proximal end 96 thereof. Disposed at distal end 94 is at least one radiopaque marker or band 100 that aids a physician or clinician in placing capture catheter 90 in the desired location relative to filter 50, as illustrated in FIG. 11. Through viewing the insertion of capture catheter 90 through a fluoroscope, a physician or clinician can place distal end 94 to surround filter 50.

The lumen 92 of capture catheter 90 is adapted to receive filter 50 and substantially completely enclose filter 50. The inside diameter of lumen 92 is configured to engage with struts 52 when they are in the open configuration, i.e., filter 50 is in the deployed position, and push struts 52 radially together to close opening 60. Through this configuration, opening 60 is closed before distal end 94 of capture catheter 90 contacts filter 50 and the engagement of capture catheter 90 with filter 50 does not cause embolic material to escape from within filter 50.

As capture catheter 90 is advanced over filter 50, it is compressed into lumen 92 of capture catheter 90. To limit the amount of compression of the embolic material within filter 50, a section of lumen 92 which or that optionally has greater elasticity than the remainder of capture catheter 90, the border of this section being represented by dotted lines in FIG. 10. By so doing, this portion of capture catheter 90 can expand around filter 50 and any captured embolic material.

Capture catheter 90 can have various configurations and be fabricated from a variety of different materials. For example, capture catheter 90 can be fabricated from metals, alloys, plastics, polymers, synthetic materials, composites, or other medical grade materials. Further, capture catheter 90 can be kink resistant, biocompatible, radiopaque, in whole or in part, and capable of being exchanged over guide member 12. Additionally, the elasticity of capture catheter 90 can be constant along its length, variable along its length, constant along a portion and variable along another portion of capture catheter 90, or combinations thereof.

As illustrated in FIG. 10, disposed at proximal end 96 of capture catheter 90 is a locking mechanism 98. The locking mechanism 98 engages with the proximal end of guide member 12 to securely capture guide member 12 when distal end 94 partially or completely surrounds filter 50 (FIG. 11). In one configuration, locking mechanism 98 is an annular clamp that can be rotated to clamp a proximal end of guide member 12. In another configuration, locking mechanism 98 can be a rotating hemostatis valve through which is disposed the proximal end of guide member 12. In still another configuration, locking mechanism 98 can be a locking jaw-set, such as a mechanical collett. Each of these locking mechanisms can be configured in a variety of different manners and fabricated from a variety of different materials as known to those skilled in the art. For instance, the locking mechanism can be fabricated from plastics, polymers, metals, synthetic materials, alloys, or various other materials.

According to another aspect of the present invention, filter device 10 is generally used with a fluoroscope that enables a physician to view the insertion of filter device 10 through the tortuous anatomy of a patient. To enable filter device 10 to be visible to the physician, filter device 10 includes radiopaque bands, markers, or other means for radiopacity that provide reference points for the physician. With reference to FIG. 7, various locations are illustrated as being radiopaque by reference letter R. As shown, tip 15 of filter device 10 is radiopaque. More specifically, the most distal portion of distal end 14 is radiopaque so that the physician knows the location of tip 15 of filter device 10.

The distal end of actuating member 40 is radiopaque so that the physician knows a (D, A, OA whether filter assembly 42 is in the stored, deployed, or retrieved position, while distal end 54 of filter 50 includes a radiopaque marker that defines the most distal portion of filter device 10. Similarly, capture catheter 90 can include radiopaque bands, other markers, or means for radiopacity to define the distal end thereof.

In addition to the distal ends of guide member 12, capture catheter 90, actuating member 40, and filter 50, embodiments of the present invention include radiopaque markers or other means for radiopacity at the junction of struts 52 and proximal end 58 of filter 50. In this manner, a physician can view the location of opening 60 during the procedure and verify that opening 60 is closed before the physician retrieves filter device 10 when the procedure is completed.

Although reference is made to placing radiopaque bands or markers at various locations on the components of filter device 10, one skilled in the art can identify various other locations where radiopaque bands, markers, or other means for radiopacity are appropriate. Further, embodiments of the present invention need not include all discussed radiopaque bands or markers, but rather can include one or more of the described radiopaque bands or markers as desired.

Following hereinafter is a discussion of an illustrative manner by which a filter device of one embodiment of present invention is inserted into a carotid artery. Although reference is made to the present invention being inserted into a carotid artery, it can be understood by one skilled in the art that different methods can by used to insert the filter device of the present invention into any blood vessel within a patient.

With reference to FIGS. 12–17, initially, a small needle is used to gain femoral access, as represented by block 110. This small hole is subsequently dilated until the hole is large enough to allow the insertion of an introducer of appropriate size as known to one skilled in the art.

Figure 13:
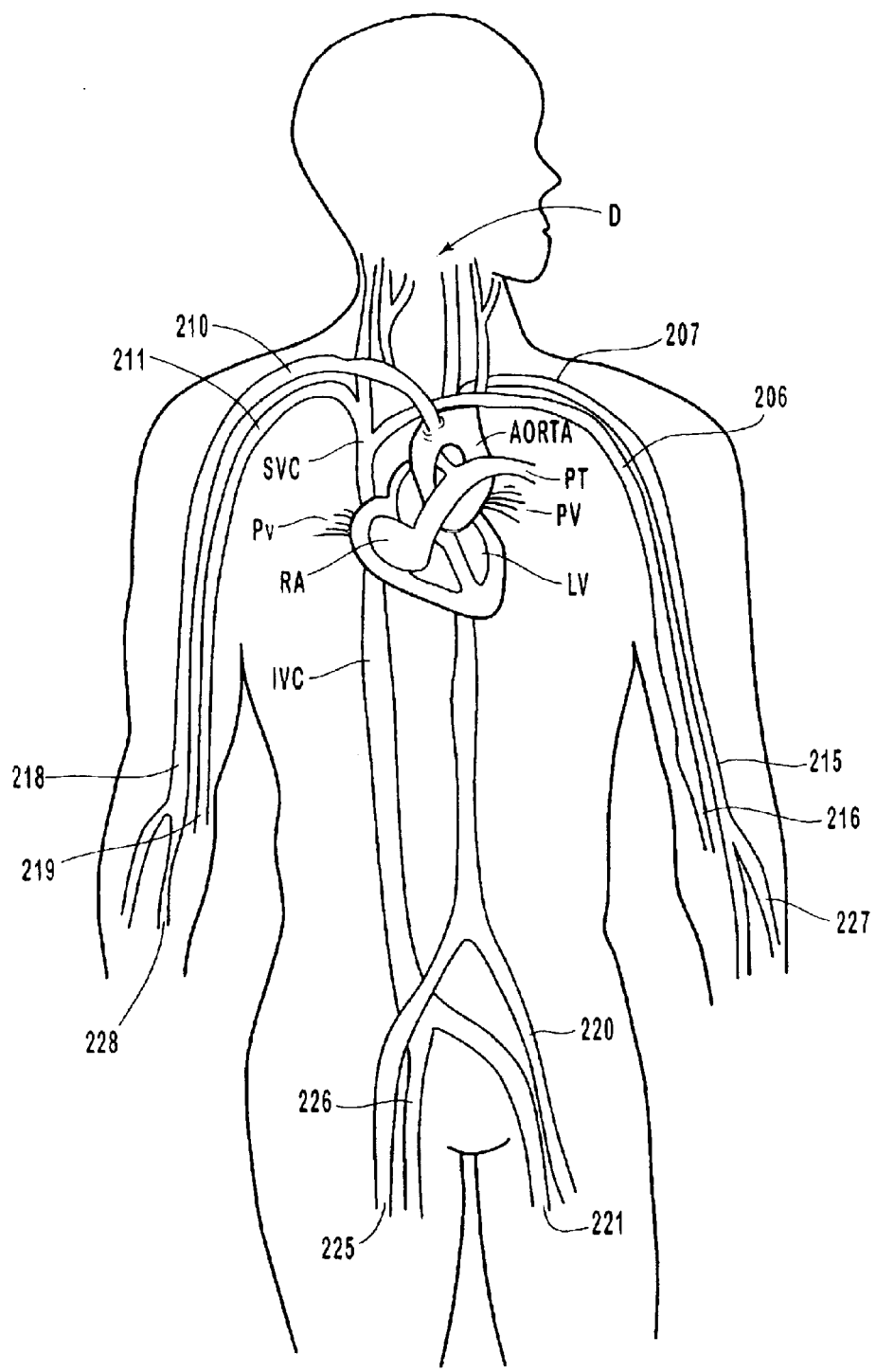
FIG. 13 illustrates a portion of the vasculature of an individual within which the filter device of FIG. 2 can be inserted.
Figure 14:
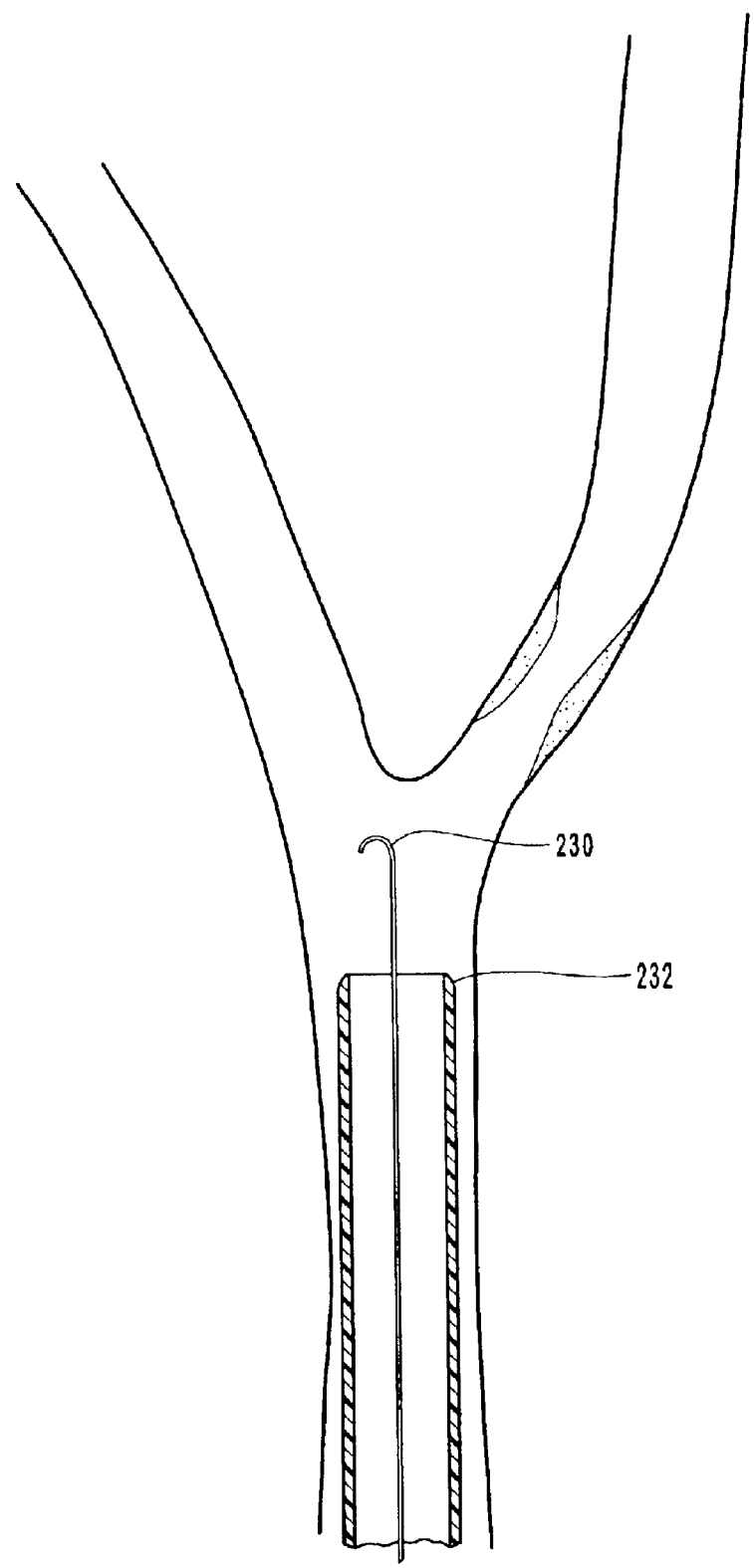
FIG. 14 illustrates a lesion formed in the interior carotid artery of the individual of FIG. 13.

With reference to FIG. 13, it can be understood by one skilled in the art, that a variety of different access sites can be used. For example, the right subclavian artery 210, left subclavian artery 206, right brachial artery 218, left brachial artery 215, right femoral artery 225, left femoral artery 220, right radial artery and left radial arteries 227, 228, or any other artery as known by one skilled in the art can be used to enter a patient's arterial circulation. Alternatively, as known by one skilled in the art, any other blood vessel selectable by the physician can be chosen as an access site.

Referring now to FIGS. 12–17, following insertion of the introducer, a guidewire 230 is inserted into the femoral access site and steered, under fluoroscopy, to the desired location in the arterial system, just proximal to the lesion to be treated, as represented by block 112. In this illustrative example, the following discussion relates to stenting of a lesion in the internal carotid artery, as referenced by arrow D in FIG. 12 and illustrated in FIG. 13.

Figure 12:
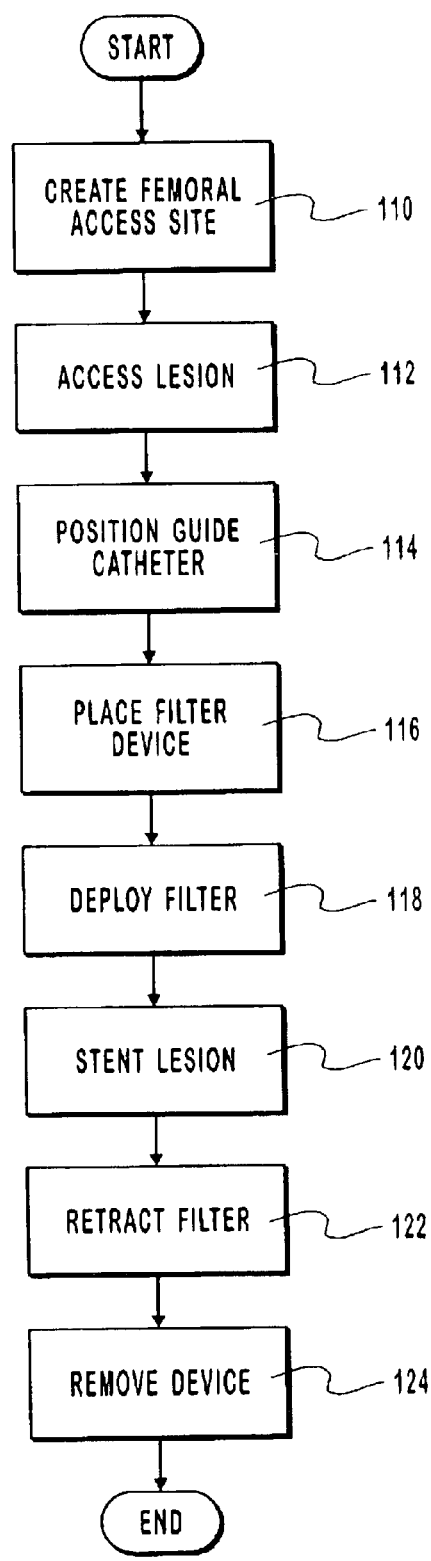
FIG. 12 illustrates a flow diagram of an exemplary method for using the filter device of FIG. 2.

Guidewire 230 and guide catheter 232 are advanced together incrementally until the distal tip of guidewire 230 is placed proximal to the lesion, as represented by block 114 and shown in FIG. 12. Upon placing guide catheter 232, guidewire 230 is removed and filter device 10 is advanced through guide catheter 232, as represented by block 116 and illustrated in FIG. 14.

The filter device 10 is carefully advanced through the lesion to a point distal to the lesion and subsequently acts as an exchange guidewire with a filter attached. Alternatively, filter device 10 can function as guide member 230 so that a physician need not exchange filter device 10 for guidewire 230. In such a configuration, the steps of placing the filter device and accessing the lesion can be performed simultaneously. This particular configuration is useful because it limited the number of exchanges performed by the physician and consequently accelerates the performance of the procedure.

Figure 15:
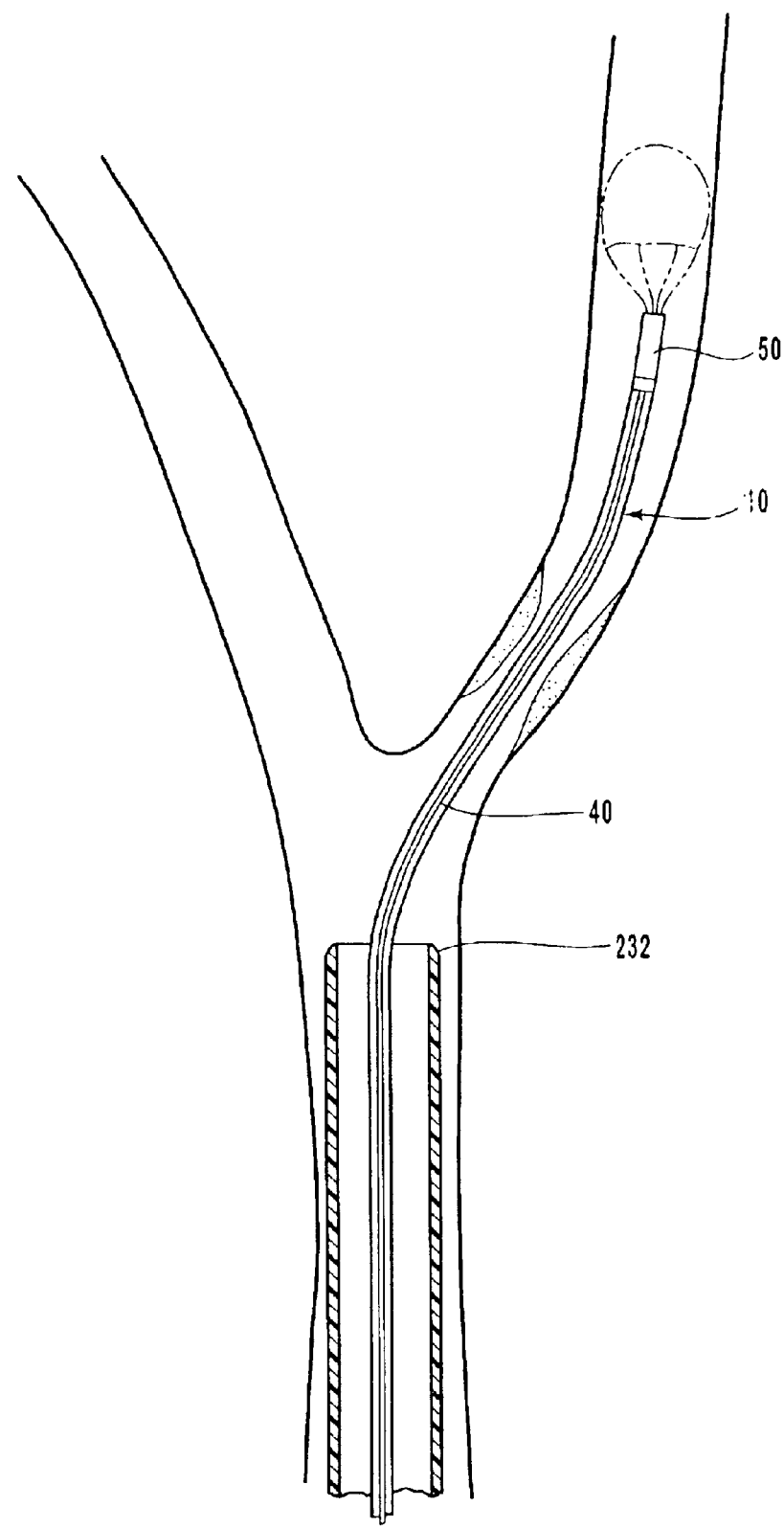
FIG. 15 illustrates one embodiment of the filter device of FIG. 2 deployed in the interior carotid artery distal of the lesion of FIG. 14.

Once in position, moving actuating member 40 distally actuates filter device 10 and deploys filter 50, as represented by block 118 and shown in dotted lines in FIG. 15. In this manner, filter assembly 42 is deployed from lumen 18 of guide member 12 and struts 52 expand to secure proximal end 58 of filter against the wall of the vessel, as shown in FIG. 6a. Alternatively, when struts 52 are formed from the same material as filter 50, the flow of blood through the vessel causes proximal end 58 to become secured against the wall of the vessel. Consequently, in either case, the blood flowing through the lesion subsequently flows through filter 50.

Figure 16:
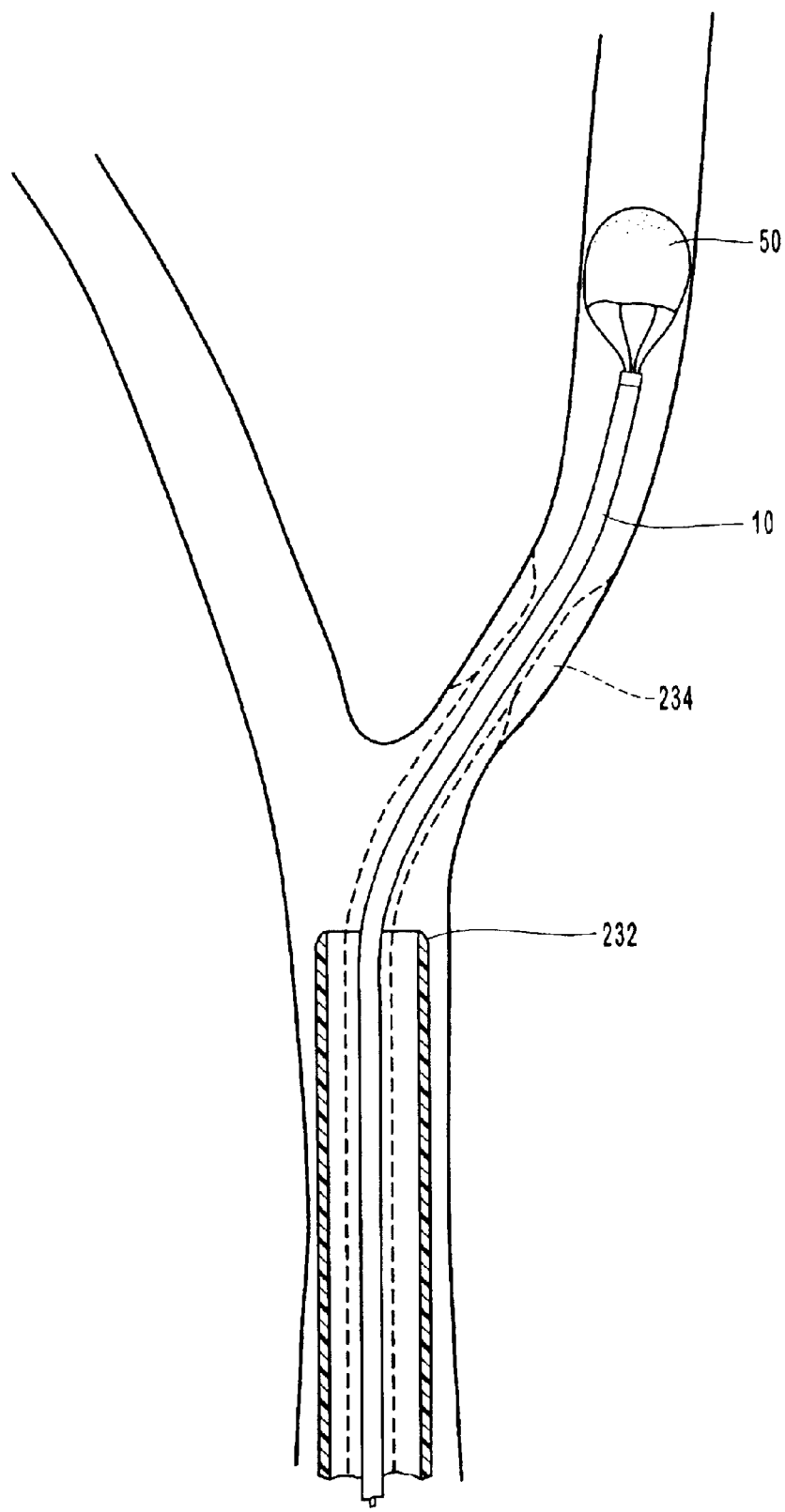
FIG. 16 illustrates one embodiment of the filter device of FIG. 2 deployed in the interior carotid artery distal of the lesion of FIG. 14 and a pre-dilation balloon.
Figure 17:
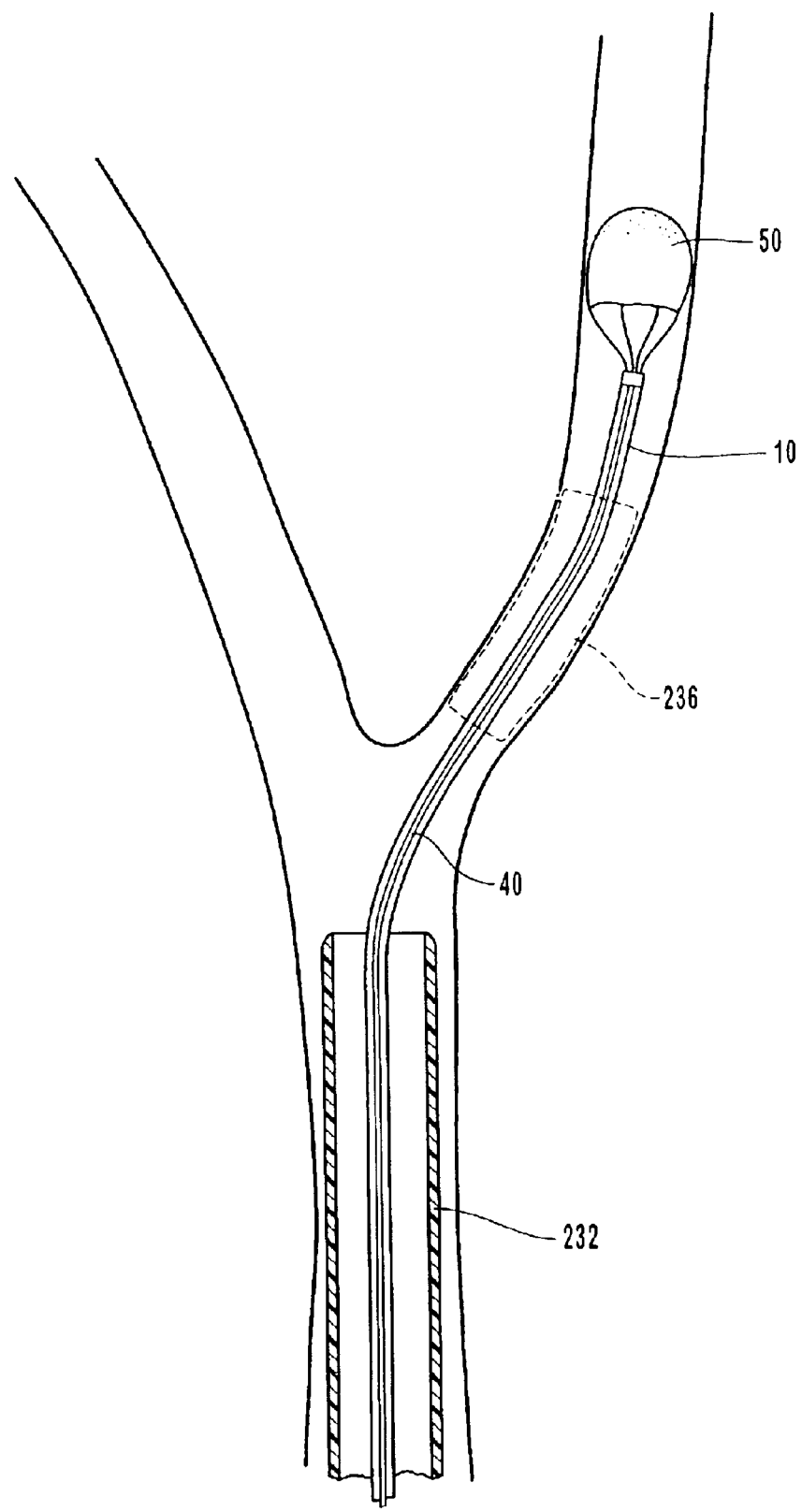
FIG. 17 illustrates one embodiment of the filter device of FIG. 2 deployed in the interior carotid artery distal of the lesion of FIG. 14 and a stent located about the lesion.

Next, a stent is placed over the lesion, as represented by block 120. This may be preceded by advancing a pre-dilation balloon 234, such as a relatively long, high-pressure balloon, over filter device 10, shown in dotted lines, until balloon 234 is within the lesion. Next, balloon 234 is inflated to dilate the lesion, as illustrated in FIG. 16, and then deflated and removed from the patient. Then a stent delivery system is advanced over guide member 12 until a stent 236, shown in dotted lines in FIG. 17, is within the lesion. The stent delivery system deploys stent 236, which then expands to fit the interior of the lesion within the artery. Once stent 236 is thus deployed, the stent delivery system is then removed.

To secure stent 236 in place, a post-dilation balloon, having a similar configuration to the pre-dilation balloon, is advanced over filter device 10 until the balloon is within stent 236. Subsequently, the post-dilation balloon is inflated to a pressure and held at the desired pressure for a period selected by the physician. The maintenance of the balloon at such a pressure for this period causes stent 236 to be imbedded into the inner wall of the vessel. Following imbedding stent 236 into the inner wall of the vessel, the balloon is deflated and removed.

To complete the procedure, the devices within the patient and punctured vessel and tissue are closed. With respect to filter device 10, locking mechanism 20 is activated to cause actuating member 40 to move in the proximal direction. The actuating member 40 draws struts 52 within lumen 18 of guide member 12, thereby causing proximal end 58 of filter 50 to be retained within lumen 18, as illustrated in FIG. 8 and represented by block 122 in FIG. 12. In another configuration, activating actuating member 40 causes proximal end 58 of filter 50 to contact distal end 26 of guide member 12, while remaining external from lumen 18. In either case, the material captured within filter 50 are enclosed and prevented from escaping during removal of filter device 10. By locating proximal end 58 of filter 50 within lumen 18 or in contact distal end 26 of guide member 12, filter device 10 securely encloses the material with a sufficiently low force to prevent escape of any material but not cause material to be extruded through the holes of filter 50.

Once filter 50 is in the retracted position, capture catheter 70 is advanced over guide member 12 until the capture catheter encloses filter device 10, as illustrated in FIG. 11. This capture catheter is optionally locked in place with respect to guide member 12 and the filter system, including filter device 10. Subsequently, the capture catheter 70 and the filter device 10 are removed from the patient, as represented by block 124. To complete the procedure, all remaining devices are removed from the patient and the vessel puncture is closed.

The previously described embodiment of a filter device of the present invention is only one illustrative embodiment of the filter device. The following discussion provides various other configurations of various alternate embodiments of the filter device, including the guide member, the capture catheter and various elements of components. The following embodiments can be used in a similar manner to filter device 10 in performing the above-discussed method to insert the filter device into a carotid artery or some other body lumen. Further, the applicability of the features and functions discussed with respect to the previously discussed embodiment of the present invention are applicable to the to the following embodiments.

Figure 18:
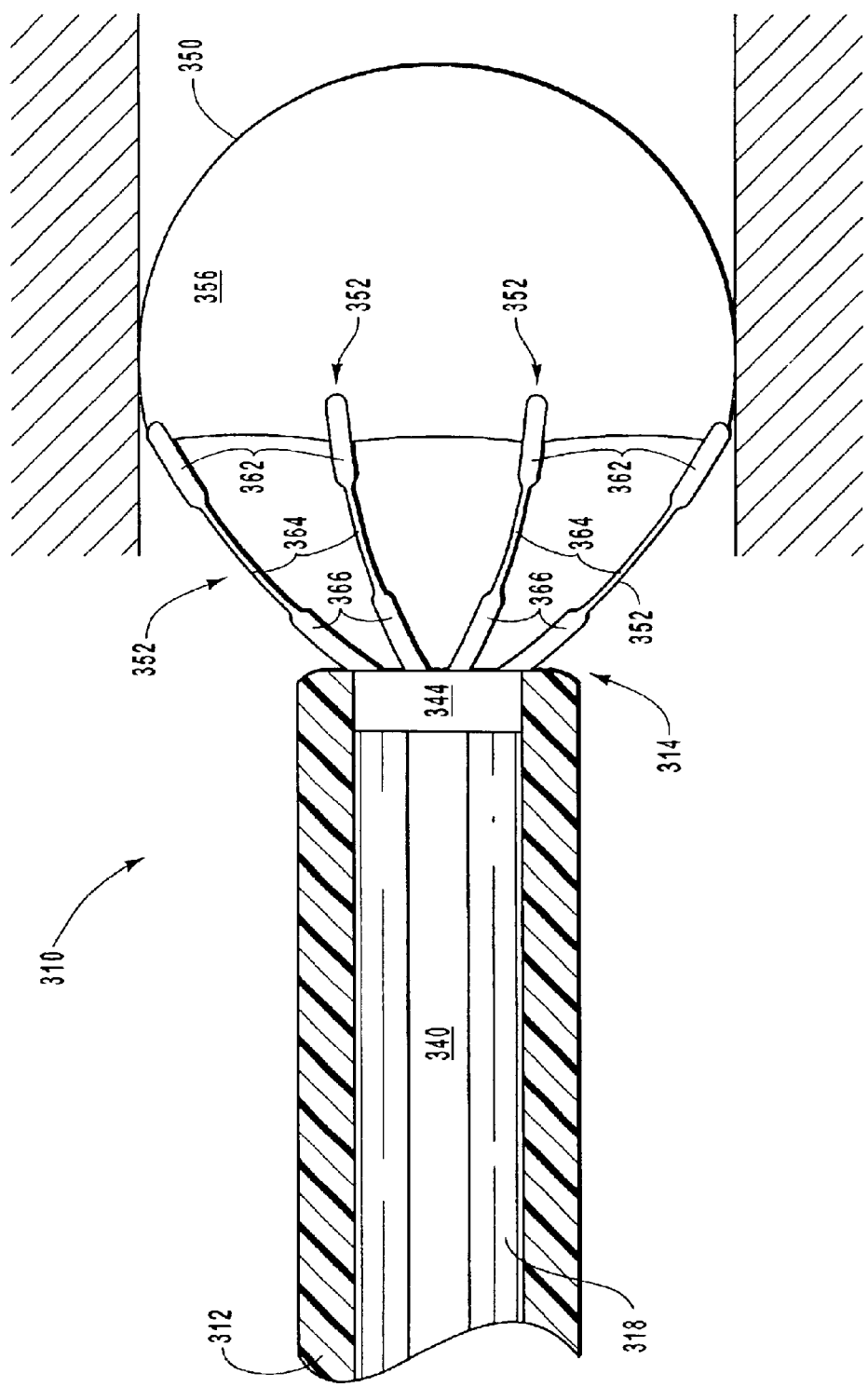
FIG. 18 illustrates a partial cross-sectional side view of another embodiment of the filter device of the present invention.

Referring now to FIG. 18 is another configuration or embodiment of the filter assembly and actuating assembly. As depicted in FIG. 18, a filter device 310 includes a guide member 312 having a distal end 314 and a lumen 318 extending from distal end 314 toward a proximal end (not shown). In this particular configuration, a sheath and cover are excluded from guide member 312. In another configuration, however, a sheath and cover can be included in a similar manner to guide member 12.

Disposed within lumen 318 are a filter assembly 342 and an actuator 340, with associated head 344. The filter assembly 342 includes a filter 350, which can be similar to other filters described herein, and a plurality of struts 352 extending from filter 350 to actuator 340 or head 344. Each strut 152 includes a distal portion 362, a proximal portion 366, and an intermediate portion 364 disposed between distal portion 362 and proximal portion 366. The struts 352 attach to filter 350 on the exterior of filter 350, on the interior of filter 350, along the edge of filter 350, through filter 350, or combinations of one or more of the proceeding. To provide additional surface area to connect each strut 352 to filter 30, each strut 352 can be configured so that distal portion 362 has a cross-sectional dimension larger than intermediate portion 364. Stated another way, distal portion 362 can have a larger surface area than intermediate portion 364. The large cross-sectional area provided by the cross-sectional dimension of distal portion 312 provides large area for bonding each strut 352 to filter 350. In this configuration, a strong bond is created between each strut 352 and filter 350.

Similarly, each strut 352 can be configured so that proximal portion 366 has a cross-sectional dimension larger than intermediate portion 364, while optionally having a similar, larger, or smaller cross-sectional dimension than distal portion 362. By having a large cross-sectional dimension and hence large surface area, each strut 352 can be securely connected to actuating member 340 or head 342 which can be similar to other actuating members and heads described herein.

By varying the cross-sectional dimensions of distal portion 362, intermediate portion 364, and/or proximal portion 366, the degree of bias exerted by each strut 352 to move distal portion 362 toward the wall of a blood vessel can be varied. The biasing force can also be changed through optionally varying the length of each strut 352 and/or changing the curvature of each strut 352.

Although reference is made herein to each strut 352 having the above-referenced configurations, one skilled in the art can appreciate that one or more of struts 352 can be configured as described above. Further, each strut 352 can optionally be configured differently so that each strut 352 can have similar or dissimilar biasing forces compared to others struts 352 of the same filter device. Through varying the biasing forces, the filter device can be used for a variety of different procedures or blood vessel configurations.

Struts 352 can be formed from Nitinol, stainless steel, metals, alloys, composites, plastics, polymers, synthetic materials, or combinations thereof. Each strut 352 can have a generally curved distal portion 362, proximal portion 366, and/or intermediate portion 364.

Figure 19:
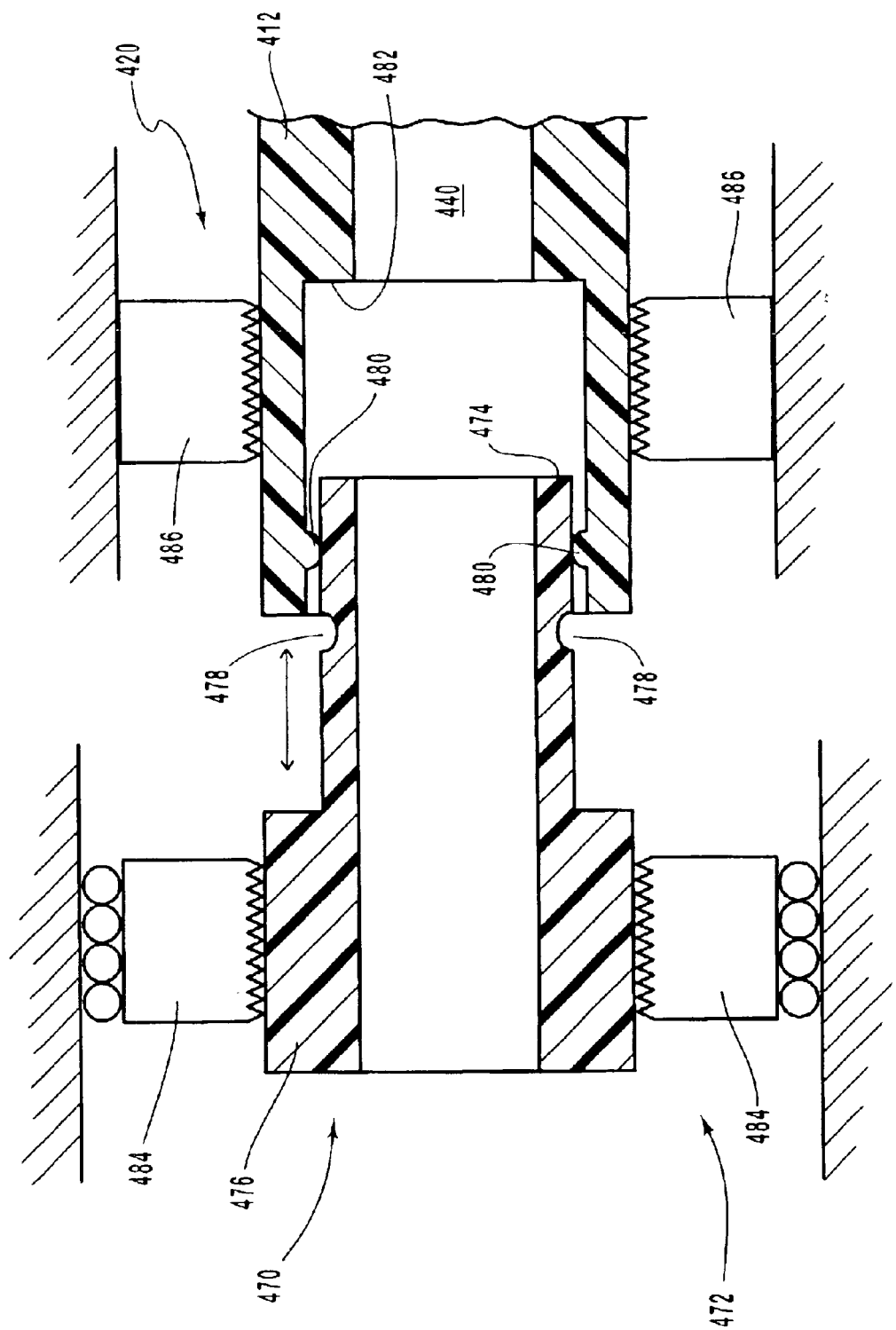
FIG. 19 illustrates a cross-sectional side view of another exemplary actuating assembly of the filter device according to the present invention.

Referring now to FIG. 19, illustrated is an alternate embodiment of actuator assembly, designated by reference number 420. This particular embodiment of actuator 420 is capable of deploying and retrieving a filter assembly with use of a clamp assembly 472.

As illustrated, actuating assembly 420 includes an actuating element 470, and an actuating member 440, each of which can be similar to other actuating elements and actuating members described herein. Actuating element 470 includes a distal end 474 that is configured to cooperate with guide member 412, which can be similar to the other guide members described herein, while a proximal end 476 of actuating element 470 is attached to proximal end of actuating member 440. The distal end 474 has a step configuration and includes protrusions 478 that are configured to cooperate with complementary indentations 480 formed in guide member 412. As actuating element 470 is moved in the distal direction, such as by a physician, clinician, or a device operated by the physician, clinician, or technician, protrusions 478 and indentations 480 mate to position actuating element 470 in a desired location relative to proximal end 416 of guide member 412, thereby positioning filter assembly 442 in a selected position, such as in the retracted position illustrated in FIG. 8.

As actuating element 470 is continually moved in the distal direction, distal end 474 meets a wall 482 formed in guide member 412 that prevents further movement in the distal direction. Through this configuration, actuating element 470 is prevented from excessive longitudinal displacement in the distal direction. This stopping of the longitudinal displacement of actuating element 470 indicates that filter assembly 442 is deployed.

As illustrated, actuator element 470 engages with clamp assembly 472. The clamp assembly 472 includes two annular clamp sets 484 and 486. Clamp set 484 couples to actuator element 470, while clamp set 486 couples to guide member 412. In this illustrative embodiment, clamp set 484 is capable of being translated along the longitudinal axis of the filter device, while clamp set 486 is fixed. Clamp set 484 can be connected to a threaded screw, hydraulic rams, pneumatic rams, slide systems, linear actuators, combinations thereof, or the like that enables clamp set 484 to move in the proximal and distal directions. For instance, in one embodiment a threaded screw is rotatably attached to clamp set 486, with clamp set 484 mounted thereto. Upon rotating the threaded screw, clamp set 484 advances along the threaded screw in either the proximal or distal direction to open or retract the filter assembly (not shown) of the filter device.

Generally, clamp assembly 472 can include a variety of different clamp sets, whether annular or opposed clamping jaws or clamp set, or the like as known to one skilled in the art. Further, clamp assembly 472 can use pneumatics, hydraulics, electricity, combinations thereof, or the like to move actuator element 470 and/or guide member 412.

Referring now to FIG. 20, another illustrative embodiment of the present invention is depicted. As shown, a guide member 512, which can be similar to the other guide member described herein, has a distal end 514, a proximal end 516, and a lumen 518 extending from distal end 514 to proximal end 516. A tip 515 of guide member 512 includes a plurality of struts 522, such as three or more struts. Each strut 522 can be biased such that a distal end thereof is biased to move outwardly from the longitudinal axis of guide member 512.

At least one strut, designated by reference numeral 524, is biased toward the longitudinal axis of guide member 512, as shown in FIG. 21. Disposed upon strut portion 524, as more clearly seen in FIG. 20, is a coil tip 526 that is commonly used with guidewires. This coil tip 526, either alone or in combination with strut 524, may be configured to allow a physician or clinician to shape the same before insertion into a body lumen. In this manner, the physician or clinician is able to configure the tip with an appropriately shaped J that enables guide member 512 to be guided through the tortuous anatomy of a patient. The coil tip 526 can be platinum, platinum alloys, radiopaque materials, metals, alloys, plastic, polymer, synthetic material, combinations thereof, or other materials that provide an appropriate radiopaque signature, while capable of being shaped, whether alone or in combination with strut 524, by a physician or clinician.

Attached to the distal ends of two or more of struts 522 is a filter 550. As shown, filter 550 is disposed within lumen 518 of guide member 512. In alternate embodiments, filter 550 can surround guide member 512 or partially surround and partially be contained within lumen 518. Filter 550 can have a variety of different configuration such as those described with respect to the other filters described herein.

Filter 550 can be attached to guide member 512 via a variety of different techniques and methods as known to one skilled in the art. For instance, filter 550 can be attached through adhesives, solvent bonding, thermal bonding, mechanical connections, or some other manner that is capable of securely connecting filter 550 to one or more of struts 522. In another configuration, a distal end of two or more struts 522 can include respective holes (not shown) through which strands of filter 550 can be passed and attached to strut 522 to connect filter 550 to struts 522. Alternately, the strands can be tied in a knot or folded back upon filter 550 and woven into or affixed to filter 550.

To maintain struts 522 in the closed position, i.e., not extending outwardly from guide member 512, a catheter 540 surrounds guide member 512. The catheter can extend completely or partially from the distal end to the proximal end of guide member 512. Illustratively, the catheter can surround substantially only struts 522. The catheter 540 acts as a restraining member or mechanism that applies a force against, the struts to prevent the struts from extending outwardly. Catheter 540 can have a lumen (not shown) that has an inside diameter that is sufficiently similar to the outside diameter of guide member 512 that struts 522 are restrained from extending outwardly. Through moving guide member 512 with respect to catheter 540, or vice versa, the distal ends of two or more of struts 522 are allowed to move outwardly to deploy filter 550, as illustrated in FIG. 21 that depicts guide member 512 having two struts 522. Retracting filter 550 and catheter 540 can be performed in a similar manner to that described with respect to the other filter devices discussed herein, such as but not limited to using a capture catheter.

As mentioned above, the catheter can extend completely or partially the length of the guide member. In another configuration, the catheter can be replaced with a sleeve, a band, or other structure that partially extends toward the proximal end of the guide member from the distal end. These sleeves, bands, or other structures can be radiopaque or include one or more radiopaque markers. Furthermore, these sleeves, bands, or other structures can be slidable relative to the guide member using an actuating member that is disposed on the exterior of the guide member, within the lumen of the guide member, or partially within the lumen and partially on the exterior of the guide member. The actuator member can be any of the actuator members described herein.

Figure 22:
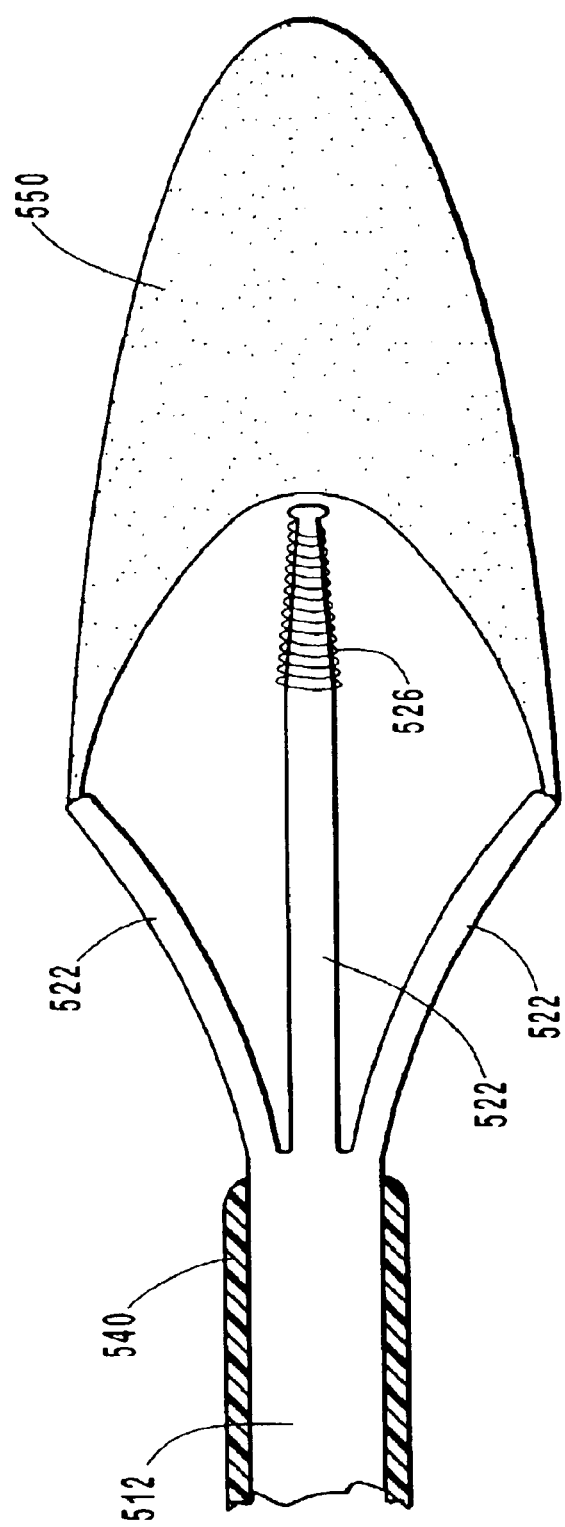
FIG. 22 illustrates a side view of the embodiment of FIG. 20 with the filter deployed.

According to an alternate configuration of the present invention, a filter device 610 includes a guide member 612 with a plurality of struts 622 disposed at a distal end 614 thereof. These struts 622 can be maintained in the closed position using a sleeve 660, as illustrated in FIG. 22. The sleeve 660 acts as a restraining member or mechanism that applies a force against the struts to prevent the struts from extending outwardly.

Sleeve 660 surrounds struts 622, and a filter 650, which can be similar to other filters described herein, when filter 650 is located on an exterior surface of guide member 612. Disposed within sleeve 660 or between sleeve 660 and guide member 612 and/or filter 650 are one or more actuating members or actuating members 654. These actuating members 654 are attached to guide member 612 at a location just proximal to the proximal end of each struts 622, identified by letter E, extend distally to the distal end of sleeve 660, and subsequently extend proximally on the outside of sleeve 660 to terminate at an actuating element 670 of an actuating assembly 620 (FIG. 25) via one or more holes 656 and lumen 618. Since one end of each actuating member 654 is located at the proximal end of sleeve 660, whether forming part of sleeve 660, attached to sleeve 660, attached to guide member 612, or combinations thereof, pulling actuating member 654 in the proximal direction by actuating element 670 of actuating assembly 620 (FIG. 25) causes actuating member 654 to preferentially separate sleeve 660 into one or more portions, thereby releasing struts 622, as illustrated in FIG. 24.

Figure 25:
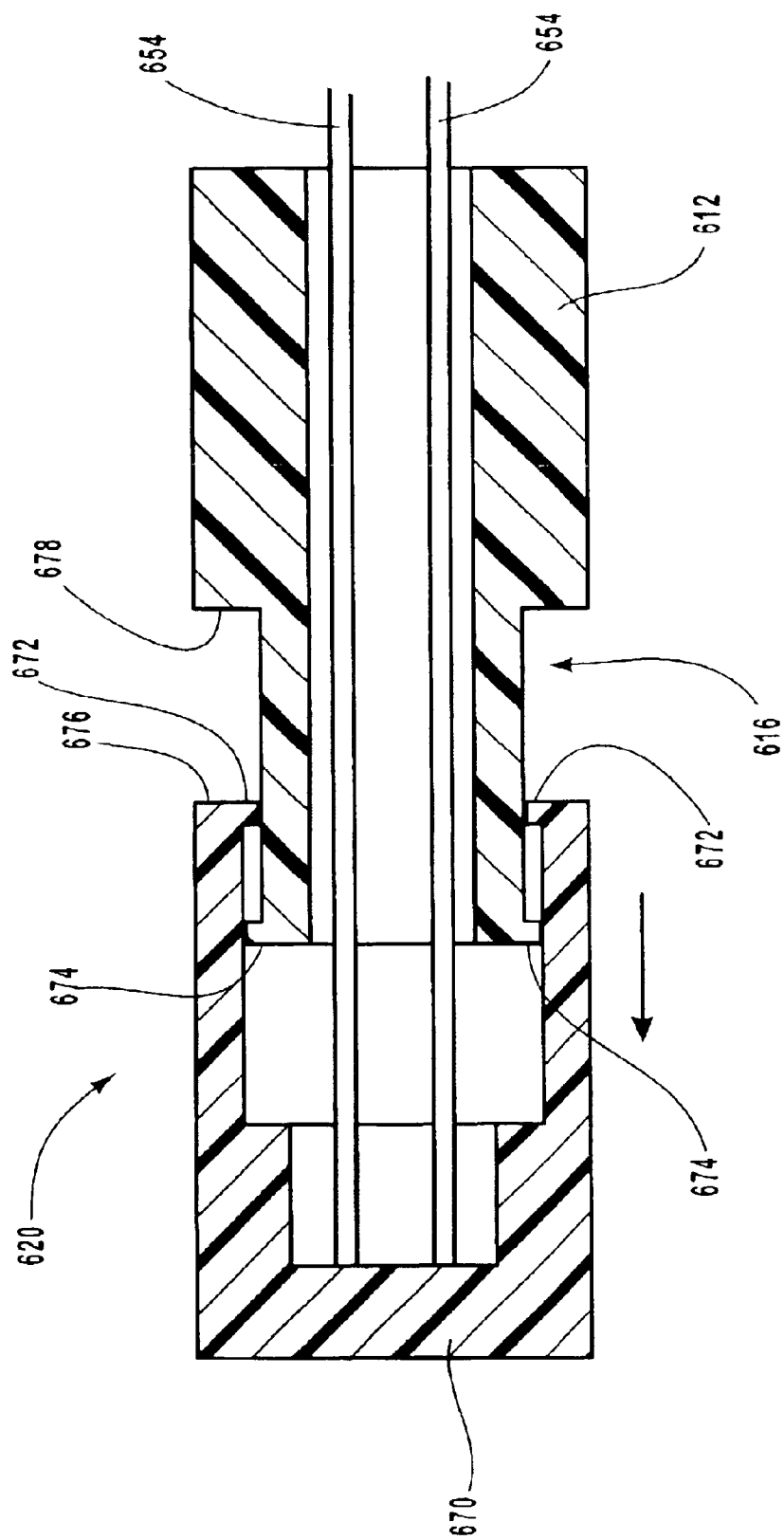
FIG. 25 illustrates a cross-sectional side view of another exemplary actuating assembly of the filter device according to the present invention.

Stated another way, and with reference to FIG. 25, one or more of actuating members 654 can cooperate with an actuating assembly 620 and connect to actuating element 670, such as through soldering, adhesives, or other forms of attachment. The actuating element 670 can be moved in the proximal direction until a stop member 672 formed in a proximal end 616 of actuating element 670 engages with a stop member 674 in guide member 612. During the movement from a distal end 676 of actuating element 670 cooperating with a surface 678 of guide member 612 to stop member 672 engaging with stop member 674, actuating member 654 moves in a proximal direction to preferentially separate sleeve 660.

Sleeve 660 can be formed from a variety of different materials, so long as the material is sufficiently strong to secure struts 522, while being configured to preferentially separate under the action of actuating member or actuating member 654. For example, sleeve 660 can be fabricated from heat shrink synthetic material, including but not limited to, low-density polyethylene (LDPE), polyethylene terphthalate (PET), Polytetrafluoroethylene (PTFE), fluorinated ethylene propylene (FEP), polyethylene (PE), polyurethane (PU) or silicone tubing.

Actuating members 654 can be formed from a variety of different materials, so long as the material used is sufficiently strong to allow an actuating mechanism, such as those actuating mechanisms disclosed herein, to move actuating members or actuating member 654 proximally without breaking the same. For example, actuating members 654 can be fabricated from plastics, polymers, metals, composites, alloys, synthetic materials, or combinations thereof.

Instead of using actuating members 654, embodiments of the present invention can employ various other manners to preferentially separate sleeve 660. For example, sleeve 660 can have dissolvable chemical bonds which dissolve due to a chemical reaction with the fluid in the vessel within which the filter device is disposed, bonds that are broken through applying resistive heating, ultrasonic or radio frequency energy, preferential regions or zones where the material has a weaker strength than other regions or zones of the sleeve, or combinations thereof.

Following is a discussion of other methods, devices, and systems for restraining or constraining one or more struts attached to or integrally formed as part of a guide member. The embodiments provide methods, devices, and systems for, applying a restraining force to one or more struts and subsequently releasing the same to allow the struts to expand outwardly.

Referring now to FIG. 26, depicted is a perspective view of one embodiment of a restraining member or mechanism. The restraining member or mechanism, is in the form of a sleeve 760 and associated securing member 762, the combination of which is adapted to surround one or more struts 752 of a guide member 712 and apply a restraining force against struts 752 to maintain struts 752 in a closed configuration. The sleeve 760 includes a first side 764 and a second side 766 with first and second sides 764, 766 being separated by an intermediate portion 768. The sleeve 760 surrounds guide member 712 in such a manner that intermediate portion 768 surrounds guide member 712 so that portions of intermediate portion 768 contacts with, are juxtaposed to, are contiguous with, or are adjacent one to another. The securing member 762 passes through such portions of intermediate portion 768 to secure sleeve 760 upon guide member 712. To further aid with applying a restraining force against struts 752, first side 764 and second side 766 are folded to attach to respective portions of outside surface of sleeve 760.

The process of forming the restraining member or mechanism of FIG. 26 is illustrated in FIGS. 27 and 28. With reference first to FIG. 27, which depicts sleeve 760 in an open position before securing member 762 is coupled thereto, sleeve 760 can be directly formed on guide member 712 or can be formed on a separate tubular member and subsequently attached or coupled to guide member 712. Sleeve 760 is illustrated as having a generally polygonal configuration, however, one skilled in the art can appreciate that sleeve 760 can have various other configuration so long as it is capable of performing the functions described herein. In this exemplary configuration, sleeve 760 is coupled directly to a guide member 712. The first side 764 and second side 766 of sleeve 760 are wrapped around at least a portion of guide member 760, until a portion of intermediate portion 768 is in close proximity another portion of intermediate portion 768. Alternatively, a first side 764 can be contacting, juxtaposed, contiguous, or adjacent to second side 766.

When the portions of intermediate portion 768 are in close proximity, securing member 762, or alternatively some other actuating member, is stitched through both sleeve 760 to couple the portions of intermediate portion 768, as shown in FIG. 28. Once securing member 762 is drawn straight, first end 764 and second end 766 are folded to attach to respective outside surfaces of sleeve 760, as shown in FIG. 25.

In an alternate configuration, as illustrated in FIG. 29, sleeve 760 can include a plurality of apertures 780 on portions of intermediate portion 768 that receive securing member 762 thereby allowing securing member 762 to be passed through apertures 780 rather than stitched through sleeve 760. In another embodiment, first end 764 of sleeve 760 can be coupled to second end 764 of sleeve 760 without attaching first end 764 or second end 766 to the outside surface of sleeve 760. Depending upon the particular configuration, a portion of first end 764 can overlap a portion of second end 766, or vice versa. Alternatively, first end 764 and second end 766 contact each other but do not overlap. Similarly, first end 764 and second end 766 can be adjacent to one another, adjoining one another, contiguous to one another, or juxaposed to one another.

To operate the restraining member or mechanism described in reference to FIGS. 26–29, a proximal end (not shown) of securing member 762 extends to a proximal end (not shown) of guide member 712, either within or without a lumen of the guide member 712. Disposed upon the end of securing member 762 is an actuating member, such as actuating member 20, which allows a physician or clinician to move securing member 762 longitudinally to remove securing member 762 from being disposed through at least a portion of sleeve 760. By so doing, the restraining force applied by sleeve 760 is released, struts 752 extend outwardly, and the filter (not shown) is deployed.

Sleeve 760 can be formed from a variety of different materials, so long as the material is sufficiently strong to restrain one or more struts 752. For example, sleeve 760 can be fabricated from various types of polymer or silicone films, such as but not limited to, heat shrink plastic, polymer, low-density polyethylene (LDPE), polyethylene terphthalate (PET), Polytetrafluoroethylene (PTFE), fluorinated ethylene propylene (FEP), polyethylene (PE), polyurethane (PU), or silicone tubing.

Securing member 762 can be formed from a variety of different materials, so long as the material used is sufficiently strong to allow the actuating mechanisms disclosed herein to move securing member 762 proximally without breaking securing member 762. For example, securing member 762 can be fabricated from plastics, polymers, metals, composites, alloys, synthetic materials, combinations thereof, or other material that is capable of performing the function of being disposed through sleeve 760 and capable of being withdrawn therefrom.

Referring now to FIGS. 30–34, illustrated is another alternate configuration of a restraining member or mechanism. This particular configuration utilizes a hinged configuration with a securing member acting as the pin to maintain the hinged portions of a sleeve in a closed configuration to constrain or restrain a portion of the guide member.

As shown in FIG. 30, a sleeve 860 includes a plurality of channels 864a–864f that are adapted to receive a securing member 862. Both a first side 866 and a second side 868 of sleeve 860 are formed with some of channels 864a–864f, i.e., channels 864a, 864c, and 864e on first side 866 and channels 864b, 864d, and 864f on second side 868. Through passing securing member 862 through channels 864a–864f in sequential order, so that securing member 862 passes through a channel on first side 866 and subsequently a channel on second side 868, first side 866 is coupled to second side 868 and sleeve 860 applies a restraining force against the struts (not shown) of a guide member.

The process of forming the restraining member or mechanism of FIG. 30 is illustrated in FIGS. 31–34. With reference first to FIG. 31, which depicts sleeve 860 in an open position before securing member 862 is coupled thereto, sleeve 860 includes a number of extensions or tongues 870a–870n. These extensions 870a–870n are configured to surround a tubular member or tube, such as but not limited to, a guide member 812, and form channels 864a–864f within which securing member 862 is located, as will be described hereinafter.

Figure 33:
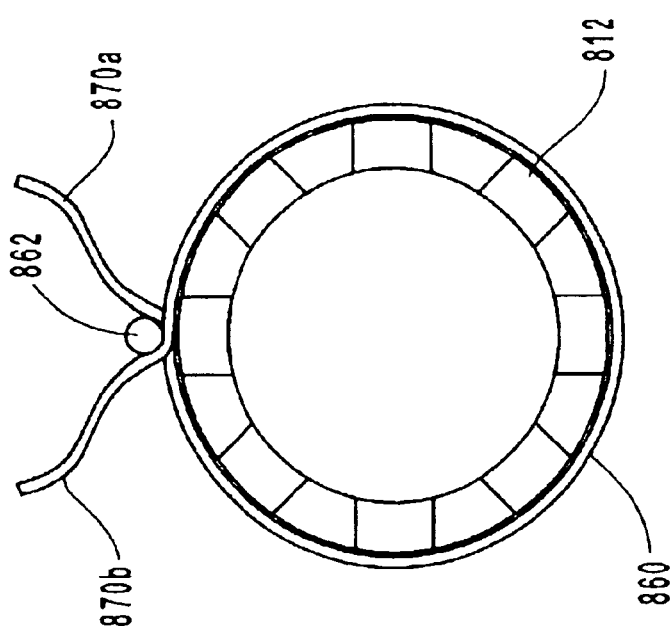
FIG. 33 illustrates a side view of the restraining member FIG. 30 part way through restraining the filter device according to another aspect of the present invention.
Figure 36:
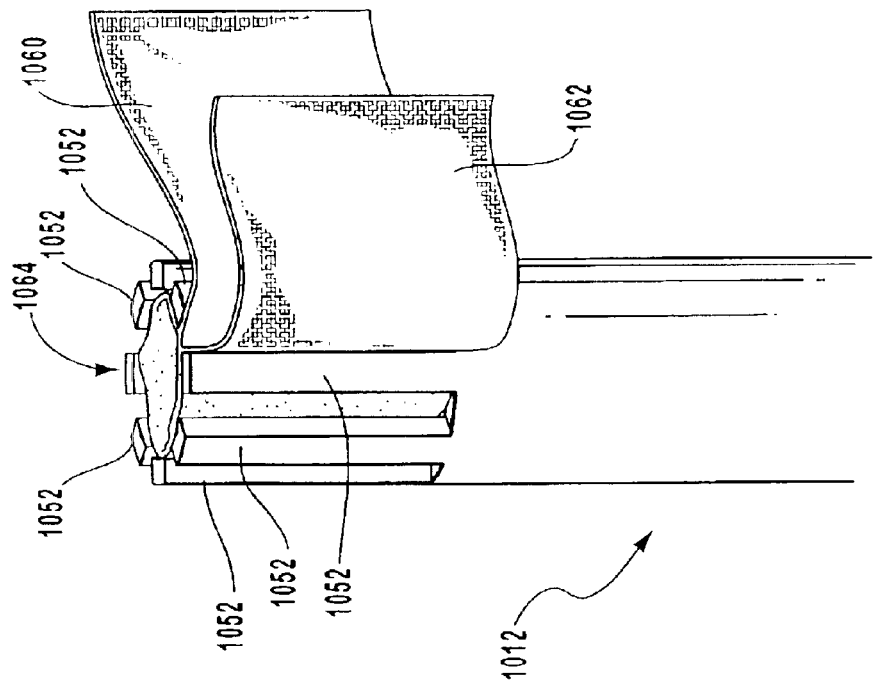
FIG. 36 illustrates a perspective view of another embodiment of a filter device with a restraining member coupled to the filter device according to another aspect of the present invention.

To attach sleeve 860 to guide member 812, sleeve 860 is positioned over the desired portion of guide member 860. The securing member 862 is placed in close proximity to guide member 860, as shown in FIGS. 31 and 32. The ends of the extensions 870a–870n are inserted between guide member 860 and securing member 862, as shown in FIG. 33. Alternatively, extensions 870a–870n can be partially wrapped around guide member 812 and securing member 862 placed into contact with these partially wrapped extensions 870a–870n.

Figure 34:
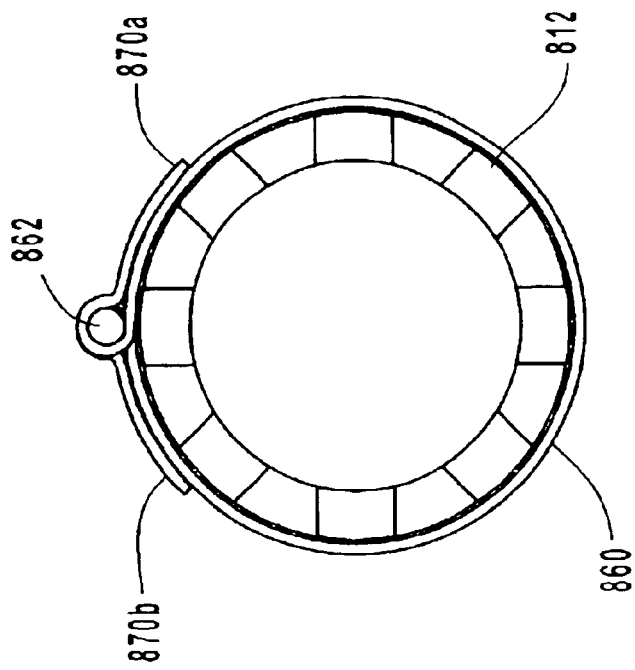
FIG. 34 illustrates a side view of the restraining member FIG. 30 as it restrains the filter device according to another aspect of the present invention.

After the extensions 870a–870n are pulled tightly around guide member 812 and securing member 862, an end of each extension 870a–870n is folded over securing member 862 to attach to the outer surface of sleeve 860, as shown in FIGS. 30 and 34. In this manner, channels 862a–862n are formed and sleeve 860 is configured with securing member 862 to releasably restrain the struts (not shown) of guide member 812.

Releasing the restraining force applied by sleeve 860, alone or in combination with securing member 862, is achieved through moving or pulling securing member 862 longitudinally with respect to guide member 812. The securing member 862 is withdrawn from channels 864a–864f to allow the biasing force of the struts (not shown) to extend the struts outwardly to deploy the filter (not shown). The longitudinal motion of securing member 862 can be initiated through a variety of different mechanisms as described herein, such as but not limited to actuating assembly 20, or otherwise known to one skilled in the art in light of the teaching contained herein.

Figure 35:
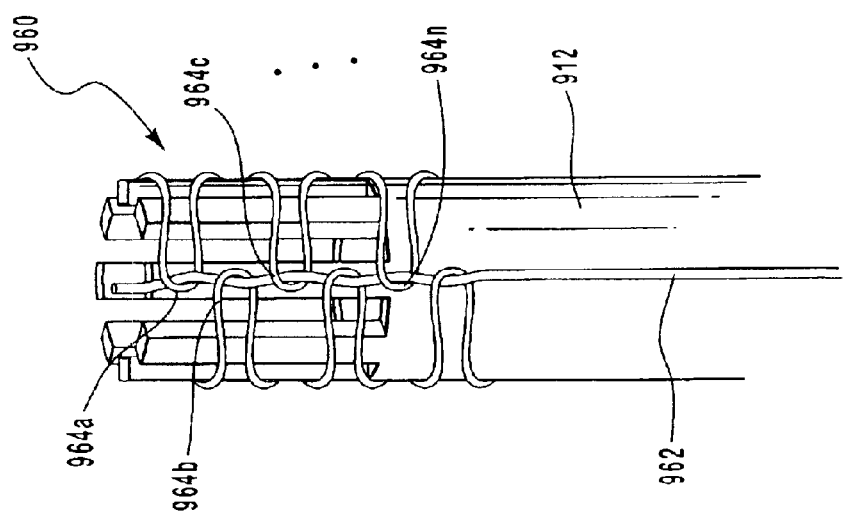
FIG. 35 illustrates a perspective view of another embodiment of a filter device with a restraining member coupled to the filter device according to another aspect of the present invention.

Referring now to FIG. 35, depicted is another embodiment of a restraining member or mechanism of the present invention. The restraining member 960 includes a number of hoops 964a–96n that are adapted to receive a securing member 962. In a similar manner to that described with respect to other embodiments of the restraining member or mechanism, securing member 962 is disposed within hoops 964a–964n so that restraining member 960 applies a retaining force against the struts of a guide member 912. The securing member 962 can be removed from hoops 964a–964n to thereby allow the struts to extend outwardly to deploy the filter (not shown). The restraining member 960 may be made from metallic wires, polymer fibers, or other materials that can be manipulated to form hoops through which a securing member is disposed and which can expand outwardly either under the influence of one or more struts or due to a biasing force applied by the configuration and/or material of the restraining member.

The restraining member 960 can be attached to guide member 912 and/or one or more of the struts associated therewith through various attachment mechanisms. For instance, restraining member 960 can be attached to guide member and/or one or more of the struts through adhesives, mechanical fasteners, securing loops, or other manner that securely attaches restraining member 960 to the guide member and/or one or more of the struts. Alternatively, restraining member 960 may be attached to securing member 962 and be removed when securing member 962 is moved in a proximal direction.

Referring now to FIGS. 36–39, depicted is another embodiment of a restraining member or mechanism of the present invention. Instead of a separate restraining member or mechanism that is connected to a guide member, the filter media itself is adapted to function both as a filter and as a restraining member or mechanism.

Figure 37:
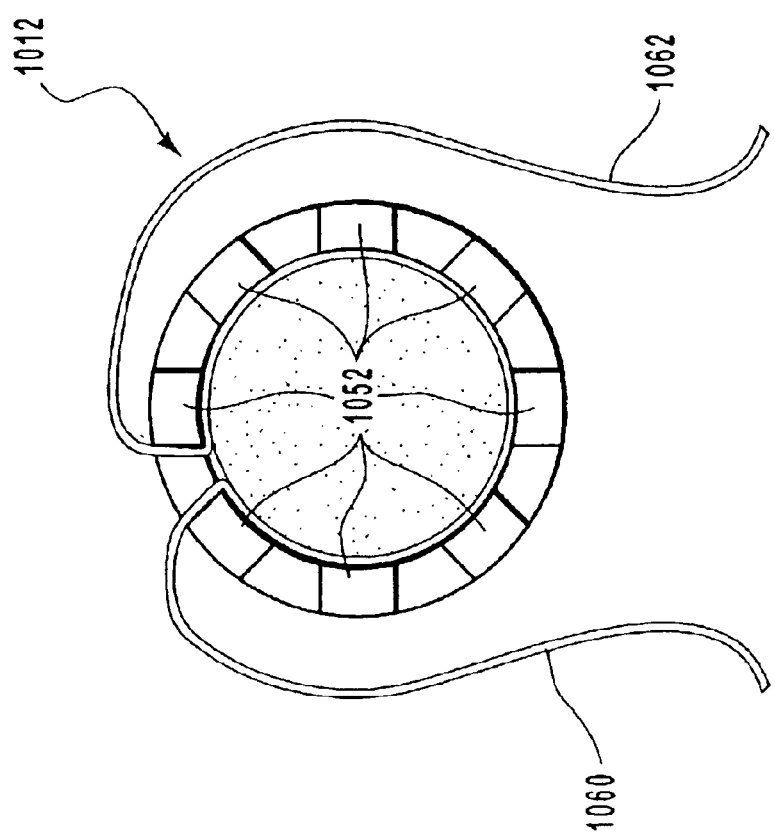
FIG. 37 illustrates a side view of the restraining member of FIG. 36 before becoming coupled to the filter device according to another aspect of the present invention.

As illustrated, a guide member 1010 includes a plurality of struts 1052 that are adapted to extend outwardly to deploy a filter 1050 that is disposed within a lumen 1018 of guide member 1010. The filter 1050 includes two flaps 1060 and 1062 that extend between a gap 1064 between two struts 1052. These flaps 1060 and 1062 are adapted to be pulled around struts 1052 to compress them and secure filter 1050 within lumen 1018, as illustrated in FIG. 37. These flaps 1060 and 1062 can be integral with filter 1050, two separate members that are bonded or otherwise connected to filter 1050, or a single member that has an intermediate portion bonded or otherwise connected to filter 1050, with the ends of the member forming flaps 1060 and 1062.

Figure 38:
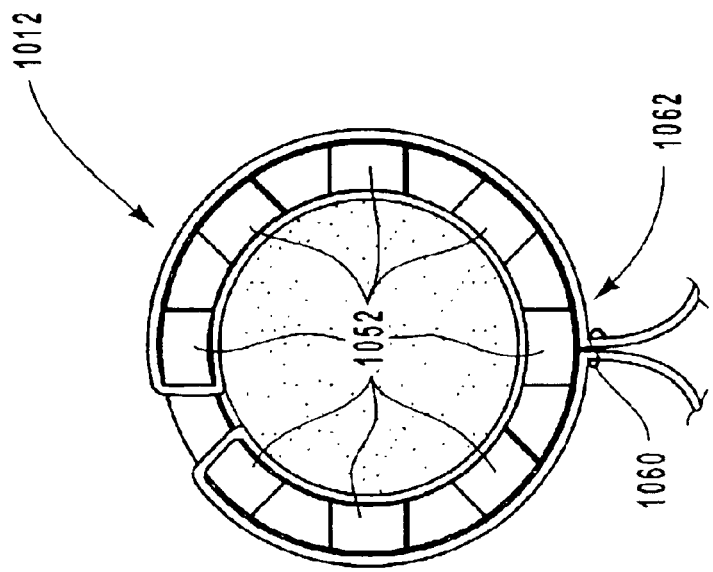
FIG. 38 illustrates a side view of the restraining member of FIG. 36 before becoming coupled to the filter device according to another aspect of the present invention.

When flaps 1060 and 1062 have been positioned to securely retain struts 1052, they are then stitched together at a location 1066 identified in FIG. 38 with an actuating member 1070. This actuating member 1070 extends the length of the filter device to cooperate with an actuating assembly, such as but not limited to an actuating assembly described herein and those others known to one skilled in the art in light of the teaching contained herein.

Figure 39:
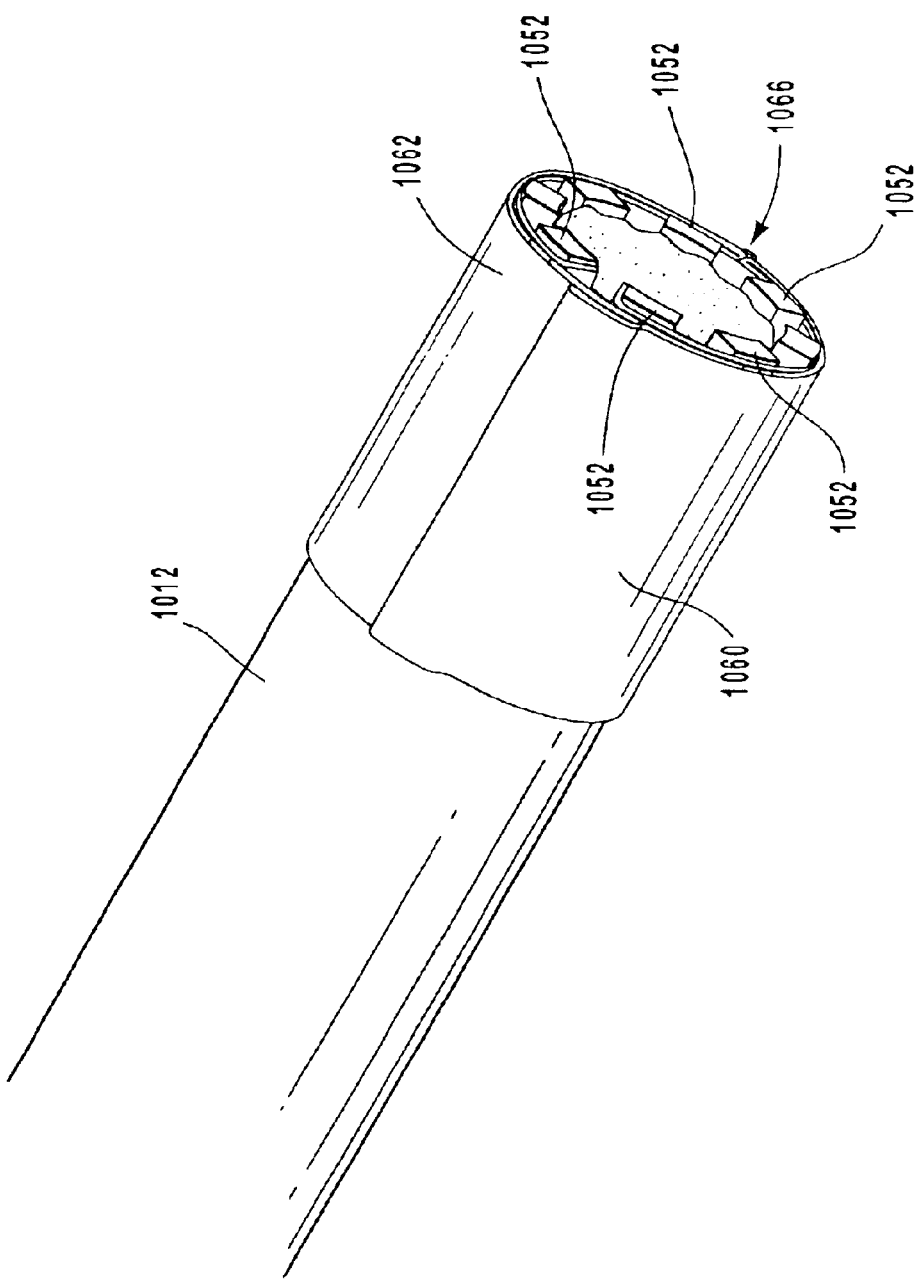
FIG. 39 illustrates perspective view of the restraining member FIG. 36 as it restrains the filter device according to another aspect of the present invention.

Following the coupling of flaps 1060 and 1062 using actuating member 1070, flaps 1060 and 1062 are folded back around the bundled struts 1052 and filter 1050, and then attached to filter 1050, struts 1052, or other portion of guide member 1012, as illustrated in FIG. 39. When actuating member 1070 is moved in a proximal direction, flaps 1060 and 1062 are released and filter 1050 is deployed as struts 1052 extend outwardly.

Although reference is made to two flaps 1060 and 1062, one skilled in the art can appreciate that the filter can includes one or more flaps. For instance, one flap can be wrapped around struts 1052 and an end of the flap sewn or otherwise releasable connected to filter 1050.

Figure 40:
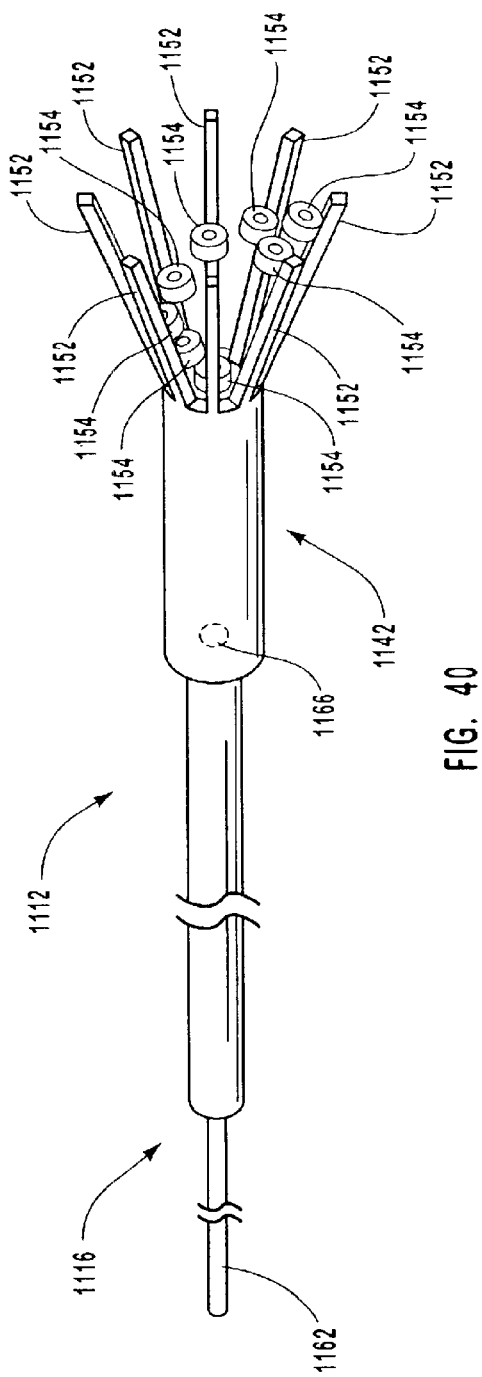
FIG. 40 illustrates a perspective side view of another embodiment of a filter device with a restraining member coupled to the filter device according to another aspect of the present invention.

Referring now to FIG. 40, depicted is another embodiment of a restraining member or mechanism of the present invention. This particular configuration is depicted as part of a filter assembly 1142 that can be coupled to or attached to a distal end of a guide member. The filter assembly 1142 can includes a strut assembly 1144 and a filter (not shown) coupled to strut assembly 1144. The strut assembly 1144 has an elongated proximal end 1146 and a distal end 1148 having a plurality of struts 1152. The length of elongated proximal end 1146 can vary based upon the particular configuration of the guide member. For instance, proximal end 1146 can have any length greater than 1 centimeter.

Figure 41:
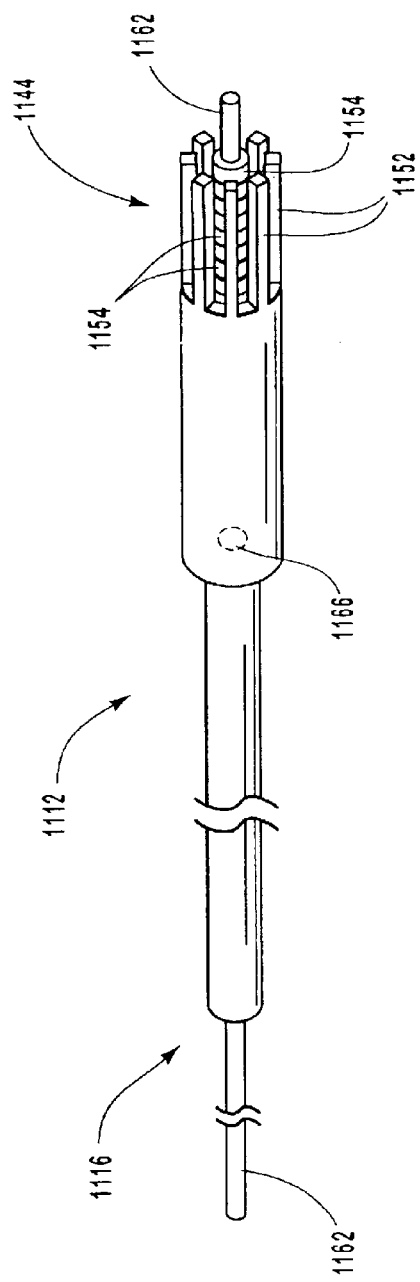
FIG. 41 illustrates a perspective side view of the restraining member FIG. 40 as it restrains the filter device according to another aspect of the present invention.

As mentioned above, disposed at distal end 1148 are struts 1152. Each strut 1152 includes a tubular member 1154 adapted to receive a securing member 1162. Adjacent tubular members 1154 on adjacent struts 1152 are staggered such that when struts 1152 are brought together securing member 1162 can be disposed through tubular members 1154 to restrain struts 1152 and prevent them from extending outwardly, as illustrated in FIG. 41.

The securing member 1162 can extend through a lumen 1164 of strut assembly 1144 into a lumen 1118 of guide member 1112 to terminate at an actuating assembly (not shown) at a proximal end 1116 of guide member 1112. Alternatively, securing member 1162 can extend through lumen 1164 to exit through an aperture 1166, depicted in dotted lines, in strut assembly 1144 before terminating at an actuating assembly (not shown) at a proximal end of guide member 1112. In still another configuration, securing member 1162 can pass into lumen 1164 through aperture 1166, depicted in dotted lines, in strut assembly 1144 before terminating at an actuating assembly (not shown) at a proximal end of guide member 1112.

Each tubular member 1154 coupled to struts 1152 can be fabricated from a metal, a plastic, polymer, a polymer, a synthetic materials, whether or not the material is the same as that forming guide member 1112. In one embodiment, each tubular member 1154 is a polymer tube, such as a polyimide or polyurethane tube that is fixed to respective struts 1152 with adhesive. In another configuration, each tubular member 1154 is a metallic cut tube that may be attached to respective struts 1152 with and adhesive or solder. In still another configuration, each strut 1152 includes an aperture through which securing member 1162 passes to restrain struts 1152 and prevents the same from extending outwardly.

Figure 42:
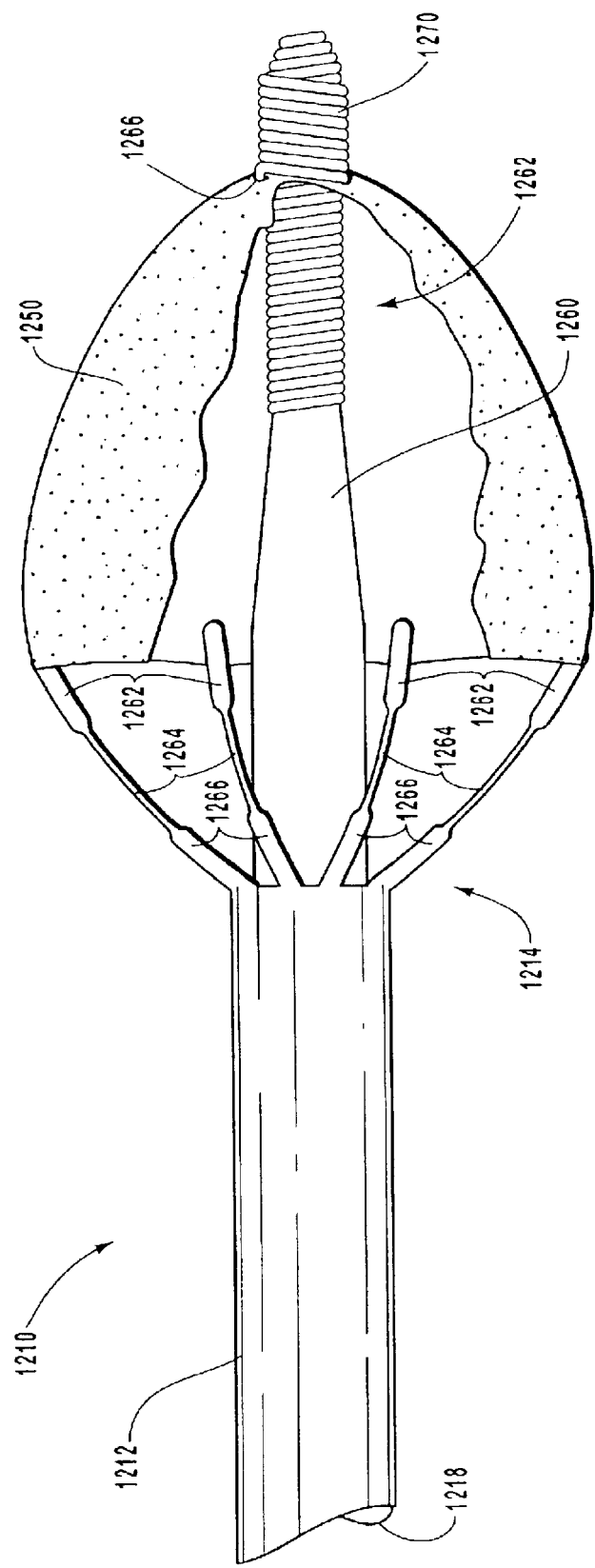
FIG. 42 illustrates a side view of another embodiment of a filter device according to another aspect of the present invention.

Referring now to FIG. 42 is another configuration or embodiment of a device according to another aspect of the present invention. As depicted in FIG. 42, a filter device 1210 includes a guide member 1212 having a distal end 1214 and a lumen 1218 extending from distal end 1214 toward a proximal end (not shown). In this particular configuration, and for ease of explanation, filter device 1210 is devoid of a restraining member or mechanism, however, in other configurations, filter device 1210 can include a restraining member or mechanism.

Disposed at distal end 1214 are a plurality of struts 1252, coupled to which is a filter 1250. Although reference is made herein to struts 1252 being integrally formed with guide member 1212, it can be appreciated that struts 1252 can be part of a strut assembly that is attached to proximal end 1214 of guide member 1212. For instance, the struts assembly can have a proximal end that terminates substantially with a proximal end of the guide member or at a location distal to the proximal end of the guide member, whether such location is close to the distal end of the guide member or the proximal end of the guide member.

Each strut 1252 includes a distal portion 1262, a proximal portion 1266, and an intermediate portion 1264 disposed between distal portion 1262 and proximal portion 1266. The struts 1252 attach to filter 1250 on the exterior of filter 1250, on the interior of filter 1250, along the edge of filter 1250, through filter 1250, or combinations of one or more of the proceeding. To provide additional surface area to connect each strut 1252 to filter 1250, each strut 1252 can be configured so that distal portion 1262 has a cross-sectional dimension larger than intermediate portion 1264. Stated another way, distal portion 1262 can have a larger surface area than intermediate portion 1264. The large cross-sectional area provided by the cross-sectional dimension of distal portion 1212 provides large area for bonding each strut 1252 to filter 1250. In this configuration, a strong bond is created between each strut 1252 and filter 1250.

Similarly, each strut 1252 can be configured so that proximal portion 1266 has a cross-sectional dimension larger than intermediate portion 1264, while optionally having a similar, larger, or smaller cross-sectional dimension than distal portion 1262. By having a large cross-sectional dimension and hence large surface area, each strut 1252 can apply a greater biasing force to extend strut 1252 outwardly to deploy filter 1250.

By varying the cross-sectional dimensions of distal portion 1262, intermediate 1252 portion 1264, and/or proximal portion 1266, the degree of bias exerted by each strut to move distal portion 1262 toward the wall of a blood vessel can be varied. The biasing force can also be changed through optionally varying the length of each strut 1252 and/or changing the curvature of each strut 1252.

Although reference is made herein to each strut 1252 having the above-referenced configurations, one skilled in the art can appreciate that one or more of struts 1252 can be configured as described above. Further, each strut 1252 can optionally be configured differently so that each strut 1252 can have similar or dissimilar biasing forces compared to others struts 1252 of the same filter device. Through varying the biasing forces, the filter device can be used for a variety of different procedures or blood vessel configurations.

Struts 1252 can be formed from Nitinol, stainless steel, metals, alloys, composites, plastics, polymers, synthetic materials, or combinations thereof. Each strut 1252 can have a generally curved distal portion 1262, proximal portion 1266, and/or intermediate portion 1264.

Disposed with lumen 1218 at distal end 1214 is a core 1260 forming part of an atraumatic tip 1262. Surrounding at least a portion of core 1260 is a coil 1264 that provides flexibility and radiopaque properties to atraumatic tip 1262. The core 1260 passes through an aperture 1266 in a distal end of filter 1250. Alternatively, core 1260 passes through one or more pores formed in filter 1250.

To secure filter 1250 to atraumatic tip 1262, a securing coil 1270 surrounds a portion of coil 1264 and the distal end of filter 1250. Although this is one manner to connect filter 1250 to atraumatic tip 1262, one skilled in the art can identify various other manners to connect filter 1250 to atraumatic tip 1262. For instance, the distal end of filter 1250 can be bonded to atraumatic tip 1262 using adhesives, mechanical fasteners, crimping, seals, friction fit, press fit, or other manners to connect filter 1250 to atraumatic tip 1262. In another configuration, filter 1250 is not connected to atraumatic tip 1262 but can slide along a portion of atraumatic tip 1262.

Figure 43:
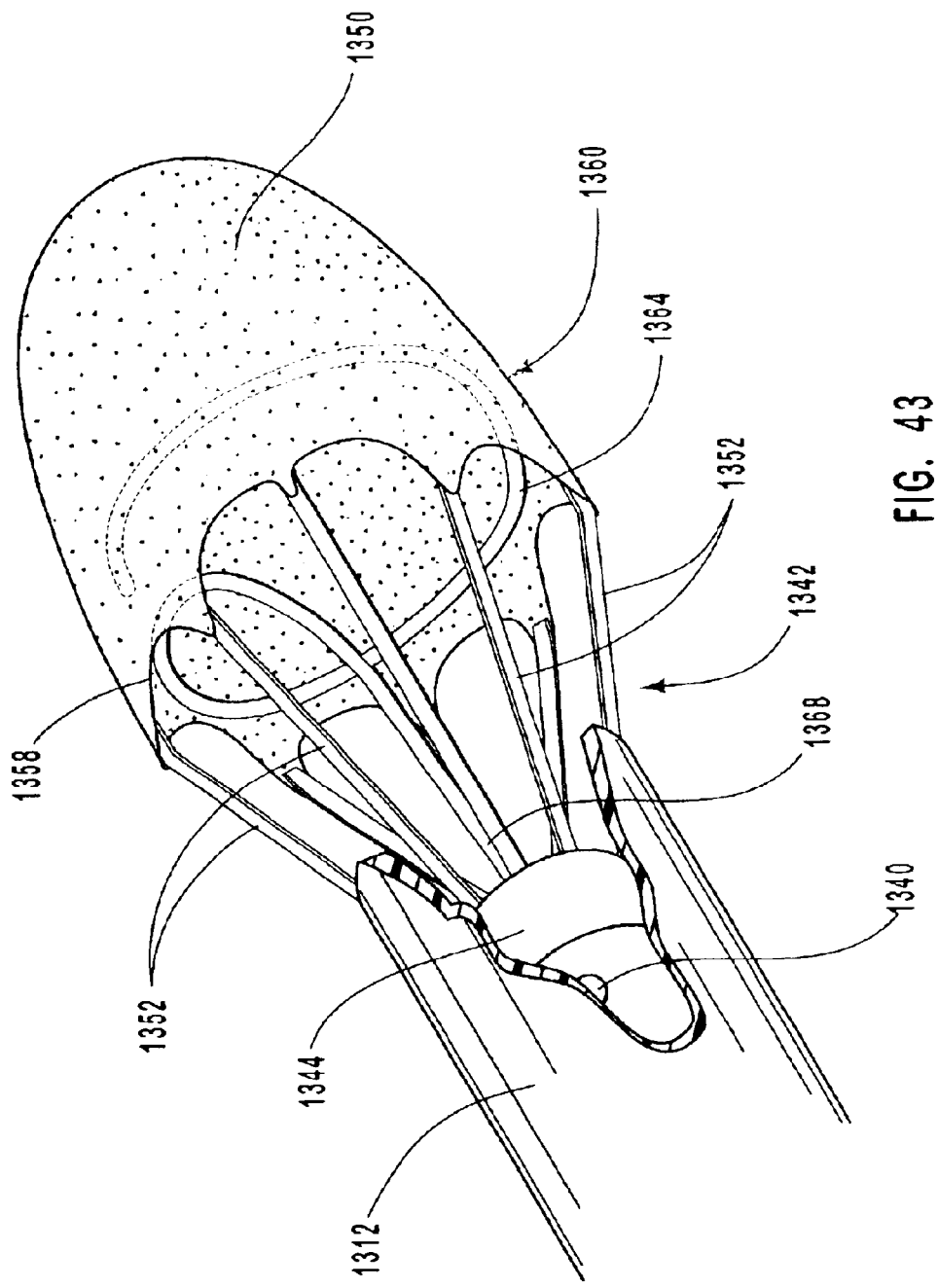
FIG. 43 illustrates a side view of yet another embodiment of a filter device according to another aspect of the present invention.

Referring now to FIG. 43, another illustrative embodiment of the present invention is depicted. The majority of the features previously discussed with respect to other embodiments of the present invention apply to this exemplary embodiment.

A filter assembly 1342 comprises a filter 1350 and a spring member 1364. Filter 1350 includes a plurality of struts 1352. These struts 1352 are lengthened strands of filter 1350. These struts 1352 connect filter 1350 to actuating member 1340 and are unbiased. Alternatively, struts 1352 can be biased to open filter 1350.

Disposed at proximal end 1358 of filter 1350, is biased spring member 1364. Biased spring member 1364 has a coil-type configuration and includes a proximal end 1368 that extends into lumen 1318 of guide member 1312 to be attached to actuating member 1340, such as similar to actuating member 40 discussed herein, and/or a head 1344. Spring member 1364 is biased to an opened position where spring member 1364 forms opening 1360. During deployment of filter assembly 1342, the flow of blood through the blood vessel applies a force to filter 1350. This force enables filter 1350 to be withdrawn from lumen 1318 and become deployed into the form described herein. Since spring member 1364 is biased to open, spring member 1364 draws the outer peripheral edge of filter 1350 at proximal end 1358 toward the inner wall of the blood vessel.

To retract filter 1350, actuating member 1340 is moved in the proximal direction, causing proximal end 1358 of filter 1350 to be drawn proximally. This causes proximal end 1358 to be drawn toward lumen 1318 and become closed, thereby enabling filter 1350 to be removed through the procedure discussed herein, such as through use of a capture catheter.

Various configurations of capture catheter are known to those skilled in the art in light of the teaching contained herein. The capture catheters described herein can be used with any of the embodiments of the filter device or guide member described herein.

Figure 44:
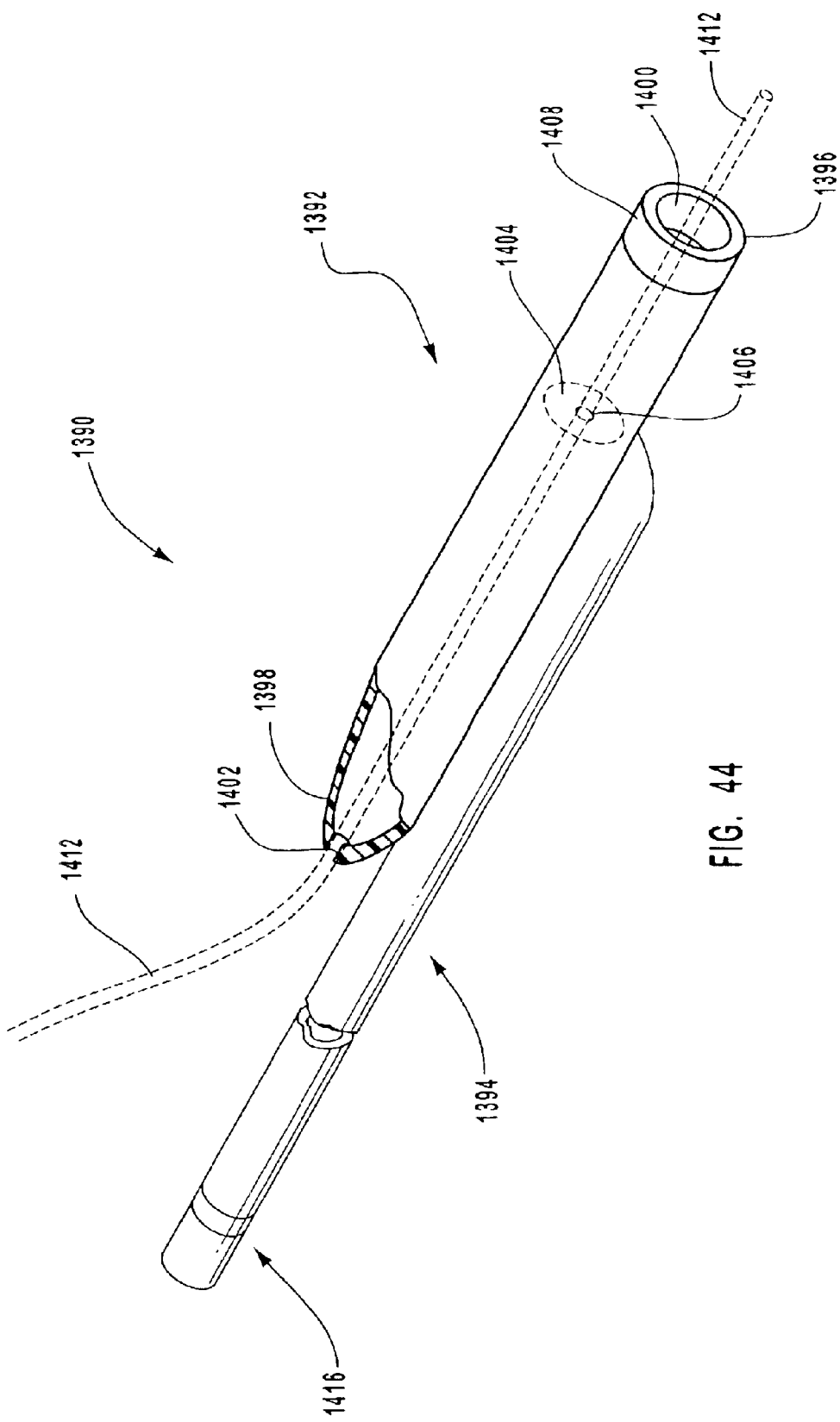
FIG. 44 illustrates a perspective view of another embodiment of a capture catheter used with the filter device of the present invention.

As illustrated in FIG. 44 an alternate embodiment of a capture catheter, designated by reference number 1390 is illustrated. As shown, capture catheter 1390 includes a distal portion 1392 and a positioning member 1394 connected or attached to distal portion 1392. The distal portion 1392 includes a lumen 1400 extending from a distal end 1396 to terminate at an aperture 1402 at a proximal end 1398 thereof. The distal end 1396 optionally includes a radiopaque marker or band 1408, while lumen 1400 is configured to receive a filter assembly of a filter device in a similar manner to lumen 92 of capture catheter 90. Alternatively, lumen 1400 can include a stop member 1404, depicted in dotted lines, with a hole 1406 therethrough. The stop member 1404 allows guide member 1412 to pass through hole 1406, but prevents a filter assembly disposed at a distal end of guide member 1412 to pass through hole 1406 once capture catheter 1390 has received the filter assembly within lumen 1400. One skilled in the art can identify various other configurations of stop member. For instance, hole 1406 can be disposed in stop member 1404 at any location.

To move capture catheter 1390 along guide member 1412 of the filter device, capture catheter 1390 includes positioning member 1394. This positioning member 1394 has sufficient stiffness that application of a force at a proximal end 1416 can be transferred to longitudinal motion of distal portion 1392 of capture catheter 1390. In one configuration, positioning member 1394 is a solid member, while in another configuration positioning member 1394 is hollow or has at least a portion thereof hollow. The positioning member 1394 can be fabricated from a polymer, a plastic, polymer, a synthetic material, a metal, an alloy, combinations thereof, or other material that can be used for medical devices and has the needed stiffness.

Figure 45:
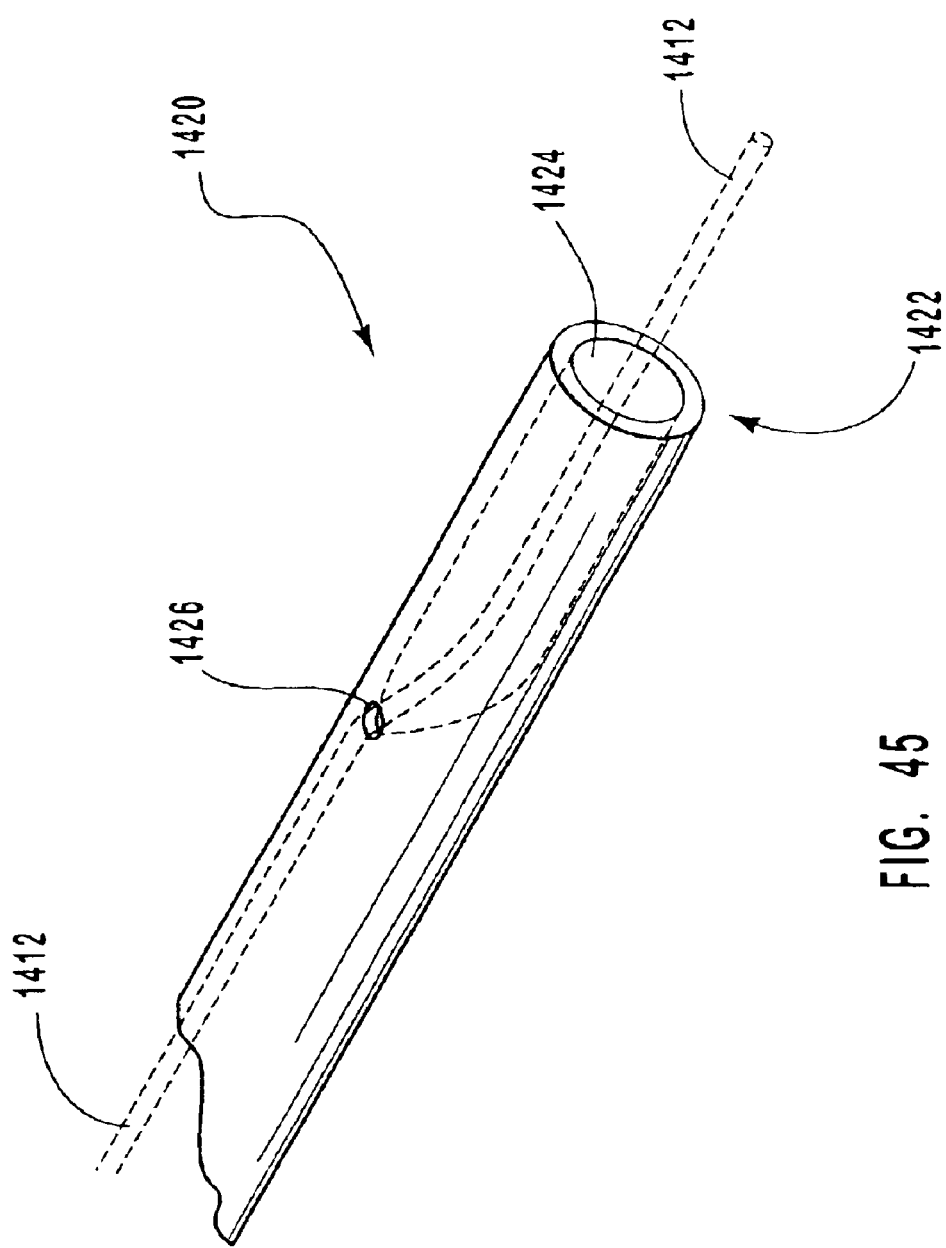
FIG. 45 illustrates a perspective view of yet another embodiment of a capture catheter used with the filter device of the present invention.

As illustrated in FIG. 45 an alternate embodiment of a capture catheter, designated by reference number 1420 is illustrated. As shown, capture catheter 1420 includes a distal end 1422 and a lumen 1424 extending from distal end 1422 to terminate at an aperture 1426 at a location proximal to distal end 1422. Lumen 1424 is configured to receive a filter assembly of a filter device in a similar manner to lumen 92 of capture catheter 90, while aperture 1426 is adapted to receive guide member 1412 and prevent passage of filter assembly of the filter device. In this configuration, the length of lumen 1424 is configured to prevent capture catheter 1420 from being advanced further over the filter device or filter assembly of the filter device than is required. Alternatively, lumen 1424 can include a stop member similar to stop member 1404 discussed herein. Furthermore, capture catheter 1420 can optionally include one or more radiopaque markers disposed at and/or between a distal end and a proximal end thereof.

Figure 46:
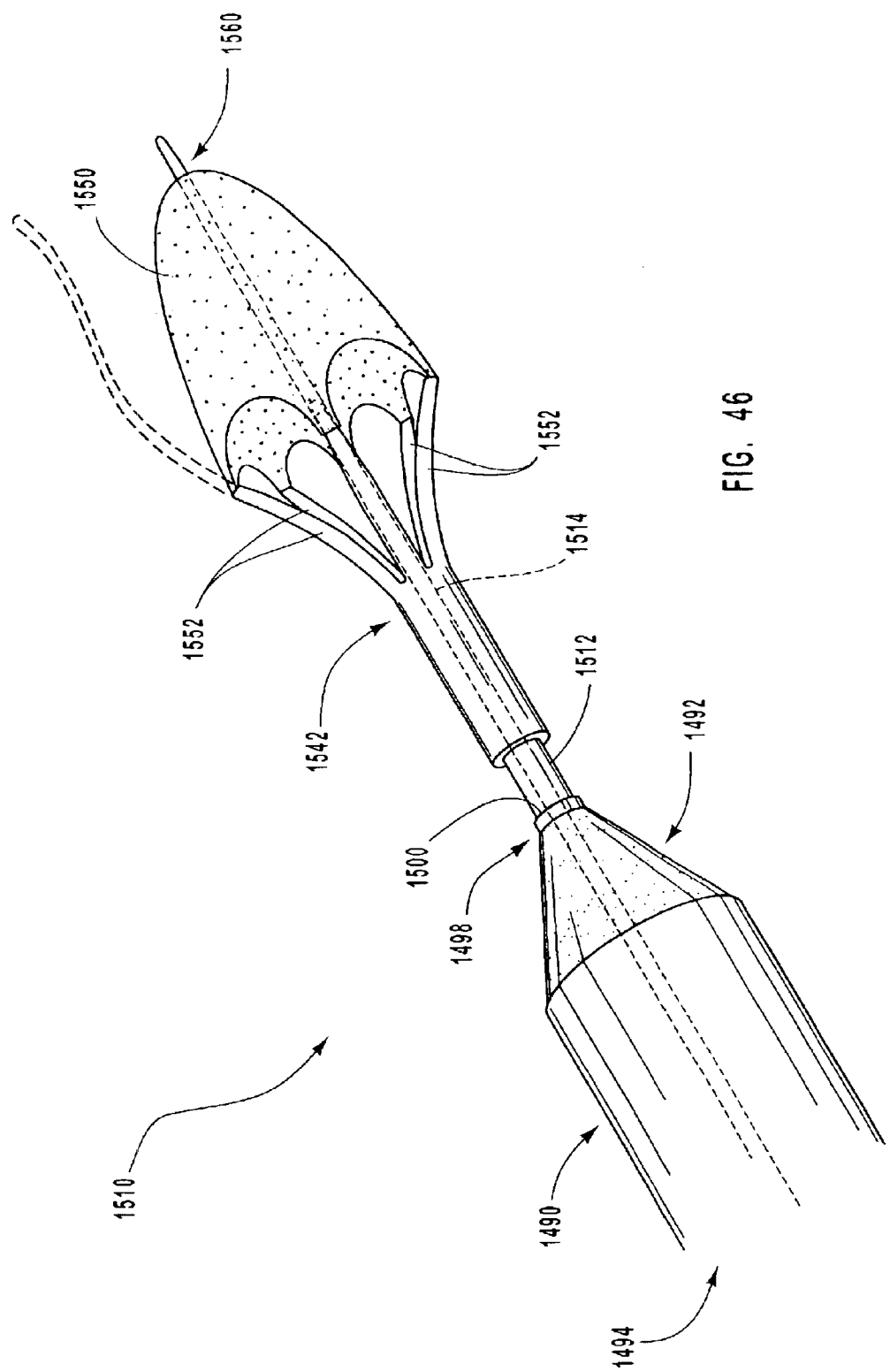
FIG. 46 illustrates a perspective view of still another embodiment of a capture catheter used with the filter device of the present invention.

Referring now to FIG. 46, depicted is another embodiment of a capture catheter in accordance with another aspect of the present invention. As illustrated, capture catheter 1490 is adapted to cooperate with a filter device 1510. The illustrative filter device 1510 includes a filter assembly 1542 coupled to a distal end 1514 of guide member 1512. The filter assembly 1542 includes a plurality of struts 1552 and a filter 1550 connected to one or more of the plurality of struts 1552. As shown, filter assembly 1542 is a separate component that is attached, connected, or coupled to guide member 1512. In an alternate configuration, however, filter assembly 1542 can be integrally formed with guide member 1512, such that each of the plurality of struts 1552 is formed from a portion of guide member 1512. Also forming part of filter assembly 1542 is an atraumatic tip 1560. This atraumatic tip 1560 can be disposed through filter 1550 of filter assembly 1542. Alternatively, atraumatic tip 1560 can pass around filter 1550, as depicted in dotted lines, and be configured from one of the plurality of struts 1552 that elongated.

Returning to capture catheter 1490, the capture catheter 1490 includes a distal portion 1492 and a proximal portion 1494 that communicates with the distal portion 1492. The proximal portion 1494 is stiffer than the distal portion 1492 and can have a similar configuration to the other capture catheters described herein. For instance, proximal portion 1494 can be capture catheter 90, can have a similar configuration to distal portion 1392 of capture catheter 1390, or can be capture catheter 1420. The distal portion 1492 is flexible and tapers from proximal to proximal portion 1494 to a distal end 1498 of capture catheter 1490.

Figure 47:
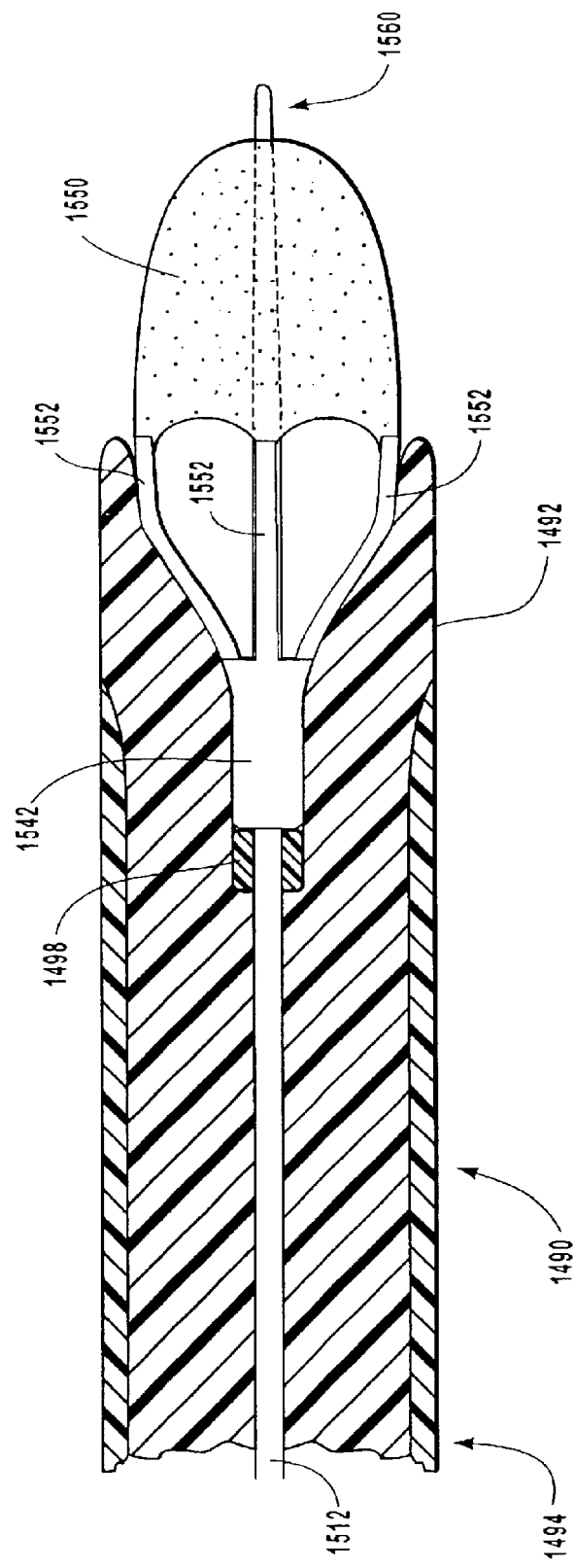
FIG. 47 illustrates a side view of the capture catheter of FIG. 46 as it begins to capture the filter device of the present invention.
Figure 48:
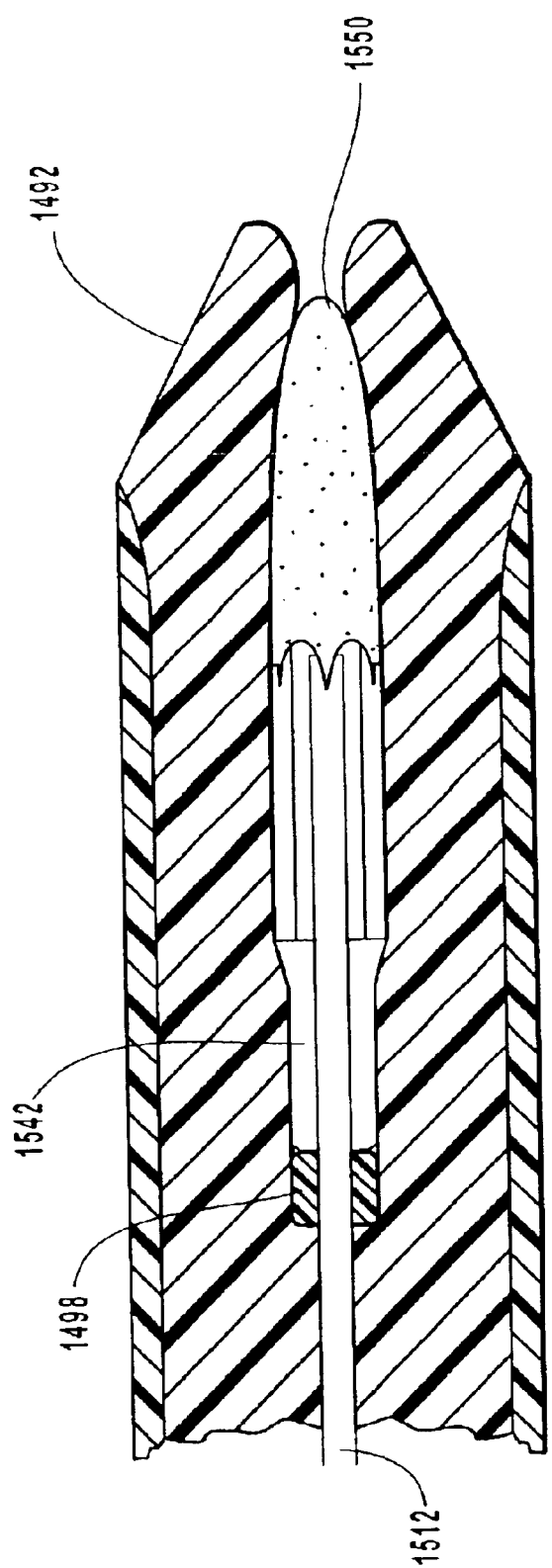
FIG. 48 illustrates a side view of the capture catheter of FIG. 46 as it captures the filter device of the present invention.

Disposed at distal end 1498 is a lumen 1500 that receives guide member 1512 of filter device 1510. Lumen 1500 can be formed from a separate tubular member that is connected, attached, or coupled to the distal end of capture catheter 1490. Alternatively, lumen 1500 can be formed from the distal portion 1492 of capture catheter 1490. The lumen 1500 is adapted to slidably receive guide member 1512 of filter device 1510, but prevent passage of filter assembly 1542. Stated another way, filter assembly 1542 has an outer diameter greater than the inner diameter of lumen 1500. Consequently, as capture catheter 1490 is moved in a distal direction, distal end 1498 engages with either a proximal end of filter assembly 1542 or one or more of the extending struts 1552. As capture catheter 1490 continues to be advanced, distal portion 1492, due to its flexibility, begins to invert, as depicted in FIG. 47. As capture catheter 1490 is continued to be advanced, struts 1552 and filter 1550 are completely enclosed within capture catheter 1490, as shown in FIG. 48.

Embodiments of the present invention and the various components or elements thereof can be used interchangeably so that features and functions of one exemplary embodiment of a filter device can be used with other embodiments of the filter device. Illustratively, the restraining members or mechanisms of the described embodiments of the present invention can be used with multiple different configurations of the filter device. Further, exemplary capture catheters can be used interchangeably such that any capture catheter can be used with any of the described filter devices and such other that may be known to those skilled in the art in light of the teaching contained herein. Additionally, methods of using one embodiment of the present invention can be used with other embodiments of the present invention. Therefore, embodiments of the present invention provide filter devices that have small, low, or no profiles, few parts and components, are simple to manufacture and use, are able to be easily inserted into a patient, be steerable through the tortuous anatomy of a patient, provide filtering capabilities, provide exchange capability so other medical devices can be advanced over or along the filter device, and be capable of removing captured material without allowing such material to escape during filter retrieval.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A filter device for percutaneous insertion into a blood vessel during a procedure, the filter device comprising:
   (a) a guide member comprising a distal end, a proximal end, and a lumen extending from the distal end to the proximal end, said distal end being an atraumatic tip having a level of resiliency sufficient to maintain a curvature defined by a physician or clinician;
   (b) means for filtering material from a blood stream, said means being disposed within said lumen of said guide member and having a proximal end and a distal end; and
   (c) means for deploying said means for filtering from said lumen of said guide member into the blood stream in the blood vessel through said atraumatic tip and retracting said means for filtering upon completing the procedure.

2. A filter device as recited in claim 1, wherein said means for deploying comprises an actuating assembly.

3. A filter device as recited in claim 2, wherein said actuating assembly comprises an actuating member and an actuating element.

4. A filter device as recited in claim 3, wherein said actuating element is moveable by a human.

5. A filter device as recited in claim 3, wherein said actuating element is a moveable by a removable clamp set.

6. A filter device as recited in claim 3, wherein said actuating element is coupled to said guide member.

7. A filter device as recited in claim 3, wherein said actuating element comprises an open indicator, a closed indicator, and a refracted indicator.

8. A filter device as recited in claim 1, wherein said means for filtering comprises a filter.

9. A filter device as recited in claim 1, wherein said means for deploying comprises an actuating member coupled to an actuator head, said actuator head communicating with said means for filtering.

10. A filter device as recited in claim 1, wherein said means for filtering comprises means for opening an end of said means for filtering.

11. A filter device as recited in claim 10, wherein said means for opening comprises a biased member.

12. A filter device comprising:
   (a) a guide member comprising a distal end, a proximal end, and a lumen extending from said distal end to said proximal end, said distal end being an atraumatic tip having a level of resiliency sufficient to maintain a curvature defined by a physician or clinician;
   (b) an actuating assembly coupled to said guide member, said actuating assembly comprising:
      (i) an actuating member disposed within said lumen of said guide member, said actuating member having a proximal end and a distal end; and
      (ii) an actuating mechanism coupled to said distal end of said guide member and to said actuating member; and
   (c) a filter assembly disposed within said lumen and deployable by said actuating member through said atraumatic tip and from said lumen, said filter assembly comprising:
      (i) a filter comprising a proximal end with an opening formed therein; and
      (ii) a plurality of struts coupled to said proximal end of said filter and said actuating member, at least one of said plurality of struts being biased to open said opening.

13. The filter device a recited in claim 12, wherein said actuating member is partially disposed in said lumen of said guide member.

14. A method for operating a vascular filter device during a procedure, comprising:
   (a) inserting a filter device into the vasculature of a patient distal of a portion of a blood vessel to be accessed during a procedure, said filter device comprising:
      (i) a guide member having a proximal end, a distal end, and a lumen extending from said distal end, said distal end being an atraumatic tip having a level of resiliency sufficient to maintain a curvature defined by a physician or clinician; and
      (ii) a filter disposed within said lumen at said distal end of said guide member, said filter having a distal end;
      (iii) an actuating member disposed within said lumen of said guide member;
   (b) deploying said filter through said atraumatic tip and from within said lumen into the blood stream to capture material that is dislodged during the procedure;
   (c) retracting said filter until an open-ended proximal end thereof is positioned in relationship with said guide member to prevent said captured material from escaping from said filter; and
   (d) upon positioning a capture catheter to enclose said filter, removing said filter device and said capture catheter from the vasculature of the patient.

15. A method as recited in claim 14, further comprising locking said capture catheter to said guide member.

16. A method as recited in claim 15, further comprising actuating said actuating member to deploy said filter.

17. A method as recited in claim 14, wherein retracting said filter comprises retracting said open-ended proximal end of said filter until said proximal end is in contact with said guide member.

18. A method as recited in claim 14, wherein retracting said filter comprises retracting said open-ended proximal end of said filter into said lumen of said guide member.

19. A method as recited in claim 14, wherein deploying said filter comprises pushing said filter from said lumen.

20. A method as recited in claim 19, further comprising expanding said proximal end of said filter to form an opening.

21. A method as recited in claim 20, wherein expanding said proximal end further comprises automatically expanding said proximal end through rotational motion of an actuating member disposed in said lumen.

22. A method for removing a vascular filter device, comprising:
   (a) following deploying a filter of a filter assembly from a guide member, through an atraumatic tip of said guide member distal having a level of resiliency sufficient to maintain a curvature defined by a physician or clinician, by moving an actuating member, disposed within a lumen of said guide member in a distal direction, retracting said filter until an opened proximal end of said filter is positioned in relationship with said guide member to prevent the captured material from escaping from said filter; and (b) upon positioning a capture catheter to enclose said filter, removing said filter device and said capture catheter from the vasculature of the patient.

23. A method as recited in claim 22, wherein retracting said filter comprises moving said actuating member in a proximal direction by moving an actuator element in a proximal direction.

24. A method as recited in claim 23, wherein moving said actuating member further comprises moving a first clamp set coupled to said actuator element to move said actuating member.

25. A method as recited in claim 23, wherein moving said actuating member further comprises moving said actuator element by-hand to move said actuating member.

26. A method as recited in claim 23, further comprising locking said capture catheter to said guide member.

* * * * *

UNITED STATES PATENT AND TRADEMARK OFFICE
CERTIFICATE OF CORRECTION

PATENT NO.        : 6,951,570 B2  
APPLICATION NO. : 10/186255  
DATED             : October 4, 2005  
INVENTOR(S)       : Richard J. Linder et al.

Page 1 of 1

It is certified that error appears in the above-identified patent and that said Letters Patent is hereby corrected as shown below:

Claim 7, column 31, line 45, replace "refracted" with --retracted--

Signed and Sealed this

Nineteenth Day of December, 2006

JON W. DUDAS  
*Director of the United States Patent and Trademark Office*